United States Patent
Harada et al.

(10) Patent No.: US 7,592,407 B2
(45) Date of Patent: Sep. 22, 2009

(54) POLYMERIZABLE FLUORINATED COMPOUND, MAKING METHOD, POLYMER, RESIST COMPOSITION AND PATTERNING PROCESS

(75) Inventors: Yuji Harada, Joetsu (JP); Jun Hatakeyama, Joetsu (JP); Takeru Watanabe, Joetsu (JP); Takeshi Kinsho, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 489 days.

(21) Appl. No.: 11/259,179

(22) Filed: Oct. 27, 2005

(65) Prior Publication Data

US 2006/0094817 A1    May 4, 2006

(30) Foreign Application Priority Data

Oct. 28, 2004    (JP)    ............... 2004-313903

(51) Int. Cl.
*C07C 69/52*    (2006.01)
(52) U.S. Cl. ............ 526/245; 430/270.1; 549/428; 568/669; 570/136; 570/142; 570/182; 570/186; 524/544
(58) Field of Classification Search ............. 568/669; 549/428; 430/270.1; 570/136, 142; 526/245
See application file for complete search history.

(56) References Cited

U.S. PATENT DOCUMENTS 4,491,628 A    1/1985    Ito et al.

(Continued)

FOREIGN PATENT DOCUMENTS

EP    1 449 839 A2    8/2004
EP    1449839 A2 *    8/2004

(Continued)

OTHER PUBLICATIONS

Middleton et al., J. Amer. Chem. Soc., vol. 86(22), pp. 4948-4952, (1964).*

(Continued)

*Primary Examiner*—Peter D. Mulcahy
*Assistant Examiner*—Henry Hu
(74) *Attorney, Agent, or Firm*—Birch, Stewart, Kolasch & Birch, LLP

(57) ABSTRACT

A polymerizable fluorinated compound having formula (2a) or (2b) wherein $R^1$ and $R^2$ are H or $C_1$-$C_{20}$ alkyl or fluoroalkyl, $R^3$ is H, F or $C_1$-$C_4$ alkyl or fluoroalkyl, and R is H or a protective group is polymerized into a fluorinated polymer which is used as a base polymer to formulate a resist composition having transparency to laser light of wavelength $\leq 300$ nm, alkali development amenability, and dry etch resistance.

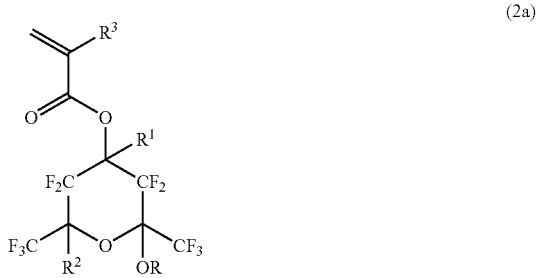

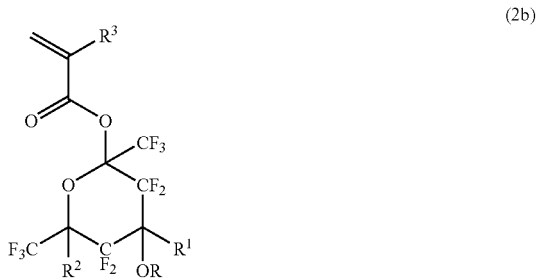

4 Claims, 1 Drawing Sheet

U.S. PATENT DOCUMENTS

| | | | |
|---|---|---|---|
| 5,310,619 A | 5/1994 | Crivello et al. | |
| 5,968,713 A | 10/1999 | Nozaki et al. | |
| 6,013,416 A | 1/2000 | Nozaki et al. | |
| 6,200,725 B1 | 3/2001 | Takechi et al. | |
| 6,280,898 B1 | 8/2001 | Hasegawa et al. | |
| 6,329,125 B2 | 12/2001 | Takechi et al. | |
| 6,784,312 B2 * | 8/2004 | Miyazawa et al. | 560/205 |
| 6,858,692 B2 * | 2/2005 | Kaneko et al. | 526/252 |
| 7,015,366 B2 * | 3/2006 | Kodama et al. | 568/840 |
| 2001/0026901 A1 | 10/2001 | Maeda et al. | |

FOREIGN PATENT DOCUMENTS

| | | |
|---|---|---|
| JP | 63-27829 A | 2/1988 |
| JP | 2-27660 B2 | 6/1990 |
| JP | 9-73173 A | 3/1997 |
| JP | 9-90637 A | 4/1997 |
| JP | 9-230595 A | 9/1997 |
| JP | 10-10739 A | 1/1998 |
| JP | 2000-26446 A | 1/2000 |
| JP | 2000-159758 A | 6/2000 |
| WO | WO-97/33198 A1 | 9/1997 |

OTHER PUBLICATIONS

Proc. SPIE, vol. 5376, p. 44 (2004).
Proc. SPIE, vol. 5040, p. 724 (2003).
Proc. SPIE, vol. 3999, p. 2 (2000).
Journal of Photopolymer Science and Technology, vol. 5, No. 1, p. 85 (1992).
Proc. SPIE, vol. 5376, p. 556 (2004).
T. Nakai et al., Tetrahedron Letters, vol. 29, p. 4119, 1988.
T. Nakai et al., Organic Synthesis, vol. 76, p. 151, 1998.
Jakubek V et al., Proceedings of SPIE, vol. 5376, pp. 554-564, XP002364108 (May 2004).

* cited by examiner

POLYMERIZABLE FLUORINATED COMPOUND, MAKING METHOD, POLYMER, RESIST COMPOSITION AND PATTERNING PROCESS

CROSS-REFERENCE TO RELATED APPLICATION

This non-provisional application claims priority under 35 U.S.C. §119(a) on Patent Application No. 2004-313903 filed in Japan on Oct. 28, 2004, the entire contents of which are hereby incorporated by reference.

TECHNICAL FIELD

This invention relates to a fluorinated polymer useful as a base polymer in resist compositions, especially chemically amplified resist compositions for the lithographic micropatterning technology, a polymerizable fluorinated ester compound from which the fluorinated polymer is derived, a method for preparing the polymerizable fluorinated compound, and a fluorinated compound as an intermediate. It also relates to a resist composition comprising the fluorinated polymer and a patterning process.

BACKGROUND ART

In the recent drive for higher integration and operating speeds in LSI devices, the pattern rule is made drastically finer. The rapid advance toward finer pattern rules is grounded on the development of a light source of a shorter wavelength, a projection lens with an increased numerical aperture (NA), and a resist material with improved performance.

With respect to the light source for exposure, the changeover from i-line (365 nm) to shorter wavelength KrF laser (248 nm) enabled mass-scale production of DRAM with an integration degree of 64 MB (processing feature size≦0.25 μm). To establish the micropatterning technology (processing feature size≦0.2 μm) necessary for the fabrication of DRAM with an integration degree of 256 MB and 1 GB or more, the lithography using ArF excimer laser (193 nm) is under active investigation. Although $F_2$ laser (157 nm) is also considered as one candidate light source of shorter wavelength, the use of $F_2$ laser is postponed because of many outstanding problems including a more expensive scanner.

With respect to the increase of NA, not only an improvement in lens performance is sought for, but also the immersion lithography which can establish an NA of 1.00 or greater by filling a high refractive index liquid between a lens and a wafer is of great interest (see Proc. SPIE, Vol. 5376, p44 (2004)). For the ArF immersion lithography now under investigation, it was proposed to apply to the 45-nm node by filling the space between the lens and the wafer with deionized water having a refractive index of 1.44 (see Proc. SPIE, Vol. 5040, p724 (2003)).

With respect to the resist material, since the development of acid-catalyzed chemical amplification positive working resist materials as disclosed in U.S. Pat. Nos. 4,491,628 and 5,310,619 (JP-B 2-27660 and JP-A 63-27829), it has become possible to achieve a higher resolution and sensitivity. They now become predominant resist materials adapted for deep UV lithography. Of these, the KrF resist materials enjoyed early use on the 0.3 micron process, passed through the 0.25 micron rule, and currently entered the mass production phase on the 0.18 micron rule. Engineers have started investigation on the 0.15 micron rule. The ArF resist is expected to enable miniaturization of the design rule to 0.13 μm or less.

Various alkali-soluble resins are used as the base resin in such chemically amplified resist compositions. Depending on a light source selected for light exposure, a base resin of different skeleton is used. For KrF resists, a polyhydroxystyrene resin having phenolic hydroxyl groups as the alkali-soluble group is now a standard base resin. On the other hand, for ArF resists, since polyhydroxystyrene resins and novolac resins have very strong absorption at a wavelength around 193 nm, studies were made on poly(meth)acrylate resins and resins comprising cycloaliphatic olefin such as norbornene as polymerized units, both using carboxyl groups as the alkali-soluble group (see JP-A 9-73173, JP-A 10-10739, JP-A 9-230595 and WO 97/33198). Of these, the poly(meth)acrylate resins are expected to reach a practical level because of ease of polymerization. One of the poly(meth)acrylate resins proposed thus far is a poly(meth)acrylate resin having methyladamantyl groups as the acid labile group and lactone rings as the adhesive group as disclosed in JP-A 9-90637. Norbornyl lactone is also proposed as an adhesive group, having enhanced etching resistance as disclosed in JP-A 2000-26446 and JP-A 2000-159758.

In the case of ArF resist materials, since carboxyl groups as the alkali-soluble functional group have a higher acidity than phenolic hydroxyl groups and hydrophobic cycloaliphatic groups are contained in the polymer skeleton, it is difficult to control the alkali solubility of the resin. This tends to allow for swelling, resulting in undesired phenomena including pattern collapse, increased line edge roughness, and resides left during development. The swell quantity of resist during development can be electrically determined by the quartz crystal microbalance (QCM) technique. With this technique, it was confirmed in Proc. SPIE, Vol. 3999, p2 (2000) that ArF resist materials comprising cycloolefin polymers as the base resin, especially having carboxyl groups as the adhesive group, undergo noticeable swell.

In order to solve these and other problems, it would be necessary to develop a resin having acidic functional groups with an appropriate alkali solubility like phenolic hydroxyl groups on polyhydroxystyrene used in the KrF resist materials. One functional group with an equivalent acidity to phenolic hydroxyl groups is a fluorinated alcohol represented by the partial structure —$C(CF_3)_2OH$ as proposed in Journal of Photopolymer Science and Technology, Vol. 5, No. 1, p85 (1992). It was observed that polystyrene and norbornene polymers having this functional group incorporated therein exhibit an equivalent alkali solubility to the polyhydroxystyrene. Regrettably, hexafluoroacetone (b.p. −27° C.) used as the starting reactant to incorporate the partial structure —$C(CF_3)_2OH$ is very toxic and gaseous at room temperature, and thus quite awkward to handle. There exists a strong need for a polymerizable compound which is easy to synthesize in an industrial manner and which have both a (meth)acrylate structure ensuring ease of preparation (polymerization) into a resist resin and functional groups with an equivalent acidity to phenolic hydroxyl groups. One of such recently proposed compounds is an acrylate having as a pendant a tetrahydropyran ring containing trifluoromethyl and hydroxy groups within the ring as reported in Proc. SPIE, Vol. 5376, p556 (2004).

SUMMARY OF THE INVENTION

An object of the invention is to provide a novel fluorinated polymer which is used to formulate a resist composition having transparency to laser light having a wavelength of up to 300 nm, especially up to 200 nm, alkali development amenability, and dry etch resistance; a polymerizable fluorinated ester compound from which the fluorinated polymer is derived; a method for preparing the polymerizable fluorinated compound; and a fluorinated compound as an intermediate.

Another object is to provide a resist composition, especially chemically amplified positive resist composition, comprising the fluorinated polymer as a base resin and a patterning process using the same.

The inventor has discovered that a fluorinated compound having the general formula (1), defined below, and a polymerizable fluorinated ester compound having the general formula (2), defined below, can be synthesized from readily available reactants in high yields by the simple method described later; that the polymerizable fluorinated ester compound can be polymerized by radical polymerization and similar techniques which can be readily implemented on an industrial basis; and that a resin resulting from polymerization is used to formulate a chemically amplified resist composition having transparency at a wavelength of up to 200 nm, alkali development amenability, etch resistance, and minimal line edge roughness.

Embodiments of the present invention include a fluorinated compound, a polymerizable fluorinated ester compound, a method for preparing the same, a polymer obtained therefrom, a resist composition, and a patterning process.

In a first aspect, the invention provides a fluorinated compound having the general formula (1):

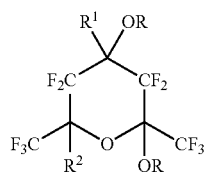
(1)

wherein $R^1$ and $R^2$ each are hydrogen or a straight, branched or cyclic $C_1$-$C_{20}$ alkyl or fluoroalkyl group, and R is hydrogen or a protective group.

In a second aspect, the invention provides a polymerizable fluorinated compound having the general formula (2a) or (2b):

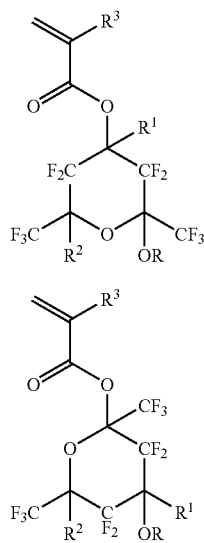
(2a)

(2b)

wherein $R^1$ and $R^2$ each are hydrogen or a straight, branched or cyclic $C_1$-$C_{20}$ alkyl or fluoroalkyl group, $R^3$ is hydrogen, fluorine, or a $C_1$-$C_4$ alkyl or fluoroalkyl group, and R is hydrogen or a protective group.

In a third aspect, the invention provides a method for preparing a polymerizable fluorinated compound having the general formula (2a-1) or (2b-1), comprising the steps of reacting an ester compound having the formula: $R^1CO_2R^4$ with an enolate compound having the general formula (3), further reacting the reaction product with a compound having the formula: $R^2$-Z to form a compound having the general formula (1-1), and acylating the compound having formula (1-1) to form a polymerizable fluorinated compound having the general formula (2a-1) or (2b-1).

(3)

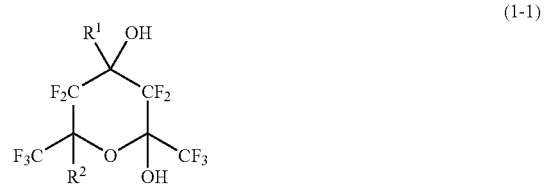
(1-1)

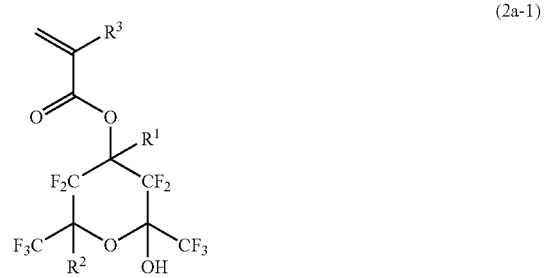
(2a-1)

(2b-1)

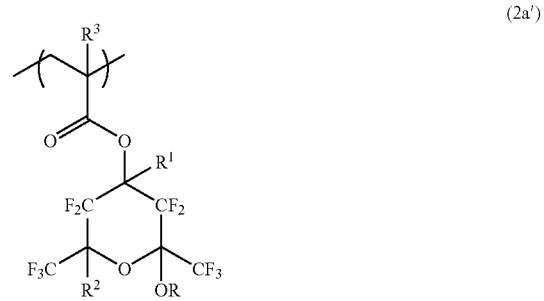

Herein $R^1$ and $R^2$ each are hydrogen or a straight, branched or cyclic $C_1$-$C_{20}$ alkyl or fluoroalkyl group, $R^3$ is hydrogen, fluorine, or a $C_1$-$C_4$ alkyl or fluoroalkyl group, $R^4$ is a $C_1$-$C_{20}$ alkyl group, and Z is such a monovalent group that $R^2$-Z provides a $R^2$ anion equivalent.

In a fourth aspect, the invention provides a polymer comprising recurring units having the general formula (2a') or (2b') and having a weight average molecular weight of 1,000 to 500,000.

(2a')

-continued

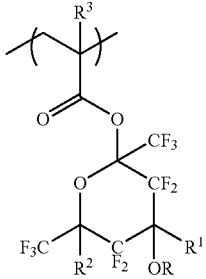
(2b')

Herein $R^1$, $R^2$, $R^3$, and R are as defined above.

In a fifth aspect, the invention provides a resist composition comprising the polymer defined above. Preferably the resist composition comprises (A) the polymer, (B) an organic solvent, and (C) a photoacid generator. The resist composition may further comprise (D) a nitrogen-containing organic compound and/or (E) a dissolution inhibitor.

In a sixth aspect, the invention provides a process for forming a pattern, comprising the steps of (1) applying the resist composition onto a substrate to form a coating, (2) heat treating the coating and exposing the coating to high-energy radiation with a wavelength of up to 300 nm through a photomask, and (3) developing the coating with a developer. In a seventh aspect, the invention provides a process for forming a pattern, comprising the steps of (1) applying the resist composition onto a substrate to form a coating, (2) heat treating the coated substrate, introducing a liquid between the coated substrate and a projection lens, and exposing the coating to high-energy radiation with a wavelength of up to 300 nm through a photomask, and (3) developing the coating with a developer. In a preferred embodiment, the high-energy radiation is KrF excimer laser, ArF excimer laser, $F_2$ laser, $Ar_2$ laser or soft x-ray.

When processed by the lithography involving ArF exposure, the resist composition comprising the inventive polymer exhibits a high resolution, minimized line edge roughness, etch resistance, and minimized surface roughness after etching.

The polymerizable fluorinated ester compounds of the invention are novel. They are useful as raw materials for the synthesis of polymers, functional materials, pharmaceutical and agricultural chemicals. They are most useful as monomers to produce polymers for the manufacture of radiation-sensitive resist compositions which are fully transparent to radiation having a wavelength of up to 300 nm, especially up to 200 nm, and exhibit improved development performance due to the inclusion of phenol-like acidic hydroxyl groups.

As used herein, the notation ($C_n$-$C_m$) means a group containing from n to m carbon atoms per group.

DESCRIPTION OF THE PREFERRED EMBODIMENTS

Fluorinated Compound

Figure 1:
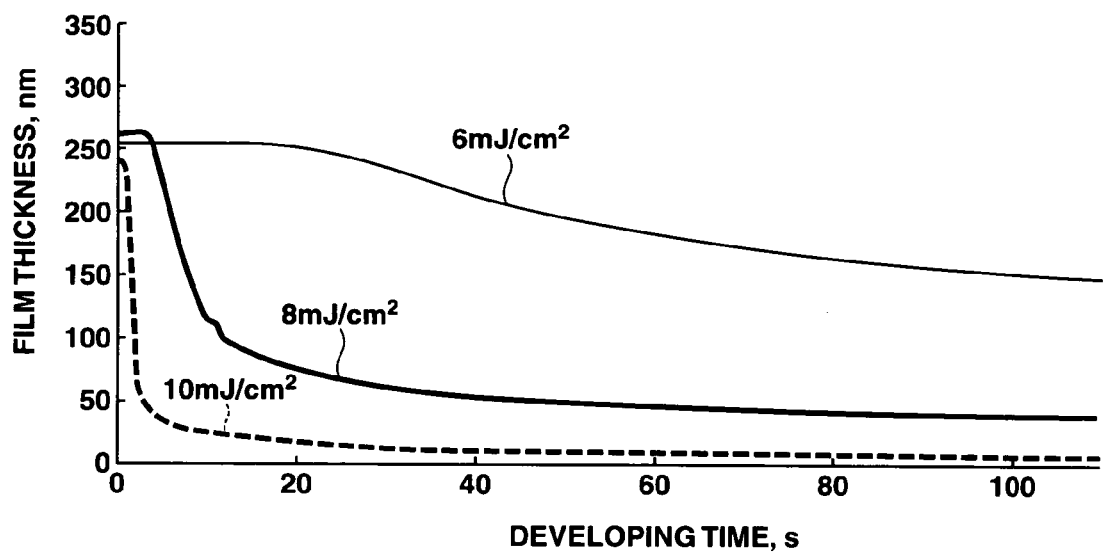
FIG. 1 is a graph showing the thickness versus developing time of a resist film formed from the resist composition of Polymer 1, as analyzed by the QCM technique.

In the first embodiment, the fluorinated compounds of the invention have the general formulae (1), (2a) and (2b). More specifically they are compounds having the general formulae (1-1), (2a-1) and (2b-1), modified compounds of formula (1-1) in which one or both of the hydroxyl groups are blocked or protected with protective groups, and modified compounds of formulae (2a-1) and (2b-1) in which the hydroxyl group is blocked or protected with a protective group.

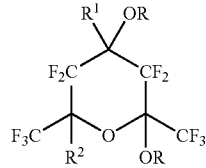
(1)

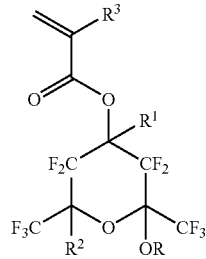
(2a)

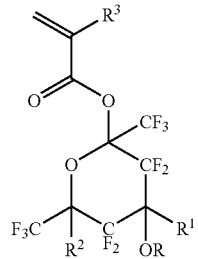
(2b)

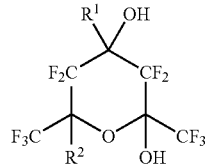
(1-1)

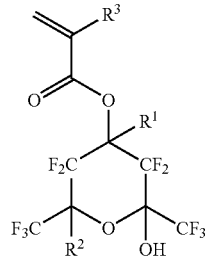
(2a-1)

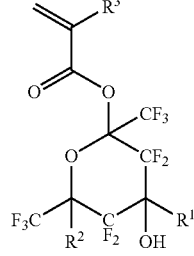
(2b-1)

Herein $R^1$ and $R^2$ each are hydrogen or a straight, branched or cyclic $C_1$-$C_{20}$ alkyl or fluoroalkyl group, $R^3$ is hydrogen, fluorine, or a $C_1$-$C_4$ alkyl or fluoroalkyl group, and R is hydrogen or a protective group.

In the compounds having formulae (1), (2a) and (2b), there can be present enantiomers or diastereomers which are associated with an asymmetric carbon atom or 6-membered ring structure. The general formula (1), (2a) or (2b) collectively represents all such stereoisomers. The stereoisomers may be used alone or in admixture.

Suitable straight, branched or cyclic $C_1$-$C_{20}$ alkyl groups represented by $R^1$ and $R^2$ include, for example, methyl, ethyl, propyl, isopropyl, n-butyl, sec-butyl, tert-butyl, tert-amyl, n-pentyl, n-hexyl, n-octyl, n-nonyl, n-decyl, cyclopropyl, cyclobutyl, cyclopentyl, cyclohexyl, cyclopentylmethyl, cyclopentylethyl, cyclopentylbutyl, cyclohexylmethyl, cyclohexylethyl, and cyclohexylbutyl. Suitable straight, branched or cyclic $C_1$-$C_{20}$ fluoroalkyl groups include the foregoing alkyl groups in which one or more hydrogen atoms are replaced by fluorine atoms, for example, trifluoromethyl, 2,2,2-trifluoroethyl, 3,3,3-trifluoropropyl, 1,1,1,3,3,3-hexafluoroisopropyl, and 1,1,2,2,3,3,3-heptafluoro-n-propyl.

Suitable $C_1$-$C_4$ alkyl groups represented by $R^3$ include, for example, methyl, ethyl, n-propyl, isopropyl, n-butyl, sec-butyl, and tert-butyl. Suitable $C_1$-$C_4$ fluoroalkyl groups represented by $R^3$ include the foregoing alkyl groups in which one or more hydrogen atoms are replaced by fluorine atoms, for example, trifluoromethyl, 2,2,2-trifluoroethyl, 3,3,3-trifluoropropyl, 1,1,1,3,3,3-hexafluoroisopropyl, and 1,1,2,2,3,3,3-heptafluoro-n-propyl.

The protective group for the hydroxyl group in the fluorinated compound, represented by R, is selected from a variety of such groups. Examples of the protective group are groups of the following general formulae (AL-1) to (AL-3), trialkylsilyl groups in which each alkyl moiety has 1 to 6 carbon atoms, and oxoalkyl groups of 4 to 20 carbon atoms.

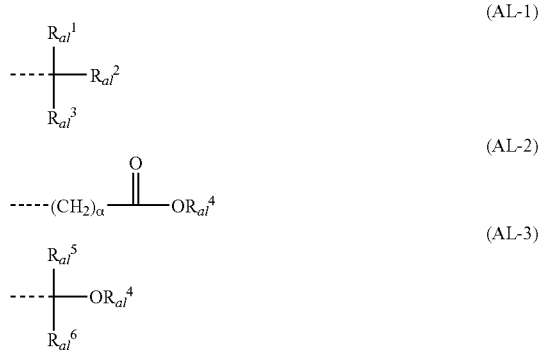

In these formulae and throughout the specification, a broken line denotes a valence bond.

$R_{a1}^1$, $R_{a1}^2$ and $R_{a1}^3$ may be the same or different and stand for straight, branched or cyclic $C_1$-$C_{20}$ hydrocarbon groups, which may contain a hetero atom such as oxygen, sulfur or nitrogen, or bridged cyclic hydrocarbon groups. Alternatively, a pair of $R_{a1}^1$ and $R_{a1}^2$, $R_{a1}^1$ and $R_{a1}^3$, and $R_{a1}^2$ and $R_{a1}^3$, taken together, may form a ring with the carbon atom to which they are bonded. Each of $R_{a1}^1$, $R_{a1}^2$ and $R_{a1}^3$ is a straight or branched $C_1$-$C_{20}$ alkylene group when they form a ring. $R_{a1}^4$ and $R_{a1}^7$ stand for straight, branched or cyclic $C_1$-$C_{20}$ alkyl groups, which may contain a hetero atom such as oxygen, sulfur, nitrogen or fluorine. $R_{a1}^5$ and $R_{a1}^6$ stand for hydrogen or straight, branched or cyclic $C_1$-$C_{20}$ alkyl groups, which may contain a hetero atom such as oxygen, sulfur, nitrogen or fluorine. $R_{a1}^7$ is a monovalent hydrocarbon group of 1 to 18 carbon atoms, preferably 1 to 10 carbon atoms, which may contain a hetero atom such as oxygen, examples of which include straight, branched or cyclic alkyl groups and substituted forms of such alkyl groups in which some hydrogen atoms are replaced by hydroxyl, alkoxy, oxo, amino, alkylamino or other groups. Alternatively, a pair of $R_{a1}^5$ and $R_{a1}^6$, $R_{a1}^5$ and $R_{a1}^7$, and $R_{a1}^6$ and $R_{a1}^7$, taken together, may form a ring with the carbon or carbon and oxygen atoms to which they are bonded. Each of $R_{a1}^5$, $R_{a1}^6$ and $R_{a1}^7$ is a straight or branched $C_1$-$C_{20}$ alkylene group when they form a ring. The subscript α is an integer of 0 to 6.

In formula (AL-1), illustrative examples of $R_{a1}^1$, $R_{a1}^2$ and $R_{a1}^3$ include methyl, ethyl, n-propyl, isopropyl, tert-butyl, cyclohexyl, cyclopentyl, norbornyl, adamantyl, and menthyl. The acid labile groups of formula (AL-1) are exemplified by the substituent groups shown below.

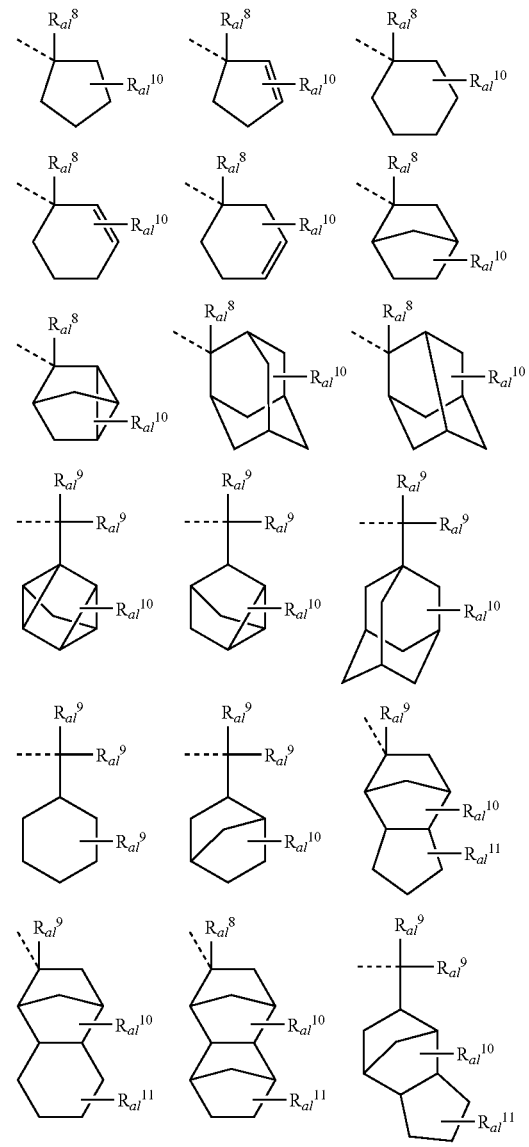

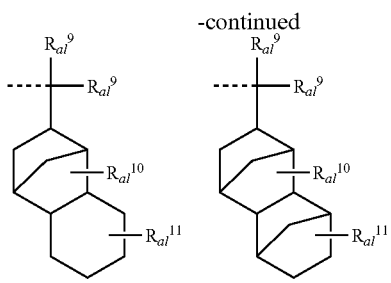

Herein, $R_{a1}^8$ and $R_{a1}^9$ stand for straight, branched or cyclic alkyl groups. $R_{a1}^{10}$ and $R_{a1}^{11}$ stand for hydrogen or monovalent hydrocarbon groups of 1 to 6 carbon atoms, which may contain a hetero atom and which may be straight, branched or cyclic.

Illustrative examples of $R_{a1}^8$ and $R_{a1}^9$ include methyl, ethyl, propyl, isopropyl, n-butyl, sec-butyl, n-pentyl, n-hexyl, cyclopropyl, cyclopropylmethyl, cyclobutyl, cyclopentyl, and cyclohexyl. Illustrative examples of $R_{a1}^{10}$ and $R_{a1}^{11}$ include methyl, ethyl, n-propyl, isopropyl, n-butyl, sec-butyl, n-pentyl, n-hexyl, hydroxymethyl, hydroxyethyl, methoxy, methoxymethoxy, ethoxy, and tert-butoxy. When $R_{a1}^{10}$ and $R_{a1}^{11}$ contain hetero atoms such as oxygen, sulfur or nitrogen, they may be contained, for example, in the form of —OH, —OR$^{a112}$, —O—, —S—, —S(=O)—, —NH$_2$, —NHR$_{a1}^{12}$, —N(R$_{a1}^{12}$)$_2$, —NH— or —NR$_{a1}^{12}$— wherein $R_{a1}^{12}$ is a $C_1$-$C_5$ alkyl group. Optionally, a hetero atom may intervene in the alkyl chain.

Illustrative examples of the acid labile groups of formula (AL-2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

In formula (AL-3), examples of the straight, branched or cyclic $C_1$-$C_{20}$ alkyl groups represented by $R_{a1}^5$ and $R_{a1}^6$ include methyl, ethyl, propyl, isopropyl, n-butyl, sec-butyl, tert-butyl, cyclopentyl, cyclohexyl, 2-ethylhexyl, and n-octyl. Examples of suitable hydrocarbon groups represented by $R_{a1}^7$ include substituted alkyl groups shown below.

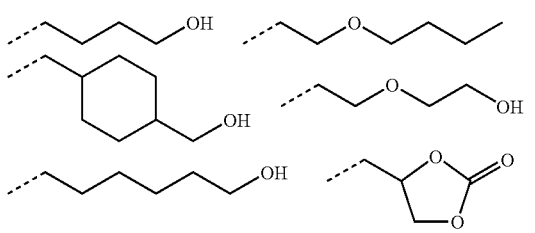

Of the acid labile groups having formula (AL-3), examples of the cyclic groups include tetrahydrofuran-2-yl, 2-methyltetrahydrofuran-2-yl, tetrahydropyran-2-yl, and 2-methyltetrahydropyran-2-yl. Examples of the straight and branched groups are exemplified by the following groups, with ethoxyethyl, butoxyethyl and ethoxypropyl being preferred.

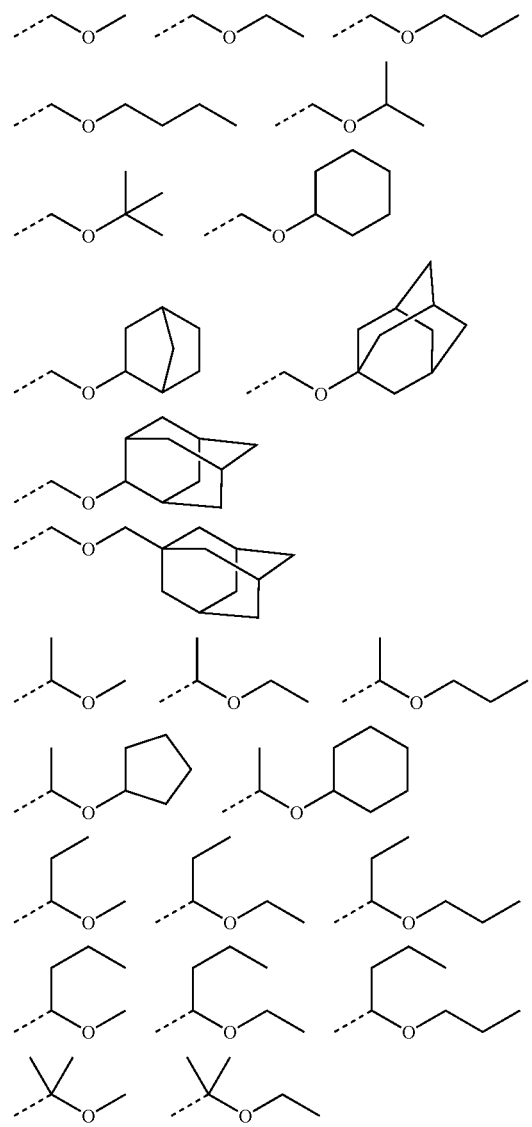

Illustrative, non-limiting examples of the fluorinated compound having formula (1-1) are given below.

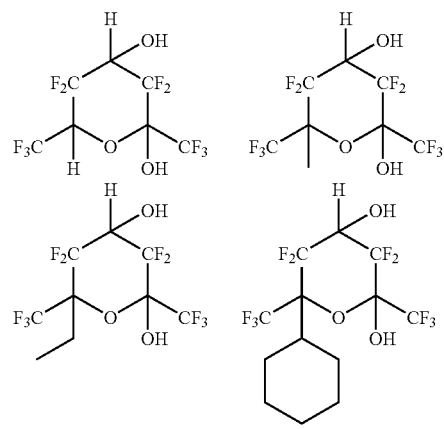

-continued
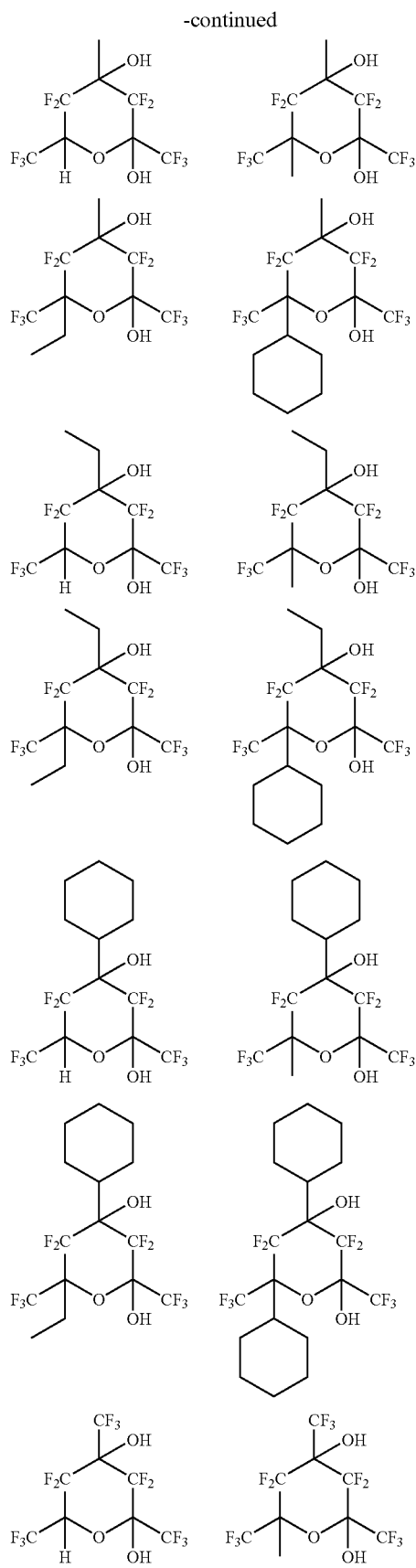
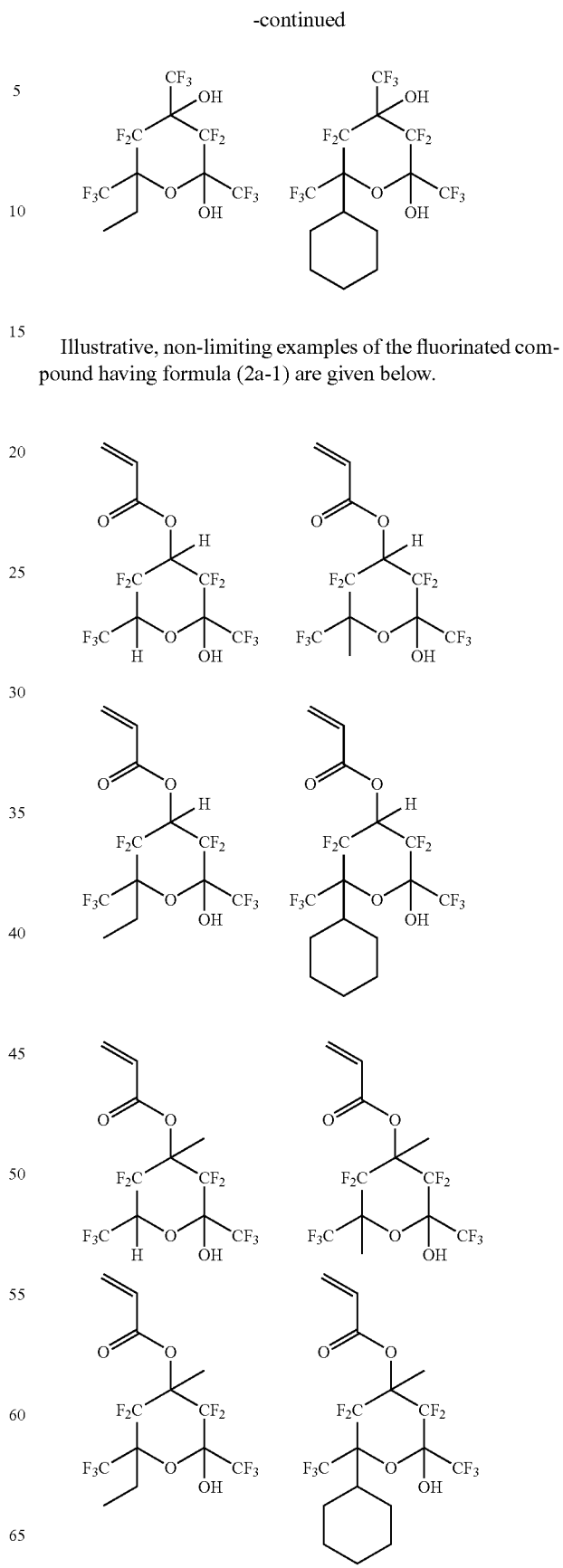
Illustrative, non-limiting examples of the fluorinated compound having formula (2a-1) are given below.

-continued
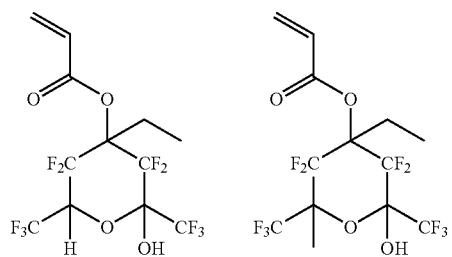
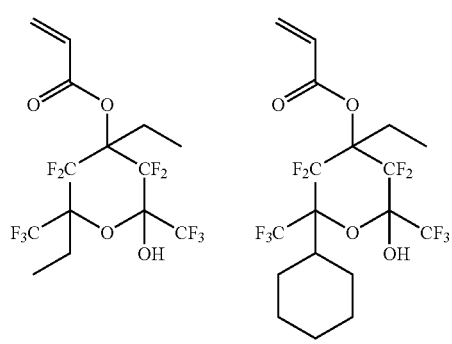
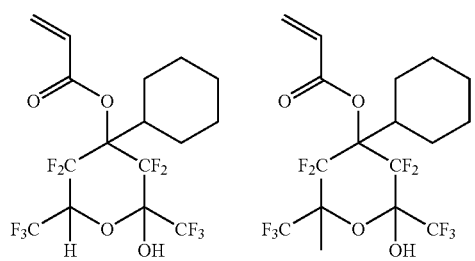
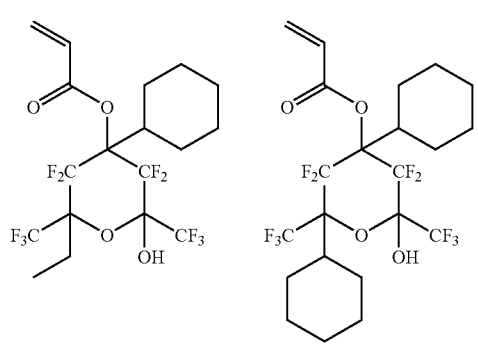
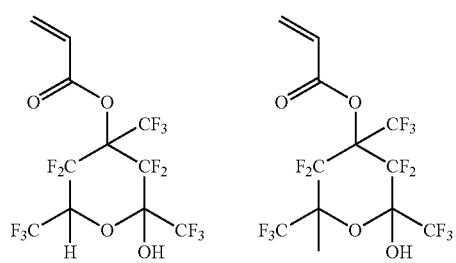
-continued
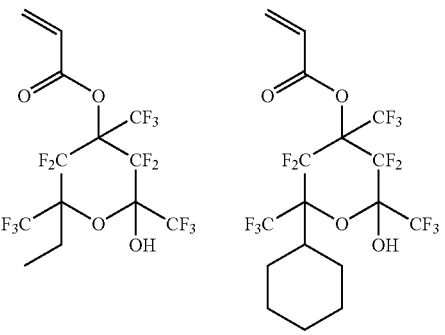
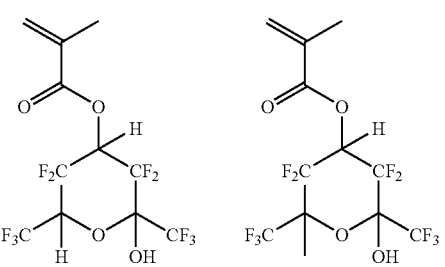
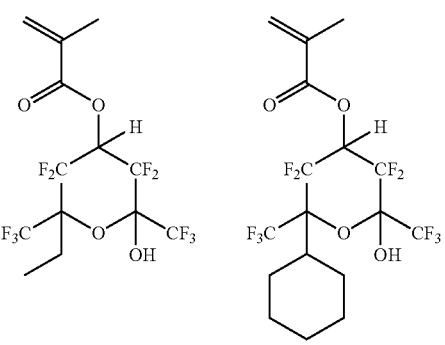
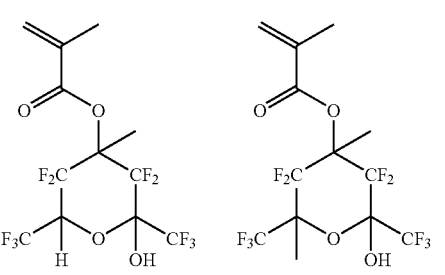
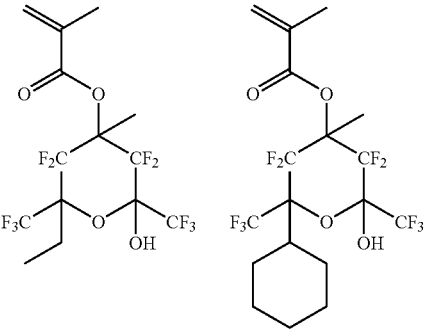

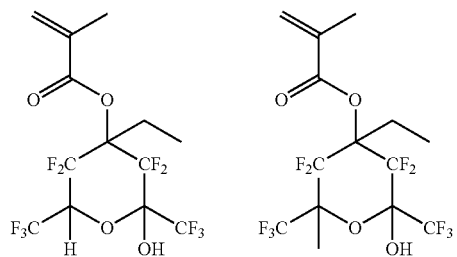
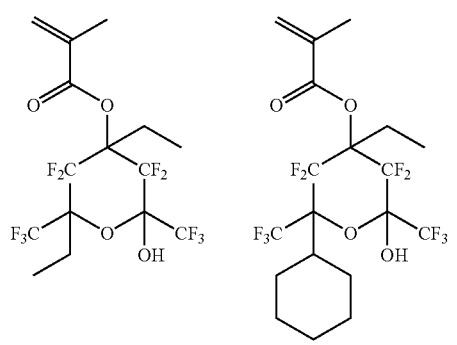
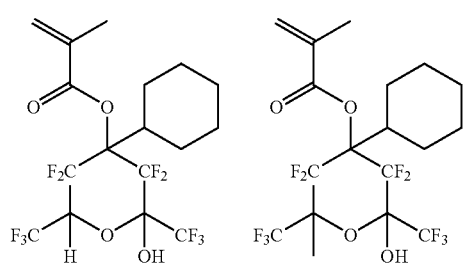
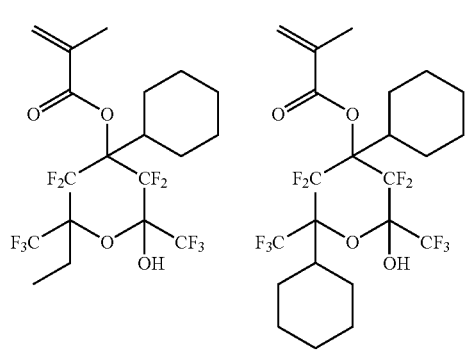
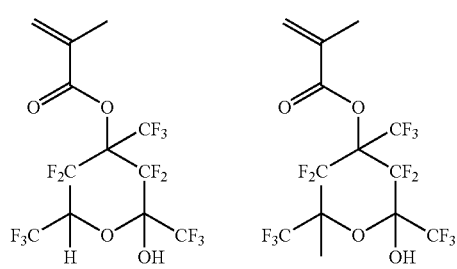
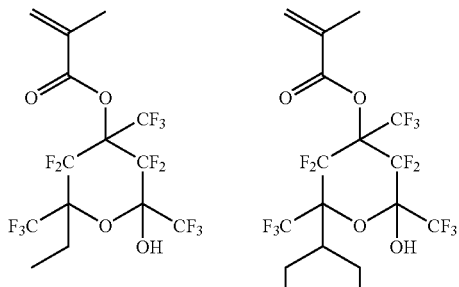
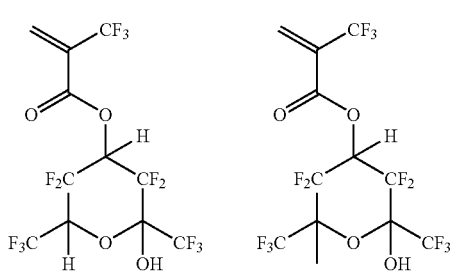
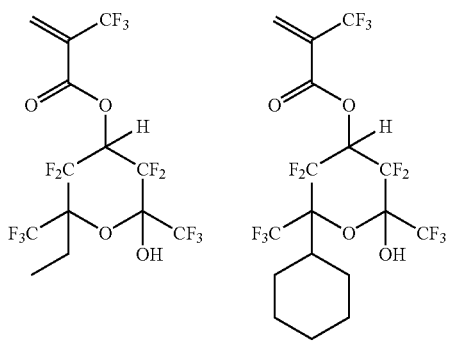
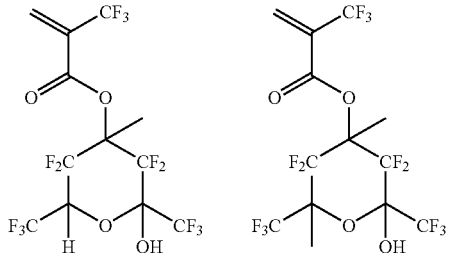
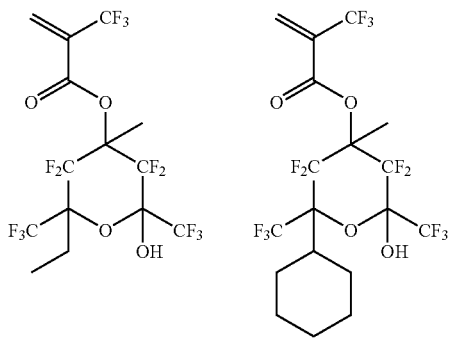

-continued
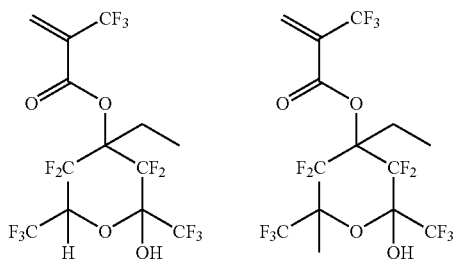
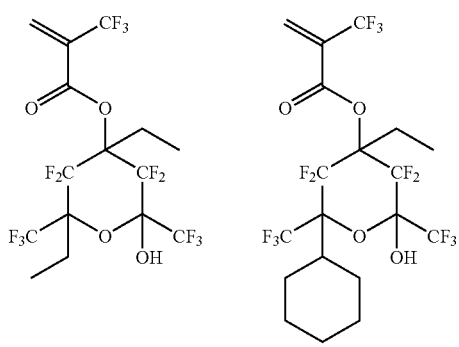
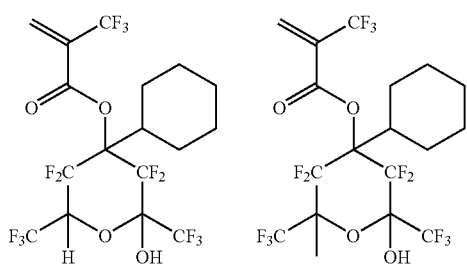
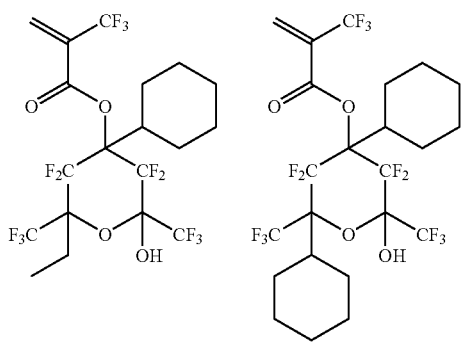
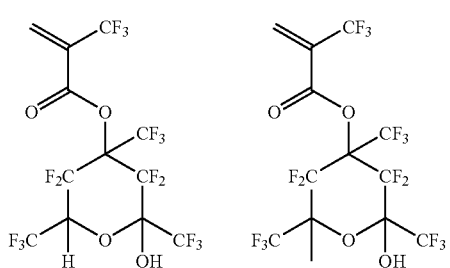
-continued
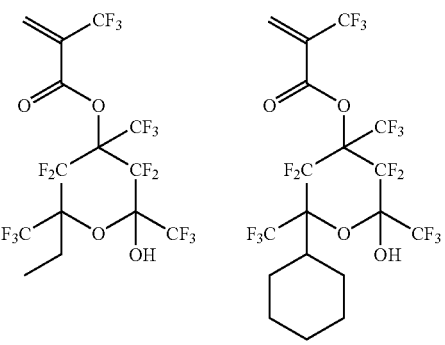
Illustrative, non-limiting examples of the fluorinated compound having formula (2b-1) are given below.
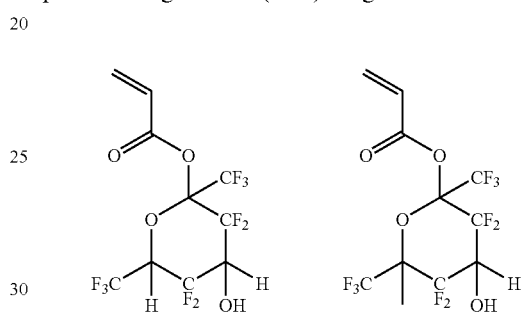
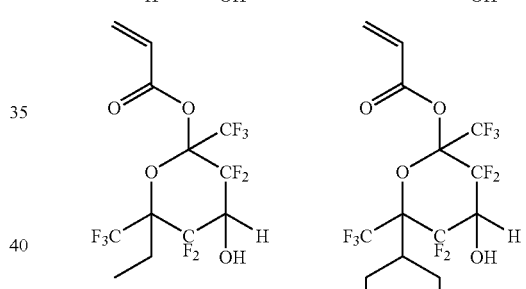
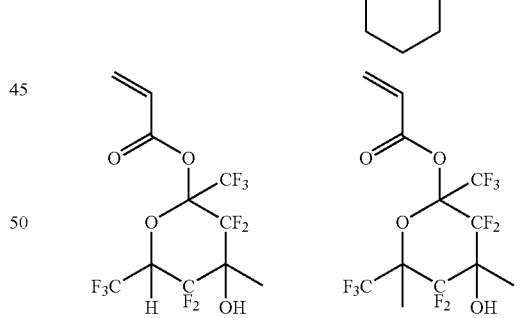
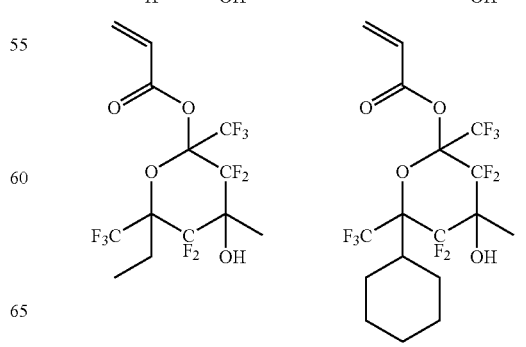

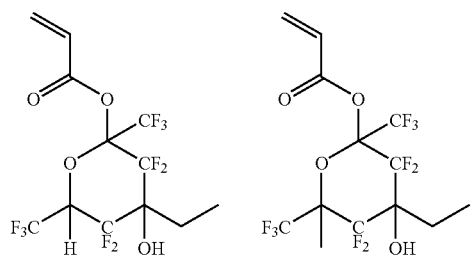
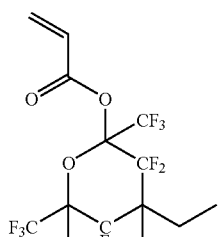
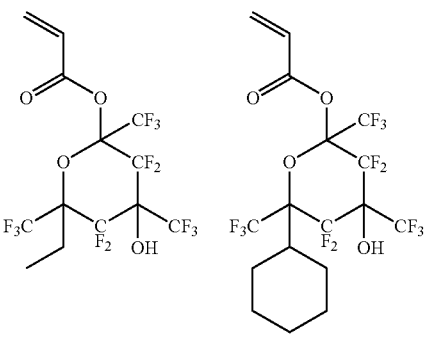
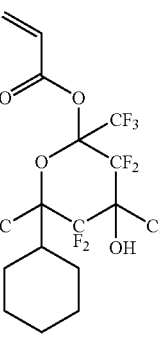
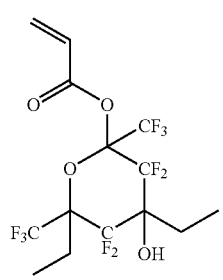
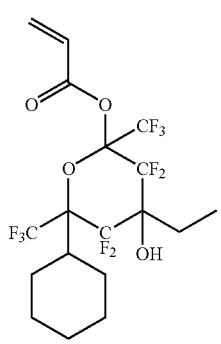
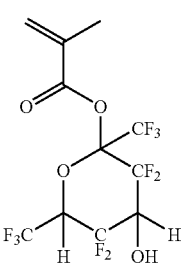
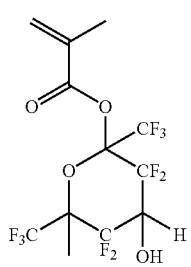
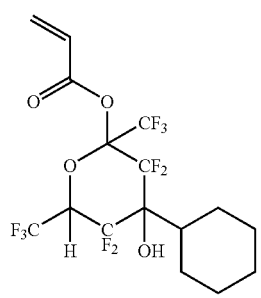
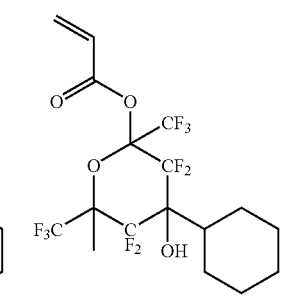
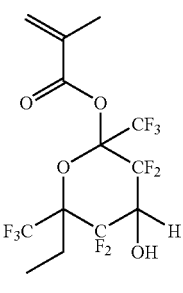
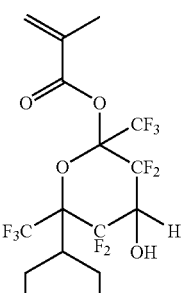
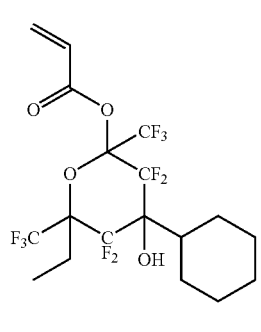
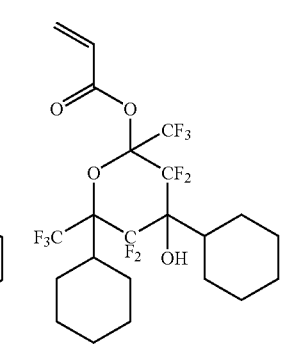
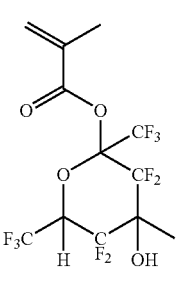
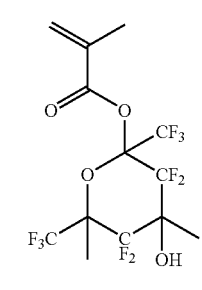
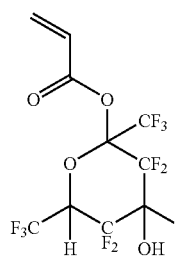
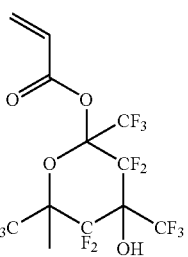
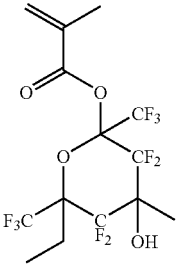
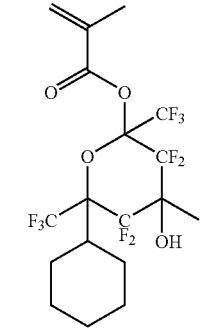

-continued
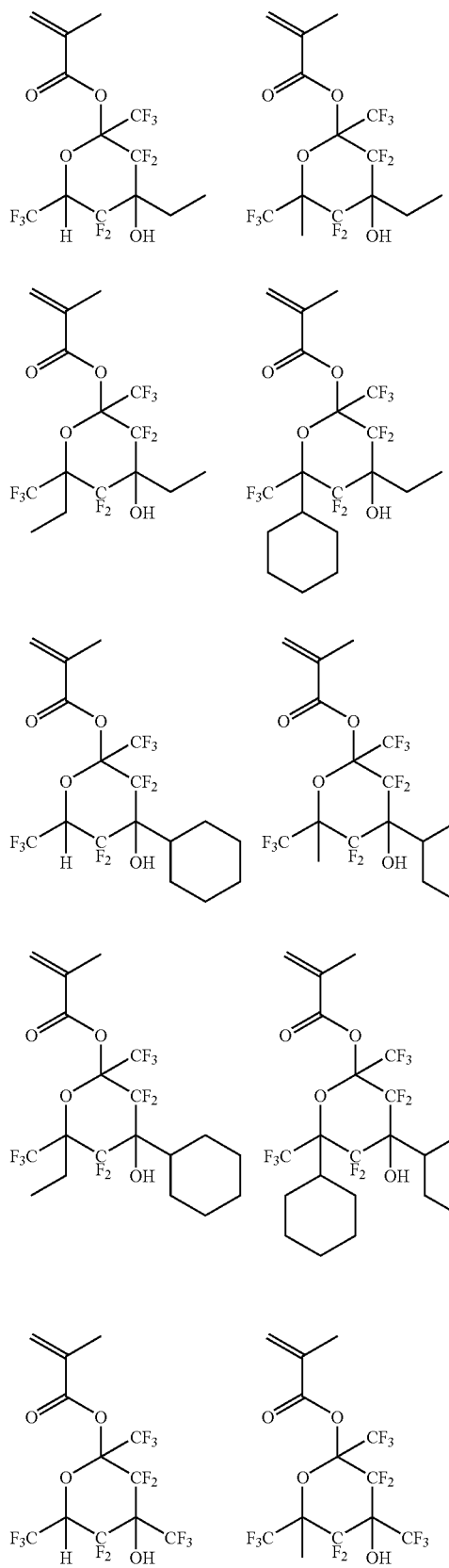
-continued
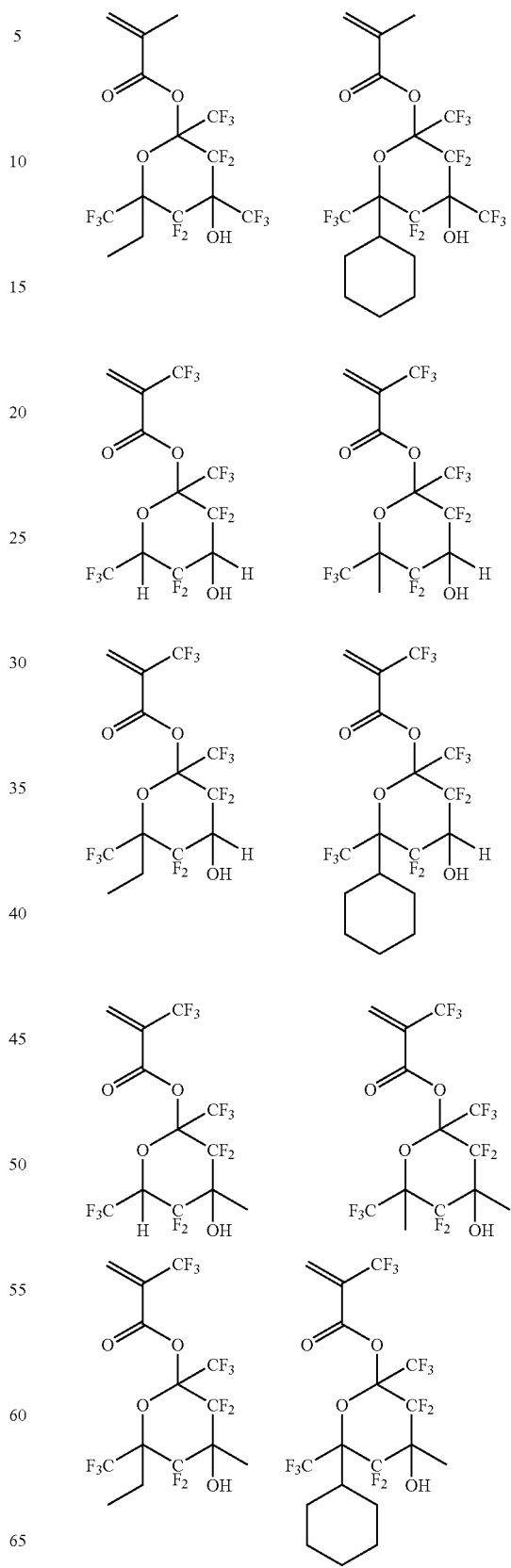

-continued

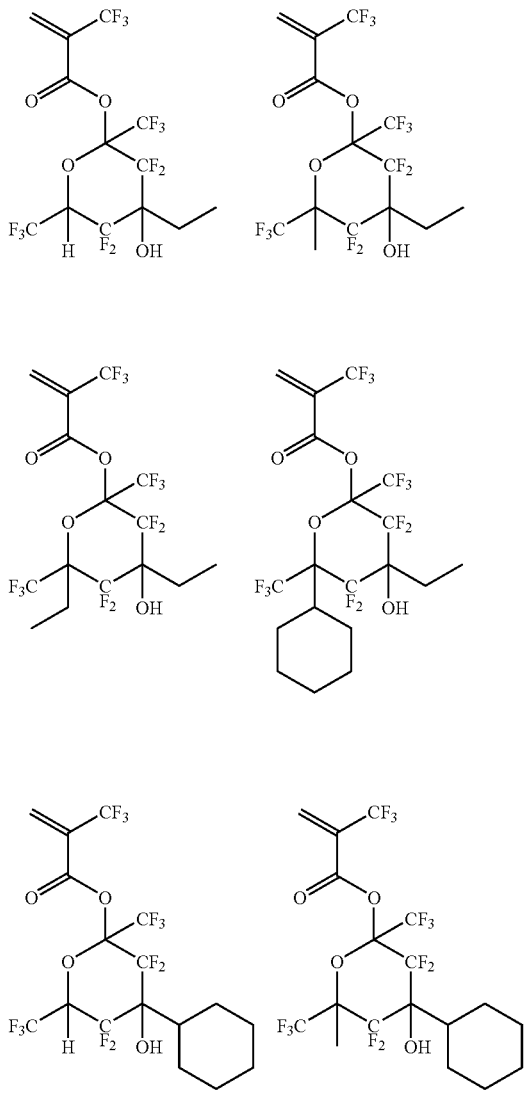

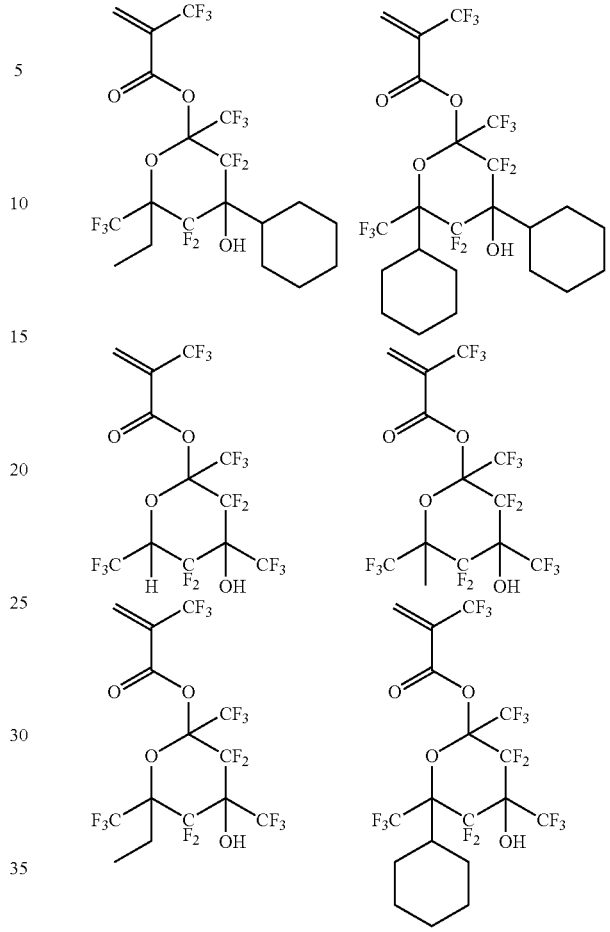

Next, methods of preparing the fluorinated compounds and polymerizable fluorinated ester compounds of the invention are described.

The method for the preparation of the novel fluorinated compound having formula (1-1) involves three stages. It is prepared by (i) reacting an ester compound $R^1CO_2R^4$ with an enolate compound having formula (3), (ii) reacting with a compound $R^2$-Z, and (iii) treating with water, as shown below.

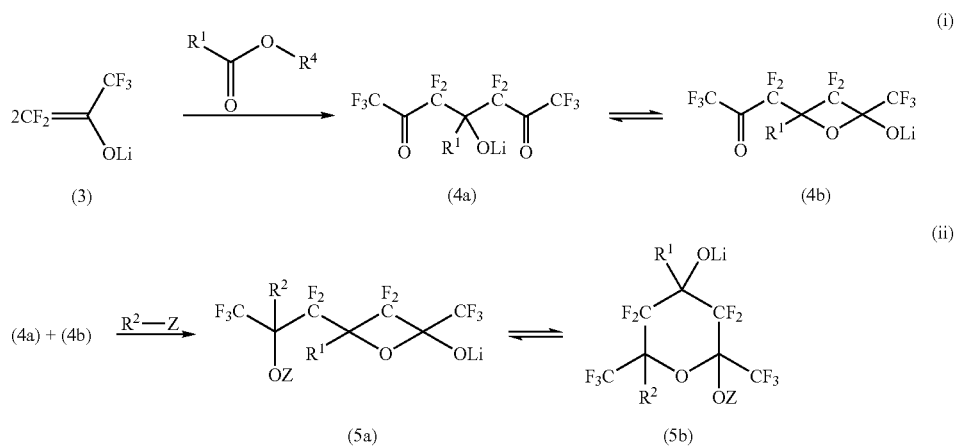

(5a) + (5b) $\xrightarrow{H_2O}$ 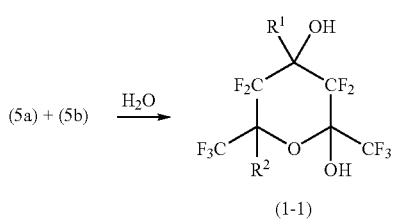

(1-1)                                                                            (iii)

Herein $R^1$ and $R^2$ each are hydrogen or a straight, branched or cyclic $C_1$-$C_{20}$ alkyl or fluoroalkyl group, $R^3$ is hydrogen, fluorine, or a $C_1$-$C_4$ alkyl or fluoroalkyl group, $R^4$ is a $C_1$-$C_{20}$ alkyl group, and Z is such a monovalent group that $R^2$-Z provides a $R^2$ anion equivalent.

With respect to the ester compound having the formula $R^1CO_2R^4$ which is the substrate in the first stage, examples of $R^1$ include hydrogen, alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopropyl, cyclobutyl, cyclopentyl, cyclohexyl, cyclopentylmethyl, cyclopentylethyl, cyclopentylbutyl, cyclohexylmethyl, cyclohexylethyl, and cyclohexylbutyl, and fluoroalkyl groups including the foregoing alkyl groups in which one or more hydrogen atoms are replaced by fluorine atoms. Examples of $R^4$ include alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopropyl, cyclobutyl, cyclopentyl, cyclohexyl, cyclopentylmethyl, cyclopentylethyl, cyclopentylbutyl, cyclohexylmethyl, cyclohexylethyl, and cyclohexylbutyl.

The enolate compound of formula (3) can be readily prepared from 1,1,1,3,3,3-hexafluoro-2-propanol (see T. Nakai et al., *Tetrahedron Letters*, Vol. 29, p. 4119, 1988 and T. Nakai et al., *Organic Syntheses*, Vol. 76, p. 151, 1998). The reactant, 1,1,1,3,3,3-hexafluoro-2-propanol has a melting point of −4° C. to −2° C. and a boiling point of 59-60° C. and is liquid at room temperature and easy to handle.

When the ester compound $R^1CO_2R^4$ is reacted with two equivalents of the enolate compound of formula (3), there is formed either one or both of a compound having formula (4a) and its intramolecular cyclization, a compound having formula (4b). It is believed that the equilibrium between compounds (4a) and (4b) in this mix system is biased toward compound (4b) for the reason that even when this mix system is reacted with a large excess of $R^2$-Z, a compound (5a) or (5b) in which only one carbonyl group has been nucleophilic attacked is produced, but a compound in which two carbonyl groups on compound (4a) have been nucleophilic attacked is not produced.

The reaction of the ester compound $R^1CO_2R^4$ with the enolate compound (3) is carried out in an organic solvent. Examples of suitable solvents include hydrocarbons such as hexane, heptane, benzene, toluene, xylene and cumene, and ethers such as dibutyl ether, diethylene glycol diethyl ether, diethylene glycol dimethyl ether, tetrahydrofuran and 1,4-dioxane, alone or in admixture of any. The reaction temperature is typically from −50° C. to approximately the boiling point of the solvent, preferably from −20° C. to 100° C. It is desired for higher yields that the reaction time is determined by monitoring the progress of reaction by thin-layer chromatography (TLC) or gas chromatography (GC). The reaction time is usually about 0.1 hour to about 50 hours.

In the second stage, the compound $R^2$-Z is admixed in the reaction system from the first stage. $R^2$-Z represents a $R^4$ anion equivalent and is suitably selected depending on the desired type of $R^2$. Examples of $R^2$-Z include water (wherein $R^2$ is hydrogen and Z is hydroxyl), alkyl metals (wherein $R^2$ is an alkyl group) such as methyllithium, butyllithium, phenyllithium, methylmagnesium chloride, ethylmagnesium chloride, and phenylmagnesium chloride, metal hydrides (wherein $R^2$ is a hydrogen atom) such as sodium hydride, potassium hydride, calcium hydride, aluminum hydride, borane, and diisobutylaluminum hydride, and metal hydrogen complexes or alkyl and alkoxy derivatives thereof (wherein $R^2$ is a hydrogen atom) such as sodium boron hydride and lithium aluminum hydride. An appropriate amount of $R^2$-Z used is from 1 mole to a large excess per mole of the compound (4b). When the reaction is effected in a solvent, a suitable solvent is selected from among hydrocarbons such as hexane, heptane, benzene, toluene, xylene and cumene, and ethers such as dibutyl ether, diethylene glycol diethyl ether, diethylene glycol dimethyl ether, tetrahydrofuran and 1,4-dioxane, alone or in admixture of any. The reaction temperature may be selected appropriate for a particular type of $R^2$-Z and is typically from −50° C. to approximately the boiling point of the solvent, preferably from −20° C. to 100° C. It is desired for higher yields that the reaction time is determined by monitoring the progress of reaction by TLC or GC. The reaction time is usually about 0.1 hour to about 50 hours.

In the third stage, the mix system from the second stage is subjected to conventional aqueous post-treatment. While there may be available a 4-membered ring compound corresponding to the compound (5a) and a 6-membered ring compound corresponding to the compound (5b), the compound (1-1) having a stable 6-membered ring structure is preferentially obtained under ordinary reaction conditions. If necessary, the compound (1-1) can be purified by any conventional technique such as recrystallization, chromatography or distillation.

The resulting compound (1-1) may then be transferred to acylation reaction or other applications, described later, where one or both of hydroxyl groups on the compound (1-1) are protected or blocked with a protective group or groups. To this end, acid labile groups similar to the aforementioned groups of formulae (AL-1) to (AL-3) or other protective groups may be employed. Suitable other protective groups include acyl groups such as formyl, benzoylformyl, acetyl, chloroacetyl, dichloroacetyl, trichloroacetyl, trifluoroacetyl, methoxyacetyl, triphenylmethoxyacetyl, phenoxyacetyl, phenylacetyl, nicotinyl, 3-phenylpropionyl, 4-pentenoyl, 4-oxopentanoyl, pivaloyl, 1-adamantoyl, crotonyl, 4-methoxycrotonyl, benzoyl, 4-phenylbenzoyl, and mesitoyl.

The blocking and deblocking reactions of hydroxyl group widely vary with the type of protective group and may be carried out in a conventional manner. In an example of blocking with an acyl group, a well-known esterification technique can be used. For deblocking of the acyl group, there may be employed hydrolysis with the aid of acid or base, solvolysis, elimination reaction under acidic conditions or the like.

In the structures having formulae (1), (4a), (4b), (5a) and (5b) wherein the hydroxyl group may be blocked with a protective group, there can be present enantiomers or diastereomers which are associated with an asymmetric carbon atom or ring structure. The general formula collectively represents all such stereoisomers. The stereoisomers may be used alone or in admixture.

The polymerizable fluorinated ester compound of the invention can be prepared by acylating the compound (1) wherein one or both of R are hydrogen or the compound (1-1). Particularly in the acylation reaction of the compound (1-1), the regio-selectivity of reaction is a problem since the compound (1-1) has two hydroxyl groups which can be potentially acylated. That is, there can be produced two position isomers having the general formulae (2a-1) and (2b-1).

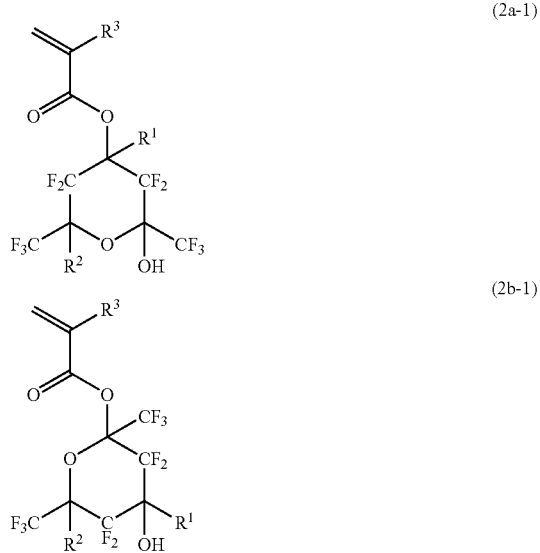

Herein $R^1$ and $R^2$ each are hydrogen or a straight, branched or cyclic $C_1$-$C_{20}$ alkyl or fluoroalkyl group, and $R^3$ is hydrogen, fluorine, or a $C_1$-$C_4$ alkyl or fluoroalkyl group.

In this reaction, when the two hydroxyl groups on the compound (1-1) are definitely distinguished in steric hindrance or when the two hydroxyl groups have different acidity, the compound (2a-1) or (2b-1) may be selectively obtained by properly controlling the reaction conditions. In these cases, the compound (1-1) can be used as the reaction substrate without any treatment, i.e., without blocking any hydroxyl group, and subjected to acylation reaction to be described later. This process is of great commercial worth due to shorter or fewer steps involved, as compared with the process requiring blocking and deblocking steps to be described later.

For the acylation reaction, well-known esterification methods, such as reaction with acylating agents, reaction with carboxylic acids and transesterification are applicable.

In the reaction using acylating agents, the compound (1-1) is mixed with a solvent, and an acylating agent and a base are sequentially or simultaneously fed thereto whereupon reaction takes place. Examples of the acylating agent include acid halides such as acrylic chloride, methacrylic chloride, acrylic bromide, methacrylic bromide, α-fluoroacrylic chloride, and α-trifluoromethylacrylic chloride, and acid anhydrides such as acrylic anhydride, methacrylic anhydride, α-fluoroacrylic anhydride, α-trifluoromethylacrylic anhydride, acrylic acid/trifluoroacetic acid mixed acid anhydride, methacrylic acid/trifluoroacetic acid mixed acid anhydride, α-trifluoromethylacrylic acid/trifluoroacetic acid mixed acid anhydride, acrylic acid/p-nitrobenzoic acid mixed acid anhydride, methacrylic acid/p-nitrobenzoic acid mixed acid anhydride, ethyl acrylate/carbonic acid mixed acid anhydride, and ethyl methacrylate/carbonic acid mixed acid anhydride. Examples of the solvent used herein include chlorinated solvents such as methylene chloride, chloroform and trichloroethylene, hydrocarbons such as hexane, heptane, benzene, toluene, xylene and cumene, ethers such as dibutyl ether, diethylene glycol diethyl ether diethylene glycol dimethyl ether, tetrahydrofuran, and 1,4-dioxane, nitriles such as acetonitrile, ketones such as acetone and 2-butanone, esters such as ethyl acetate and n-butyl acetate, and aprotic polar solvents such as N,N-dimethylformamide, dimethyl sulfoxide, and hexamethylphosphoric triamide, alone or in admixture of any. Examples of the base include triethylamine, diisopropylethylamine, N,N-dimethylaniline, pyridine, and 4-dimethylaminopyridine. An appropriate reaction temperature may be selected depending on the type of acylating agent used and other reaction conditions. The reaction temperature is typically from −50° C. to approximately the boiling point of the solvent, preferably from −20° C. to room temperature. An appropriate amount of the acylating agent used is from 1 to 40 moles, more preferably 1 to 5 moles per mole of the compound (1-1), though it depends on the structure of the agent.

The acylating reaction with carboxylic acids is a dehydrating reaction from a corresponding carboxylic acid, i.e., any of acrylic acid, methacrylic acid and α-trifluoromethylacrylic acid and the reactant, compound (1-1), which is generally performed in the presence of an acid catalyst. An appropriate amount of carboxylic acid used is 1 to 40 moles, more preferably 1 to 5 moles per mole of the compound (1-1), though it depends on the structure of acid. Examples of the acid catalyst include inorganic acids such as hydrochloric acid, hydrobromic acid, sulfuric acid, and nitric acid, and organic acids such as oxalic acid, trifluoroacetic acid, methanesulfonic acid, benzenesulfonic acid, and p-toluenesulfonic acid, alone or in admixture of any. An appropriate amount of the acid catalyst used is 0.001 to 1 mole, more preferably 0.01 to 0.05 mole per mole of the compound (1-1). Examples of the solvent used are as exemplified above for the reaction with the acylating agent. The reaction temperature is preferably from −50° C. to approximately the boiling point of the solvent although it depends on the type of carboxylic acid used and other reaction conditions. The reaction may also be performed in a solvent comprising a hydrocarbon such as hexane, heptane, benzene, toluene, xylene or cumene, by heating the system around the boiling point of the solvent, while azeotroping the formed water out of the system. In this embodiment, the water may be distilled off by reflux heating under atmospheric pressure, or the water be distilled off at a lower temperature than the boiling point and reduced pressure.

The transesterification is implemented by reacting the reactant, compound (1-1) with a corresponding carboxylic acid ester, i.e., any of acrylate, methacrylate and α-trifluoromethylacrylate in the presence of a catalyst and removing the alcohol formed. The carboxylic acid esters used are preferably primary alkyl esters. Inter alia, methyl, ethyl and n-propyl esters are preferred because of low cost and smooth progress of reaction. An appropriate amount of carboxylic acid ester used is 1 to 40 moles, more preferably 1 to 5 moles per mole of the compound (1-1), though it depends on the structure of ester. Examples of the catalyst include inorganic acids such as hydrochloric acid, hydrobromic acid, sulfuric acid, and nitric acid, organic acids such as oxalic acid, trifluoroacetic acid, methanesulfonic acid, benzenesulfonic acid, and p-toluenesulfonic acid, bases such as sodium methoxide, sodium ethoxide, potassium t-butoxide, and 4-dimethylaminopyridine, and salts such as sodium cyanide, potassium cyanide, sodium acetate, potassium acetate, calcium acetate, tin acetate, aluminum acetate, aluminum acetoacetate, alumina, and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide, and titanium(IV) oxide, alone or in admixture of any. An appropriate amount of the catalyst used is 0.001 to 20 moles, more preferably 0.01 to 0.05 mole per mole of the compound (1-1). The reaction may be performed in a solventless system (the reagent, carboxylic acid ester itself may serve as a solvent), which is preferred in that extra operations such as concentration and solvent recovery are eliminated. A solvent may be used in a supplemental manner for the purpose of preventing polymerization of the target compound and reagent. Examples of the solvent, if used, include hydrocarbons such as hexane, heptane, benzene, toluene, xylene and cumene, and ethers such as dibutyl ether, diethylene glycol diethyl ether, diethylene glycol dimethyl ether, tetrahydrofuran, and 1,4-dioxane, alone or in admixture. An appropriate reaction temperature may be selected depending on the type of carboxylic acid ester used and other reaction conditions. Usually, the reaction is performed at elevated temperature. Better results are obtained when the reaction is performed at a temperature approximate to the boiling point of a low boiling point alcohol formed by transesterification reaction such as methanol, ethanol or 1-propanol, whereby the alcohol formed is distilled off during the reaction. The alcohol may be distilled off at a lower temperature than the boiling point and reduced pressure.

The resulting compounds (2a-1) and (2b-1) may be protected by blocking the hydroxyl group with a protective group as in the case of compound (1-1). The protective group used herein may be the same as the above-listed groups, and the blocking and deblocking reactions of hydroxyl group may be performed in the same manner as in the above-described embodiment.

It is desired for higher yields that the time of acylating reaction (inclusive of blocking reaction of hydroxyl group) is determined by monitoring the progress of reaction by GC or TLC. The reaction time is usually about 0.1 hour to about 240 hours. After the completion of reaction, the target fluorinated ester compound (2a) or (2b) is recovered from the reaction mixture by a conventional post-treatment such as aqueous work-up or concentration. If necessary, the compound (2a) or (2b) can be purified by any conventional technique such as recrystallization, chromatography or distillation.

In the structures having formulae (2a) and (2b) wherein the hydroxyl group may be blocked with a protective group, there can be present enantiomers or diastereomers which are associated with an asymmetric carbon atom or ring structure. The general formula collectively represents all such stereoisomers. The stereoisomers may be used alone or in admixture.

Polymer

Next, the polymers or high molecular weight compounds of the invention are described.

The polymers of the invention are obtained through polymerization reaction of the polymerizable fluorinated ester compounds (2a) or (2b) or compounds in which the hydroxyl group is blocked with a protective group. The olymers of the invention are thus defined as comprising recurring units having the general formula (2a') or (2b'), and more specifically the general formula (2a'-1) or (2b'-1) or the structure in which the hydroxyl group is blocked with a protective group.

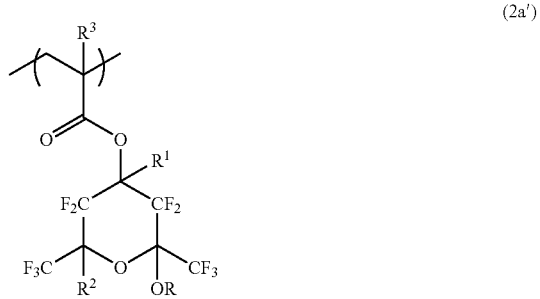

(2a')

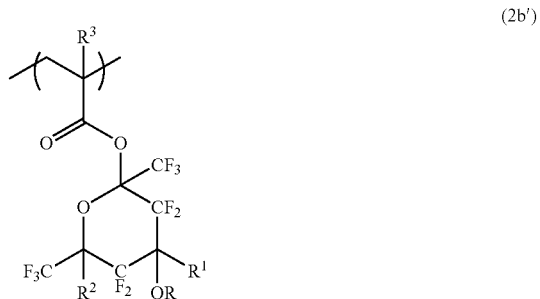

(2b')

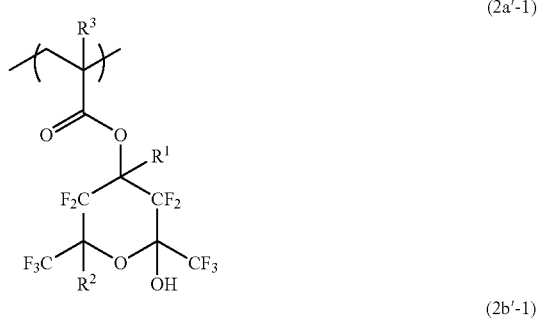

(2a'-1)

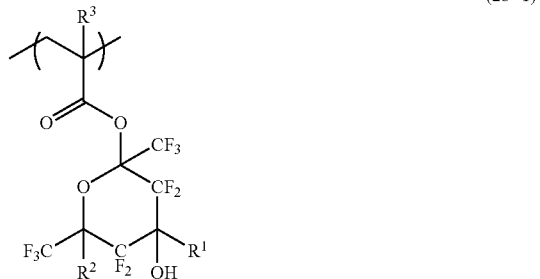

(2b'-1)

Herein $R^1$ and $R^2$ each are hydrogen or a straight, branched or cyclic $C_1$-$C_{20}$ alkyl or fluoroalkyl group, $R^3$ is hydrogen, fluorine, or a $C_1$-$C_4$ alkyl or fluoroalkyl group, and R is hydrogen or a protective group.

$R^1$ to $R^3$, and R representative of a protective group for hydroxyl group are the same as described for the compounds (1), (2a) and (2b).

Illustrative, non-limiting examples of the recurring units having formula (2a'-1) are given below.

-continued
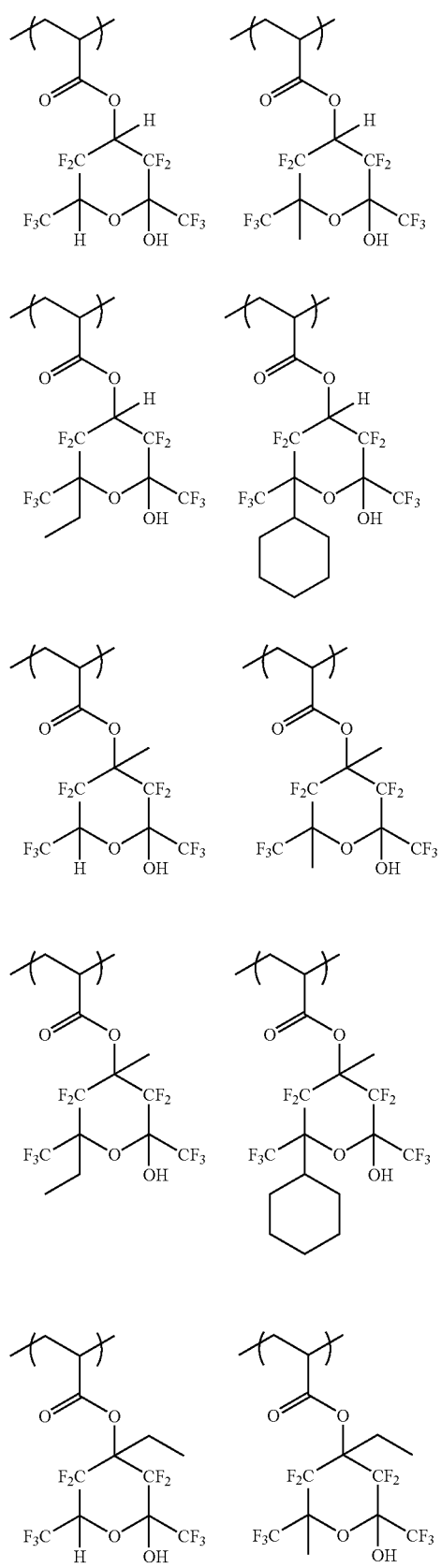
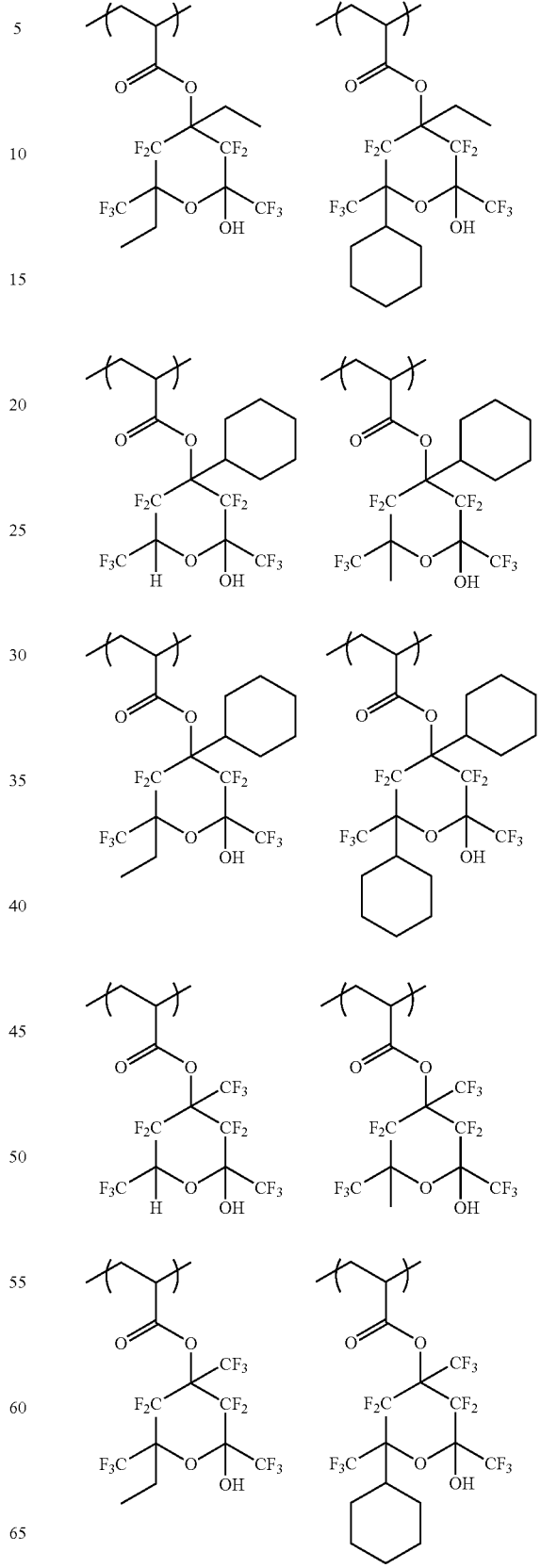

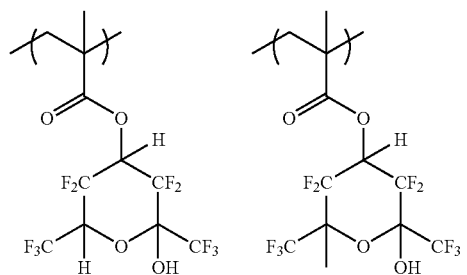
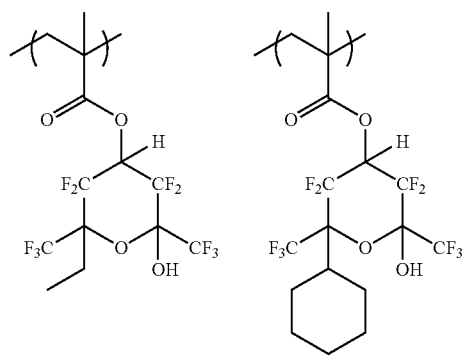
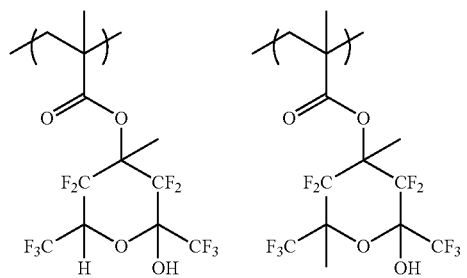
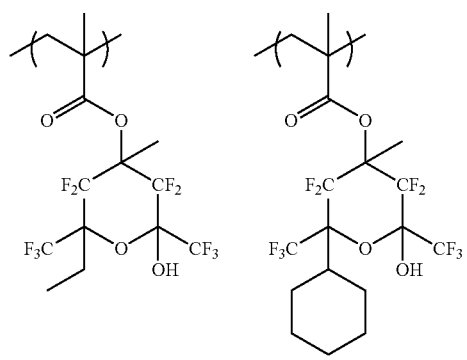
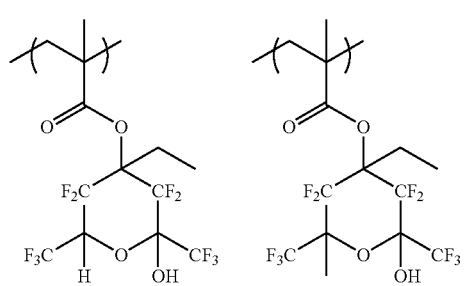
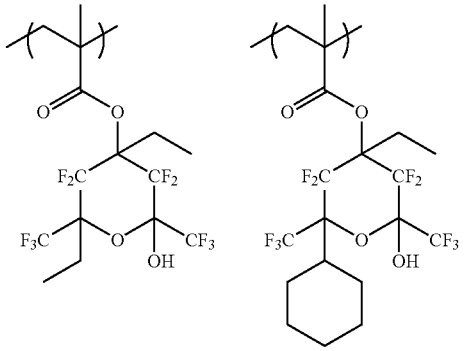
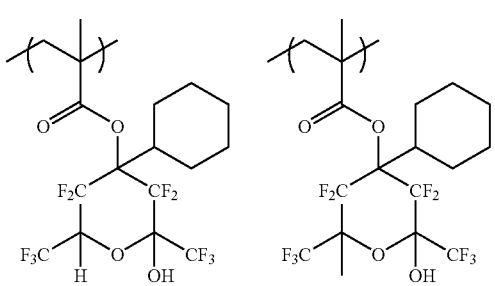
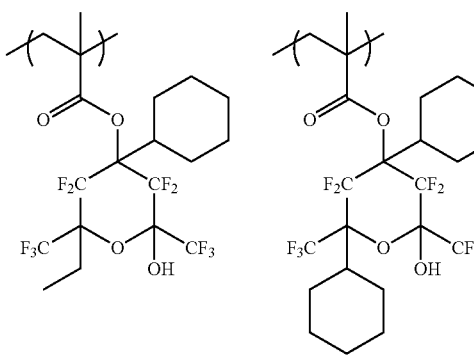
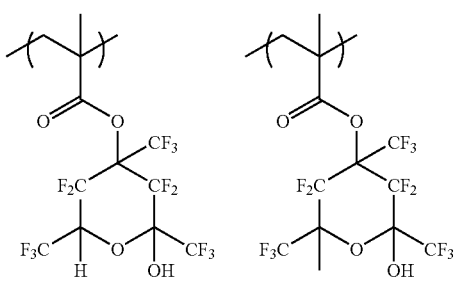
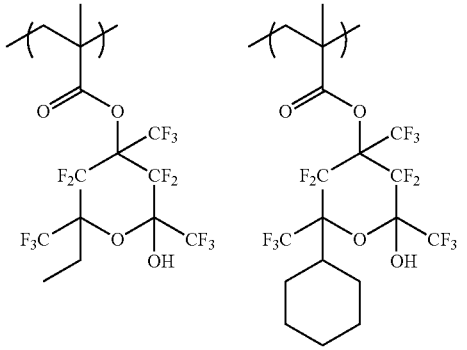

-continued
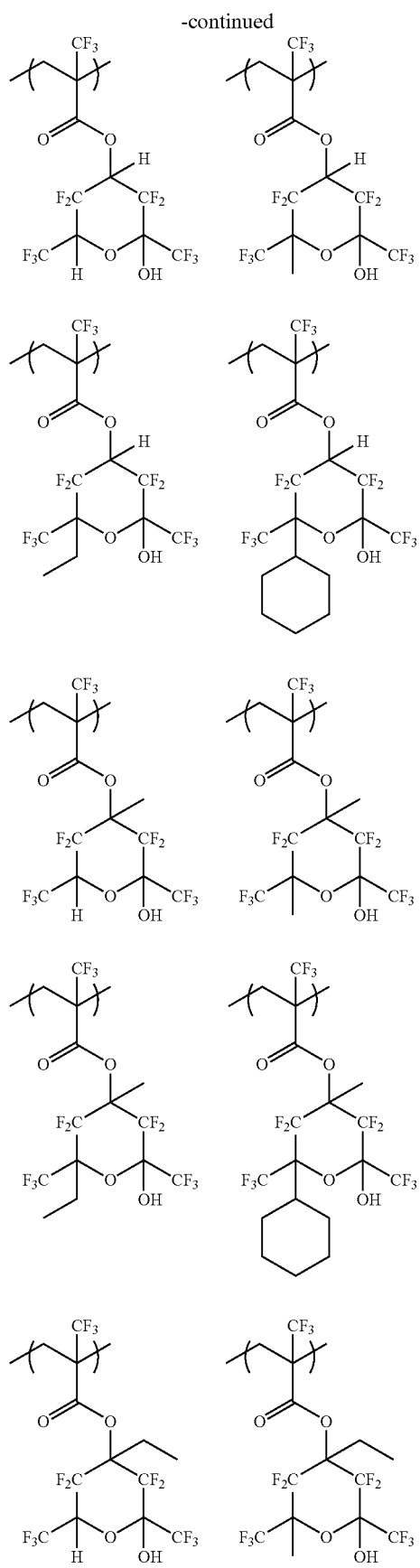
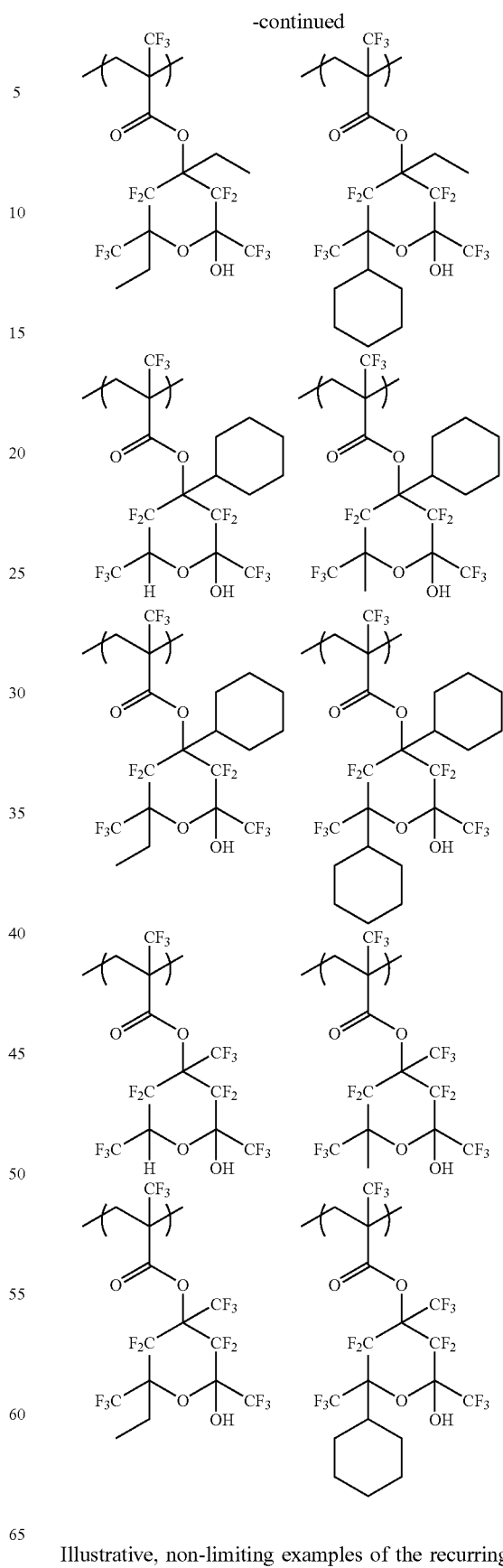
Illustrative, non-limiting examples of the recurring units having formula (2b'-1) are given below.

-continued
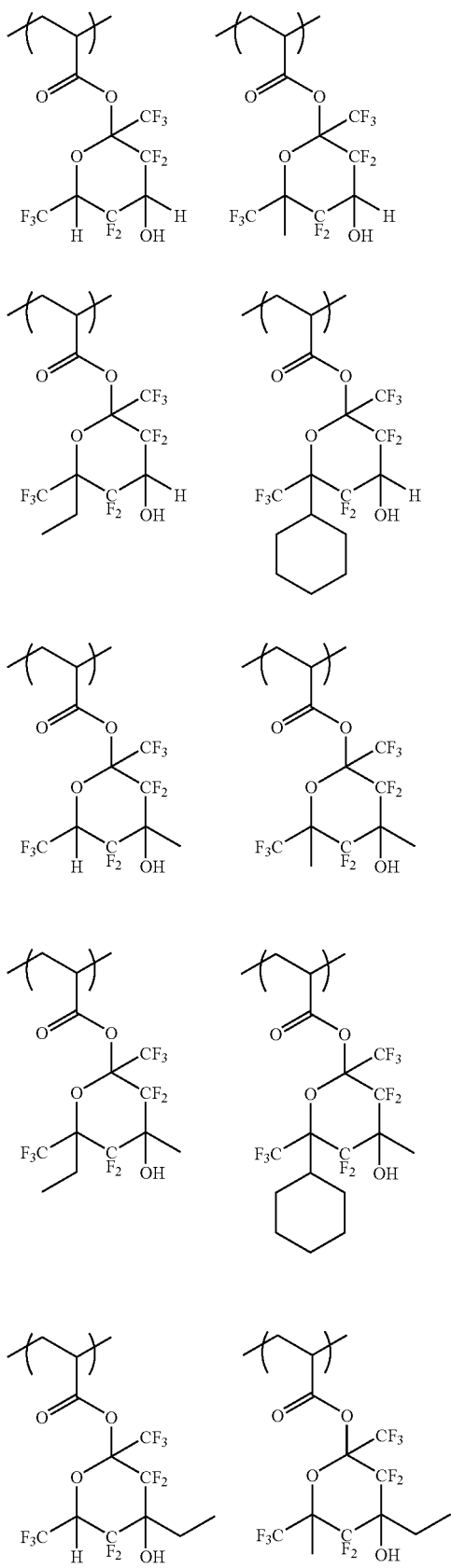
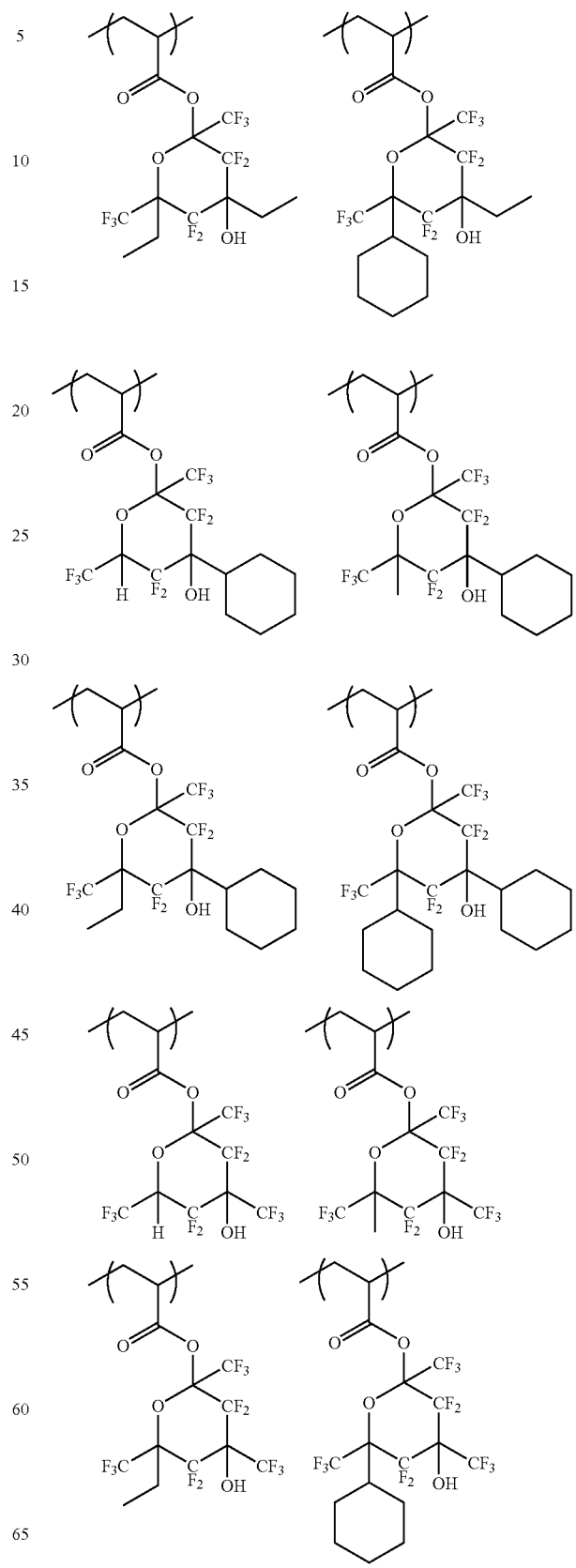

-continued
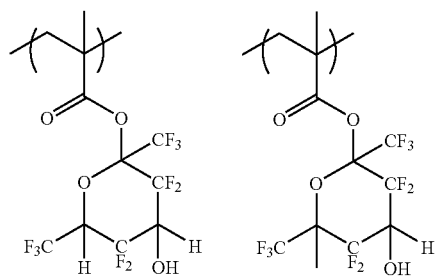
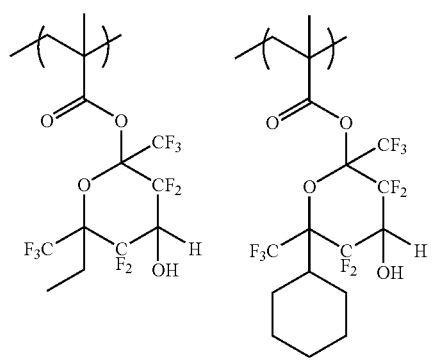
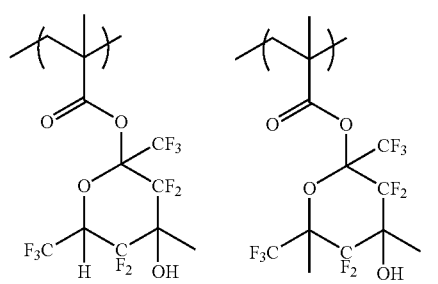
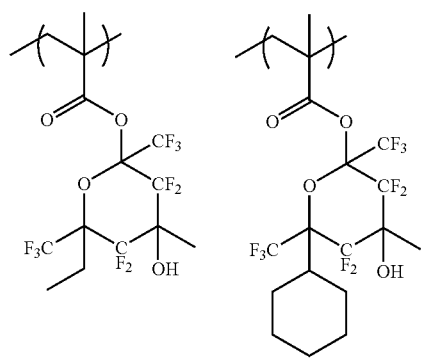
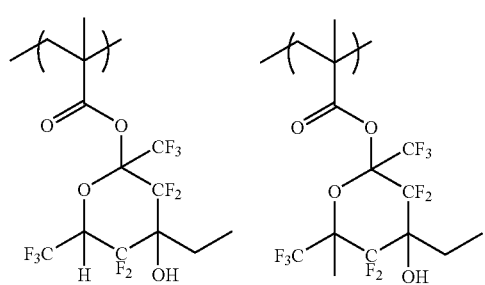
-continued
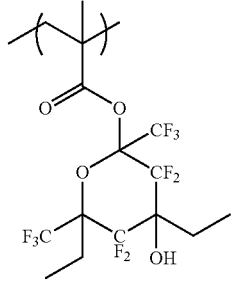
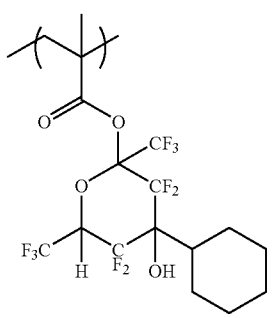
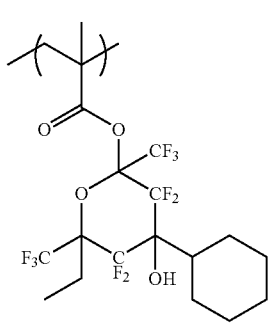
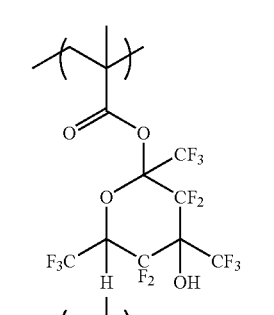
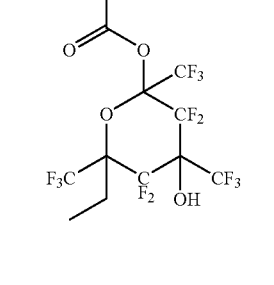

-continued
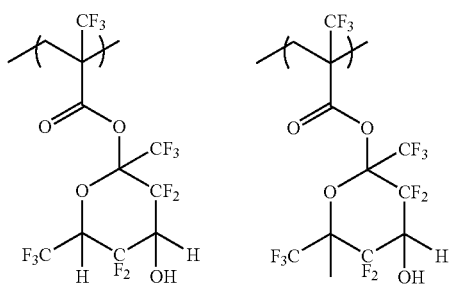
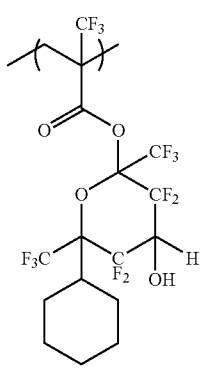
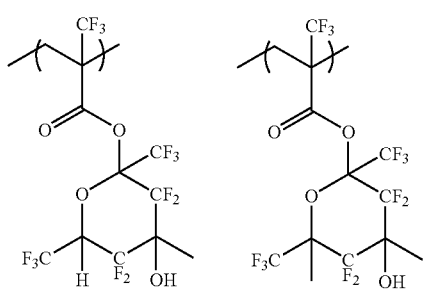
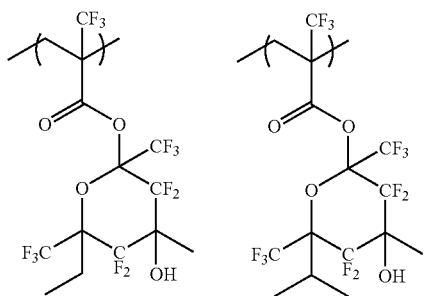
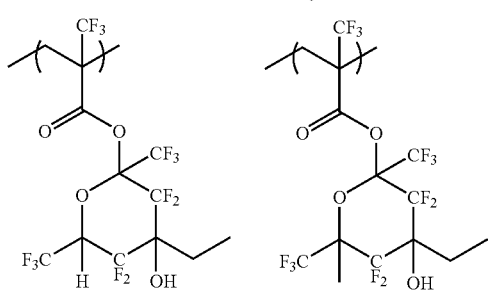
-continued
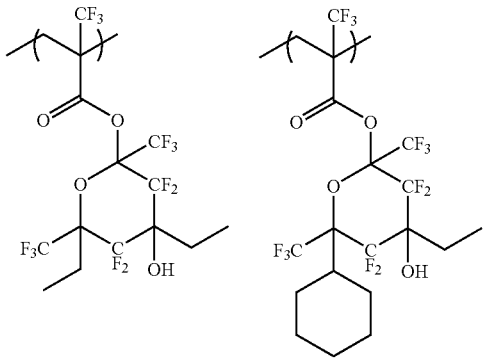
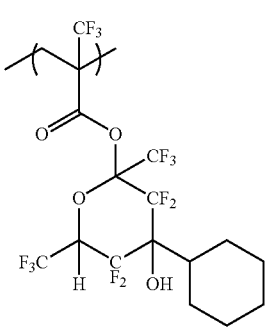
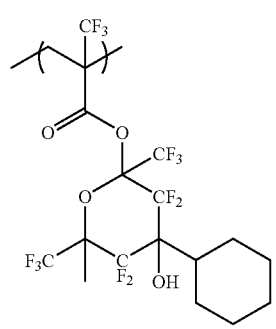
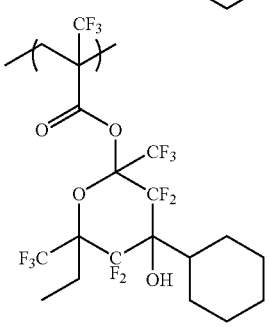
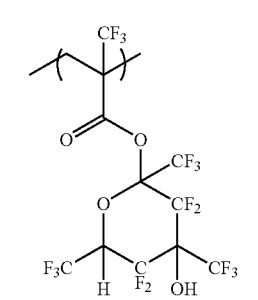
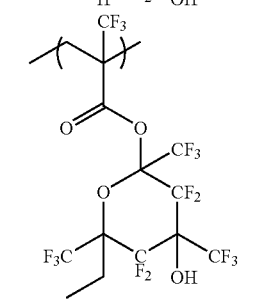
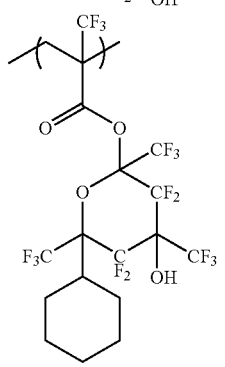

In one embodiment, the polymer of the invention is used as a base polymer in positive resist compositions. In such an embodiment, by effecting copolymerization reaction between the compound (2a) or (2b) and any of compounds having the general formula (6) to (8), recurring units having formulae (6') to (8') may be incorporated into the polymer in addition to the recurring units having formula (2a') or (2b').

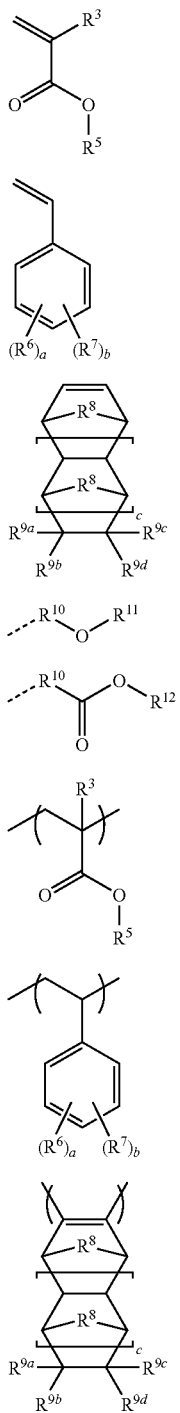

Herein, $R^3$ is hydrogen, fluorine, or a $C_1$-$C_4$ alkyl or fluoroalkyl group. $R^5$ is hydrogen, an acid labile group, an adhesive group, or a straight, branched or cyclic $C_1$-$C_{20}$ alkyl or fluoroalkyl group. $R^6$ is fluorine or a straight, branched or cyclic $C_1$-$C_{20}$ fluoroalkyl group. $R^7$ is a substituent group having formula (9-1). $R^8$ is a methylene group, oxygen atom or sulfur atom. $R^{9a}$ to $R^{9d}$ each are hydrogen, fluorine, a straight, branched or cyclic $C_1$-$C_{20}$ alkyl or fluoroalkyl group, or a substituent group having formula (9-1) or (9-1), with the proviso that at least one of $R^{9a}$ to $R^{9d}$ contains a substituent group having formula (9-1) or (9-2). $R^{10}$ is a single bond or a straight, branched or cyclic $C_1$-$C_{20}$ alkylene or fluoroalkylene group. $R^{11}$ and $R^{12}$ each are hydrogen, an acid labile group, an adhesive group, or a straight, branched or cyclic $C_1$-$C_{20}$ alkyl or fluoroalkyl group. The subscript a is an integer of 0 to 4, b is 1 or 2, satisfying $1 \leq a+b \leq 5$, and c is 0 or 1. In formulae (9-1) and (9-2), a broken line denotes a valence bond.

The groups of $R^3$ are as described for the compounds (2a) and (2b).

The acid labile groups of $R^5$, $R^{11}$ and $R^{12}$ are the same as the protective groups described for the compounds (1), (2a) and (2b).

The adhesive groups of $R^5$, $R^{11}$ and $R^{12}$ are selected from a variety of such groups and preferably groups of the following formulae.

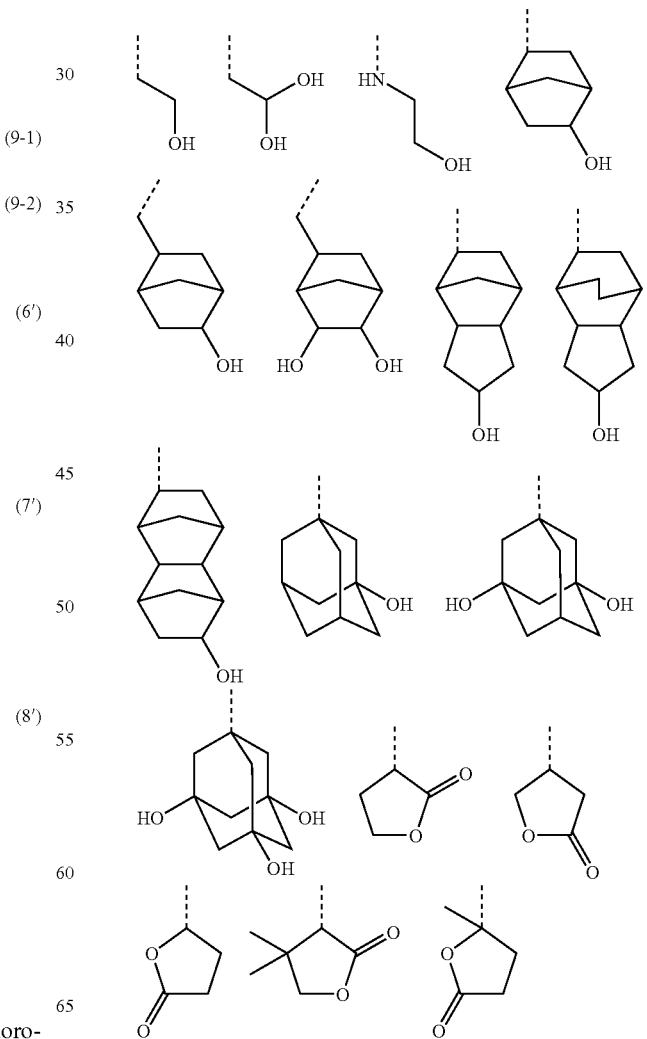

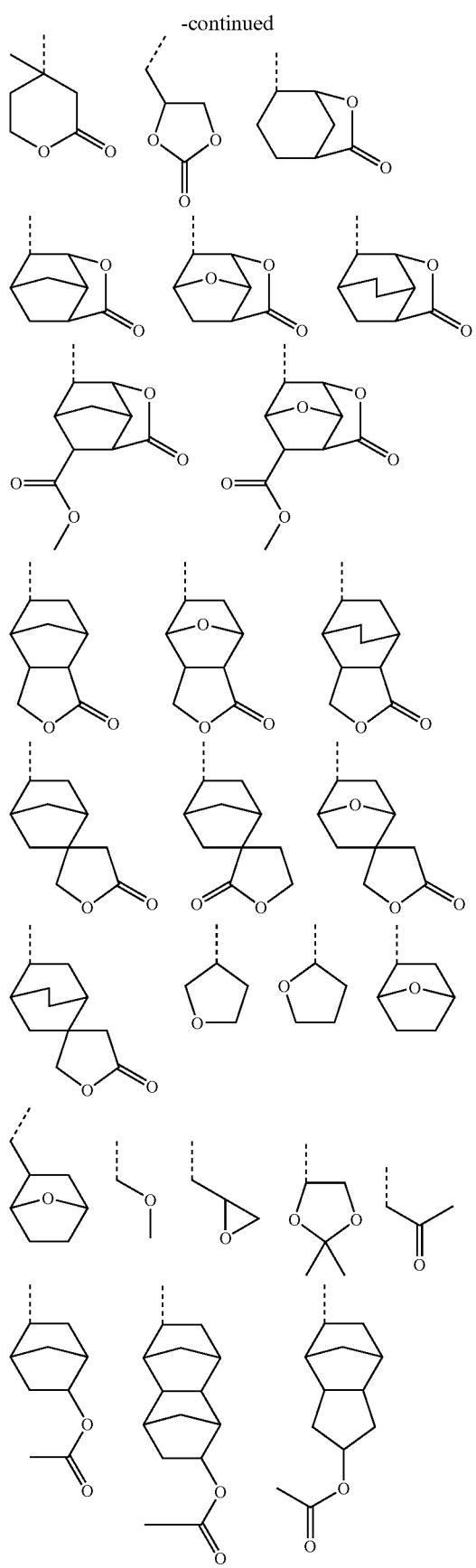
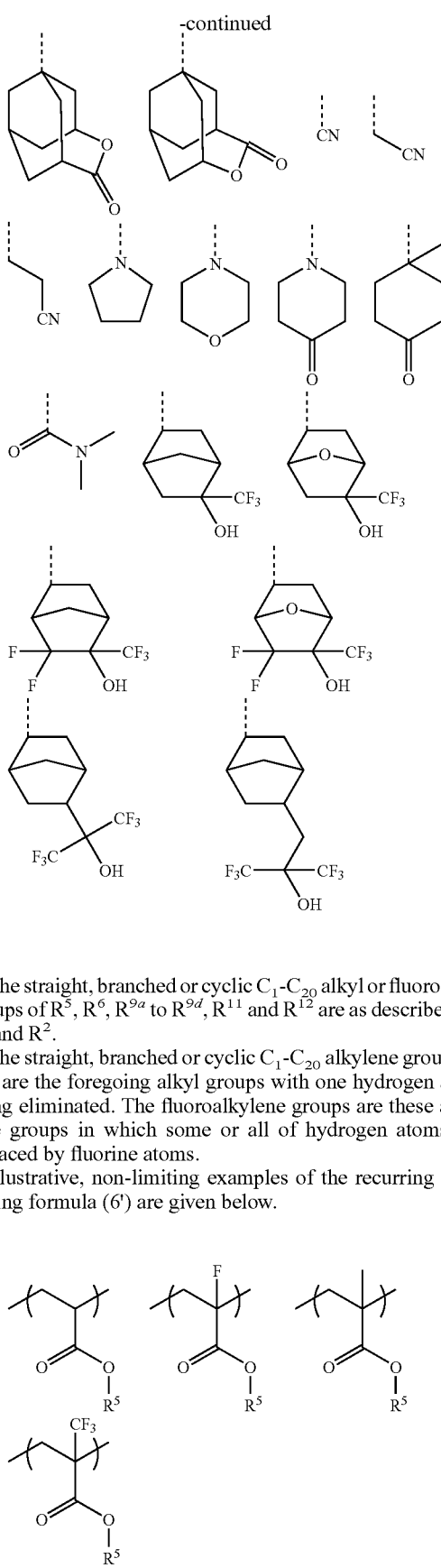

The straight, branched or cyclic $C_1$-$C_{20}$ alkyl or fluoroalkyl groups of $R^5$, $R^6$, $R^{9a}$ to $R^{9d}$, $R^{11}$ and $R^{12}$ are as described for $R^1$ and $R^2$.

The straight, branched or cyclic $C_1$-$C_{20}$ alkylene groups of $R^{10}$ are the foregoing alkyl groups with one hydrogen atom being eliminated. The fluoroalkylene groups are these alkylene groups in which some or all of hydrogen atoms are replaced by fluorine atoms.

Illustrative, non-limiting examples of the recurring units having formula (6') are given below.

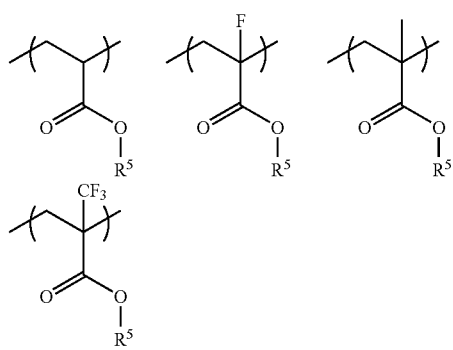

Herein, $R^5$ is hydrogen, an acid labile group, an adhesive group, or a straight, branched or cyclic $C_1$-$C_{20}$ alkyl or fluoroalkyl group.

Illustrative, non-limiting examples of the recurring units having formula (7') are given below.

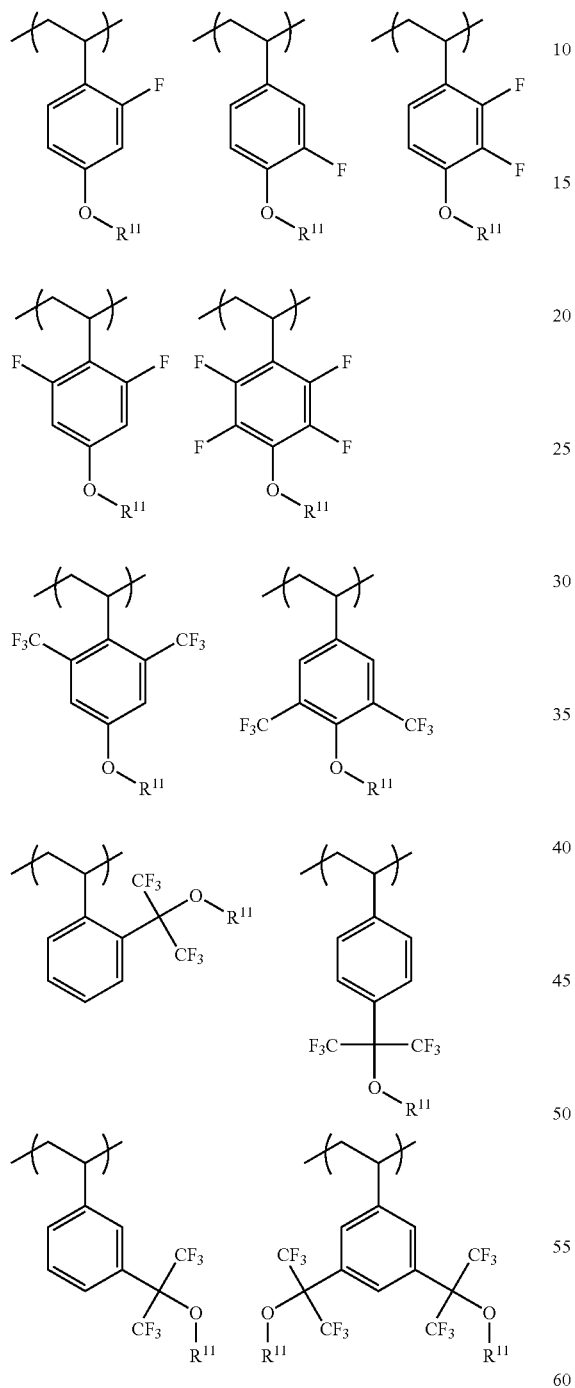

Herein, $R^{11}$ is hydrogen, an acid labile group, an adhesive group, or a straight, branched or cyclic $C_1$-$C_{20}$ alkyl or fluoroalkyl group.

Illustrative, non-limiting examples of the recurring units having formula (8') are given below.

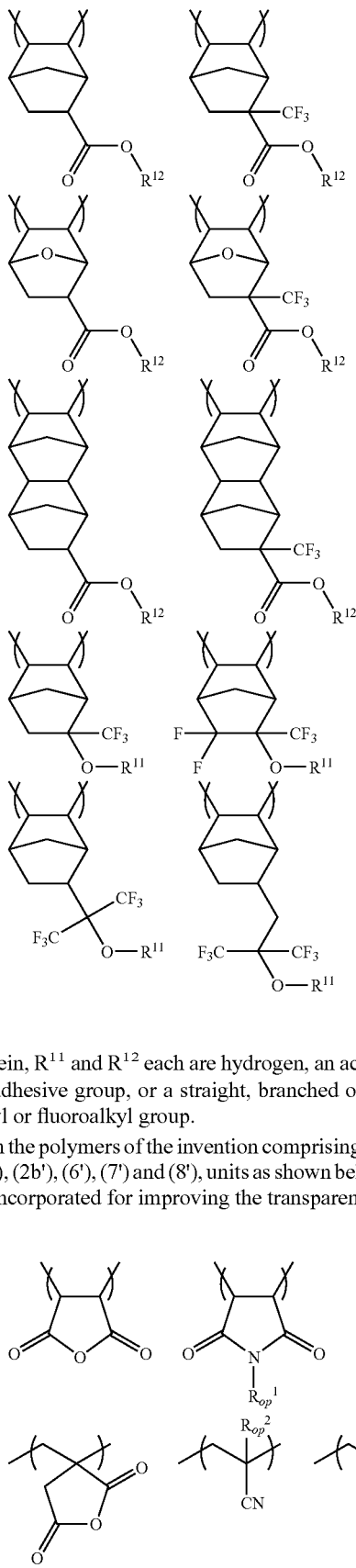

Herein, $R^{11}$ and $R^{12}$ each are hydrogen, an acid labile group, an adhesive group, or a straight, branched or cyclic $C_1$-$C_{20}$ alkyl or fluoroalkyl group.

In the polymers of the invention comprising recurring units (2a'), (2b'), (6'), (7') and (8'), units as shown below may further be incorporated for improving the transparency of the resin.

-continued

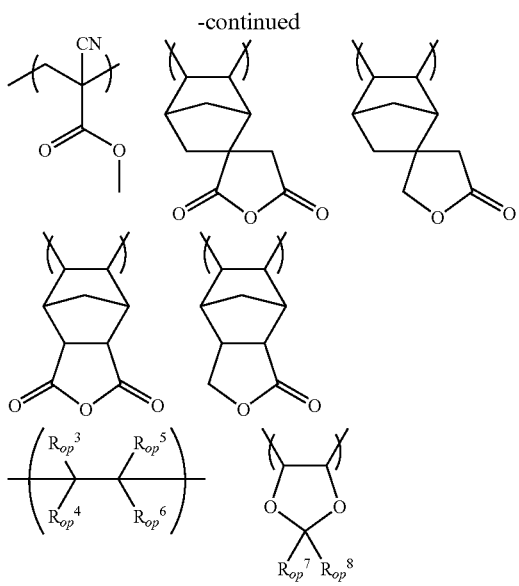

Herein, $R_{op}^1$ and $R_{op}^2$ each are hydrogen or a straight, branched or cyclic $C_1$-$C_{20}$ alkyl or fluoroalkyl group, each of $R_{op}^3$ to $R_{op}^6$ is hydrogen, fluorine or a $C_1$-$C_4$ fluoroalkyl group, at least one of $R_{op}^3$ to $R_{op}^6$ contains one or more fluorine atoms. $R_{op}^7$ and $R_{op}^8$ each are hydrogen, methyl or trifluoromethyl.

The polymer of the invention is generally synthesized by dissolving monomers corresponding to the units having formula (2a), (2b), (6) to (8) and adhesion or transparency-improving monomers in a solvent, adding a catalyst thereto, and effecting polymerization reaction while heating or cooling the system if necessary. The polymerization reaction also depends on the type of initiator or catalyst, trigger means (including light, heat, radiation and plasma), and polymerization conditions (including temperature, pressure, concentration, solvent, and additives). Commonly used for preparation of the polymers of the invention are radical copolymerization of triggering polymerization with radicals of 2,2'-azobisisobutyronitrile (AIBN) or the like and ionic polymerization (anionic polymerization) in the presence of alkyllithium and similar catalysts. These polymerization reactions may be carried out in a conventional manner.

The initiator used for radical polymerization is not critical. Exemplary initiators include azo compounds such as AIBN, 2,2'-azobis(4-methoxy-2,4-dimethylvaleronitrile), 2,2'-azobis(2,4-dimethylvaleronitrile), and 2,2'-azobis(2,4,4-trimethylpentane); and peroxide compounds such as tert-butyl peroxypivalate, lauroyl peroxide, benzoyl peroxide and tert-butyl peroxylaurate. Water-soluble initiators include persulfate salts such as potassium persulfate, and redox combinations of potassium persulfate or peroxides such as hydrogen peroxide with reducing agents such as sodium sulfite. The amount of the polymerization initiator used is determined as appropriate in accordance with such factors as the identity of initiator and polymerization conditions, although the amount is often in the range of about 0.001 to 5% by weight, especially about 0.01 to 2% by weight based on the total weight of monomers to be polymerized.

For the polymerization reaction, a solvent may be used. The polymerization solvent used herein is preferably one which does not interfere with the polymerization reaction. Typical solvents include ester solvents such as ethyl acetate and n-butyl acetate, ketone solvents such as acetone, methyl ethyl ketone and methyl isobutyl ketone, aliphatic or aromatic hydrocarbon solvents such as toluene, xylene and cyclohexane, alcohol solvents such as isopropyl alcohol and ethylene glycol monomethyl ether, and ether solvents such as diethyl ether, dioxane, and tetrahydrofuran (THF). These solvents may be used alone or in admixture of two or more. Further, any of well-known molecular weight modifiers such as dodecylmercaptan may be used in the polymerization system.

The temperature of polymerization reaction varies in accordance with the identity of polymerization initiator and the boiling point of the solvent although it is often preferably in the range of about 20 to 200° C., and especially about 50 to 140° C. Any desired reactor or vessel may be used for the polymerization reaction.

From the solution or dispersion of the polymer thus obtained, the organic solvent or water serving as the reaction medium is removed by any of well-known techniques. Suitable techniques include, for example, re-precipitation followed by filtration, and heat distillation under vacuum.

Desirably the polymer has a weight average molecular weight (Mw) of about 1,000 to about 500,000, and especially about 2,000 to about 100,000. Note that the Mw is determined by gel permeation chromatography (GPC) using polystyrene standards.

In the polymers of the invention wherein U1 stands for units having formula (2a') or (2b'), U2 stands for units having formula (6'), U3 stands for units having formula (7'), U4 stands for units having formula (8'), and U5 stands for adhesion or transparency-improving units, the molar proportion of U1 through U5, with the proviso that U1+U2+U3+U4+U5=1, is preferably determined so as to meet:

$0<U1\leq0.5$, more preferably $0.1\leq U1\leq0.3$, $0\leq U2\leq0.9$, more preferably $0.2\leq U2\leq0.9$, $0\leq U3\leq0.8$, more preferably $0\leq U3\leq0.5$, $0\leq U4\leq0.6$, more preferably $0\leq U4\leq0.4$, and $0\leq U5\leq0.4$, more preferably $0\leq U5\leq0.2$.

The polymer of the invention can be used as a base resin in resist compositions, specifically chemical amplification type resist compositions, and especially chemical amplification type positive working resist compositions. It is understood that the polymer of the invention may be admixed with another polymer for the purpose of altering the dynamic properties, thermal properties, alkali solubility and other physical properties of polymer film. The type of the other polymer which can be admixed is not critical. Any of polymers known to be useful in resist use may be admixed in any desired proportion.

Not only as a base resin in resist composition, the polymer of the invention comprising recurring units (2a') or (2b') is also useful as a resist protecting film, especially in the immersion lithography. When the polymer is used as a resist protecting film, it is not necessary to block hydroxyl groups in the recurring units having formula (2a') or (2b') with acid labile groups or to copolymerize them with recurring units having acid labile groups. In the resist protecting film application, the inventive polymers include homopolymers consisting of recurring units (2a') or (2b'), copolymers of a monomer having formula (2a) or (2b) and a carboxyl-bearing monomer such as (meth)acrylic acid, copolymers of a monomer having formula (2a) or (2b) and a fluorinated alkyl ester of (meth) acrylic acid, and the like.

Resist Composition

As long as the polymer of the invention is used as a base resin, the resist composition of the invention may be prepared using well-known components. In a preferred embodiment, the chemically amplified positive resist composition is defined as comprising (A) the above-defined polymer as a base resin, (B) an organic solvent, and (C) a photoacid generator. In the resist composition, there may be further formulated (D) a nitrogen-containing organic compound and/or (E) a dissolution inhibitor.

Component (B)

The organic solvent used as component (B) in the invention may be any organic solvent in which the base resin (inventive polymer), photoacid generator, and other components are soluble. Illustrative, non-limiting, examples of the organic solvent include ketones such as cyclohexanone and methyl-2-n-amylketone; alcohols such as 3-methoxybutanol, 3-methyl-3-methoxybutanol, 1-methoxy-2-propanol, and 1-ethoxy-2-propanol; ethers such as propylene glycol monomethyl ether, propylene glycol monoethyl ether, propylene glycol dimethyl ether, ethylene glycol monomethyl ether, ethylene glycol monoethyl ether, and diethylene glycol dimethyl ether; and esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate.

These solvents may be used alone or in combinations of two or more thereof. Of the above organic solvents, preferred are diethylene glycol dimethyl ether and 1-ethoxy-2-propanol, in which the photoacid generator is most soluble, and propylene glycol monomethyl ether acetate (PGMEA) which is safe, and mixtures thereof.

The solvent is preferably used in an amount of about 300 to 10,000 parts by weight, more preferably about 500 to 5,000 parts by weight per 100 parts by weight of the base resin.

Component (C)

The acid generators used herein include
(i) onium salts of the formula (P1a-1), (P1a-2) or (P1b),
(ii) diazomethane derivatives of the formula (P2),
(iii) glyoxime derivatives of the formula (P3),
(iv) bissulfone derivatives of the formula (P4),
(v) sulfonic acid esters of N-hydroxyimide compounds of the formula (P5),
(vi) β-ketosulfonic acid derivatives,
(vii) disulfone derivatives,
(viii) nitrobenzylsulfonate derivatives, and
(ix) sulfonate derivatives.

These acid generators are described in detail.

(i) Onium salts of formula (P1a-1), (P1a-2) or (P1b):

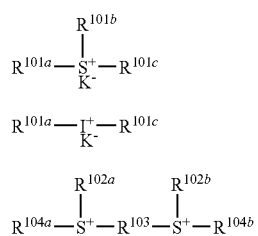

Herein, $R^{101a}$, $R^{101b}$, and $R^{101c}$ independently represent straight, branched or cyclic alkyl, alkenyl, oxoalkyl or oxoalkenyl groups of 1 to 12 carbon atoms, aryl groups of 6 to 20 carbon atoms, or aralkyl or aryloxoalkyl groups of 7 to 12 carbon atoms, wherein some or all of the hydrogen atoms may be replaced by alkoxy or other groups. Also, $R^{101b}$ and $R^{101c}$, taken together, may form a ring. $R^{101b}$ and $R^{101c}$ are alkylene groups of 1 to 6 carbon atoms when they form a ring. $R^{102a}$ and $R^{102b}$ independently represent straight, branched or cyclic alkyl groups of 1 to 8 carbon atoms. $R^{103}$ represents a straight, branched or cyclic alkylene group of 1 to 10 carbon atoms. $R^{104a}$ and $R^{104b}$ independently represent 2-oxoalkyl groups of 3 to 7 carbon atoms. $K^-$ is a non-nucleophilic counter ion.

$R^{101a}$, $R^{101b}$, and $R^{101c}$ may be the same or different and are illustrated below. Exemplary alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl. Exemplary alkenyl groups include vinyl, allyl, propenyl, butenyl, hexenyl, and cyclohexenyl. Exemplary oxoalkyl groups include 2-oxocyclopentyl and 2-oxocyclohexyl as well as 2-oxopropyl, 2-cyclopentyl-2-oxoethyl, 2-cyclohexyl-2-oxoethyl, and 2-(4-methylcyclohexyl)-2-oxoethyl. Exemplary aryl groups include phenyl and naphthyl; alkoxyphenyl groups such as p-methoxyphenyl, m-methoxyphenyl, o-methoxyphenyl, ethoxyphenyl, p-tert-butoxyphenyl, and m-tert-butoxyphenyl; alkylphenyl groups such as 2-methylphenyl, 3-methylphenyl, 4-methylphenyl, ethylphenyl, 4-tert-butylphenyl, 4-butylphenyl, and dimethylphenyl; alkylnaphthyl groups such as methylnaphthyl and ethylnaphthyl; alkoxynaphthyl groups such as methoxynaphthyl and ethoxynaphthyl; dialkylnaphthyl groups such as dimethylnaphthyl and diethylnaphthyl; and dialkoxynaphthyl groups such as dimethoxynaphthyl and diethoxynaphthyl. Exemplary aralkyl groups include benzyl, phenylethyl, and phenethyl. Exemplary aryloxoalkyl groups are 2-aryl-2-oxoethyl groups such as 2-phenyl-2-oxoethyl, 2-(1-naphthyl)-2-oxoethyl, and 2-(2-naphthyl)-2-oxoethyl.

Illustrative of the groups represented by $R^{102a}$ and $R^{102b}$ are methyl, ethyl, propyl, isopropyl, n-butyl, sec-butyl, tert-butyl, pentyl, hexyl, heptyl, octyl, cyclopentyl, cyclohexyl, cyclopropylmethyl, 4-methylcyclohexyl, and cyclohexylmethyl. Illustrative of the groups represented by $R^{103}$ are methylene, ethylene, propylene, butylene, pentylene, hexylene, heptylene, octylene, nonylene, 1,4-cyclohexylene, 1,2-cyclohexylene, 1,3-cyclopentylene, 1,4-cyclooctylene, and 1,4-cyclohexanedimethylene. Illustrative of the groups represented by $R^{104a}$ and $R^{104b}$ are 2-oxopropyl, 2-oxocyclopentyl, 2-oxocyclohexyl, and 2-oxocycloheptyl.

Examples of the non-nucleophilic counter ion represented by $K^-$ include halide ions such as chloride and bromide ions, fluoroalkylsulfonate ions such as triflate, 1,1,1-trifluoroethanesulfonate, and nonafluorobutanesulfonate, arylsulfonate ions such as tosylate, benzenesulfonate, 4-fluorobenzenesulfonate, and 1,2,3,4,5-pentafluorobenzenesulfonate, and alkylsulfonate ions such as mesylate and butanesulfonate.

(ii) Diazomethane derivatives of formula (P2)

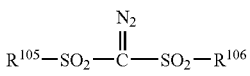

Herein, $R^{105}$ and $R^{106}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms.

Of the groups represented by $R^{105}$ and $R^{106}$, exemplary alkyl groups include methyl, ethyl, propyl, isopropyl, n-butyl, sec-butyl, tert-butyl, pentyl, hexyl, heptyl, octyl, amyl, cyclopentyl, cyclohexyl, cycloheptyl, norbornyl, and adamantyl. Exemplary halogenated alkyl groups include trifluoromethyl, 1,1,1-trifluoroethyl, 1,1,1-trichloroethyl, and nonafluorobutyl. Exemplary aryl groups include phenyl; alkoxyphenyl groups such as p-methoxyphenyl, m-methoxyphenyl, o-methoxyphenyl, ethoxyphenyl, p-tert-butoxyphenyl, and m-tert-butoxyphenyl; and alkylphenyl groups such as 2-methylphenyl, 3-methylphenyl, 4-methylphenyl, ethylphenyl, 4-tert-butylphenyl, 4-butylphenyl, and dimethylphenyl. Exemplary halogenated aryl groups include fluorophenyl, chlorophenyl, and 1,2,3,4,5-pentafluorophenyl. Exemplary aralkyl groups include benzyl and phenethyl.

(iii) Glyoxime derivatives of formula (P3)

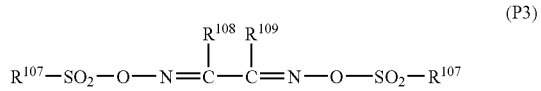

(P3)

Herein, $R^{107}$, $R^{108}$, and $R^{109}$ independently represent straight, branched or cyclic alkyl or halogenated alkyl groups of 1 to 12 carbon atoms, aryl or halogenated aryl groups of 6 to 20 carbon atoms, or aralkyl groups of 7 to 12 carbon atoms. Also, $R^{108}$ and $R^{109}$, taken together, may form a ring. $R^{108}$ and $R^{109}$ are straight or branched alkylene groups of 1 to 6 carbon atoms when they form a ring.

Illustrative examples of the alkyl, halogenated alkyl, aryl, halogenated aryl, and aralkyl groups represented by $R^{107}$, $R^{108}$, and $R^{109}$ are the same as exemplified for $R^{105}$ and $R^{106}$. Examples of the alkylene groups represented by $R^{108}$ and $R^{109}$ include methylene, ethylene, propylene, butylene, and hexylene.

(iv) Bissulfone derivatives of formula (P4)

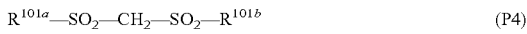

(P4)

Herein, $R^{101a}$ and $R^{101b}$ are independently straight, branched or cyclic alkyl, alkenyl, oxoalkyl or oxoalkenyl groups of 1 to 12 carbon atoms, aryl groups of 6 to 20 carbon atoms, or aralkyl or aryloxoalkyl groups of 7 to 12 carbon atoms, wherein some or all of the hydrogen atoms may be replaced by alkoxy or other groups. Examples of $R^{101a}$ and $R^{101b}$ are as described above for the onium salts (i).

(v) Sulfonic acid esters of N-hydroxyimide compounds of formula (P5)

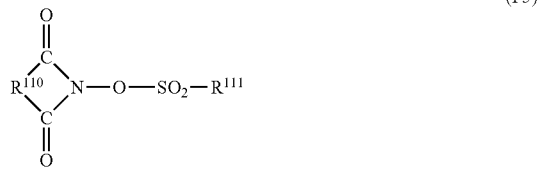

(P5)

Herein, $R^{110}$ is an arylene group of 6 to 10 carbon atoms, alkylene group of 1 to 6 carbon atoms, or alkenylene group of 2 to 6 carbon atoms wherein some or all of the hydrogen atoms may be replaced by straight or branched alkyl or alkoxy groups of 1 to 4 carbon atoms, nitro, acetyl, or phenyl groups.

$R^{111}$ is a straight, branched or cyclic alkyl group of 1 to 8 carbon atoms, alkenyl, alkoxyalkyl, phenyl or naphthyl group wherein some or all of the hydrogen atoms may be replaced by alkyl or alkoxy groups of 1 to 4 carbon atoms, phenyl groups (which may have substituted thereon an alkyl or alkoxy of 1 to 4 carbon atoms, nitro, or acetyl group), heteroaromatic groups of 3 to 5 carbon atoms, or chlorine or fluorine atoms.

Of the groups represented by $R^{110}$, exemplary arylene groups include 1,2-phenylene and 1,8-naphthylene; exemplary alkylene groups include methylene, ethylene, trimethylene, tetramethylene, phenylethylene, and norbornane-2,3-diyl; and exemplary alkenylene groups include 1,2-vinylene, 1-phenyl-1,2-vinylene, and 5-norbornene-2,3-diyl. Of the groups represented by $R^{111}$, exemplary alkyl groups are as exemplified for $R^{101a}$ to $R^{101c}$; exemplary alkenyl groups include vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl, and 7-octenyl; and exemplary alkoxyalkyl groups include methoxymethyl, ethoxymethyl, propoxymethyl, butoxymethyl, pentyloxymethyl, hexyloxymethyl, heptyloxymethyl, methoxyethyl, ethoxyethyl, propoxyethyl, butoxyethyl, pentyloxyethyl, hexyloxyethyl, methoxypropyl, ethoxypropyl, propoxypropyl, butoxypropyl, methoxybutyl, ethoxybutyl, propoxybutyl, methoxypentyl, ethoxypentyl, methoxyhexyl, and methoxyheptyl.

Of the substituents on these groups, the alkyl groups of 1 to 4 carbon atoms include methyl, ethyl, propyl, isopropyl, n-butyl, isobutyl and tert-butyl; the alkoxy groups of 1 to 4 carbon atoms include methoxy, ethoxy, propoxy, isopropoxy, n-butoxy, isobutoxy, and tert-butoxy; the phenyl groups which may have substituted thereon an alkyl or alkoxy of 1 to 4 carbon atoms, nitro, or acetyl group include phenyl, tolyl, p-tert-butoxyphenyl, p-acetylphenyl and p-nitrophenyl; the hetero-aromatic groups of 3 to 5 carbon atoms include pyridyl and furyl.

Illustrative examples of the acid generators (i) to (ix) include:
  onium salts such as
  diphenyliodonium trifluoromethanesulfonate,
  (p-tert-butoxyphenyl)phenyliodonium trifluoromethanesulfonate,
  diphenyliodonium p-toluenesulfonate,
  (p-tert-butoxyphenyl)phenyliodonium p-toluenesulfonate,
  triphenylsulfonium trifluoromethanesulfonate,
  (p-tert-butoxyphenyl)diphenylsulfonium trifluoromethanesulfonate,
  bis(p-tert-butoxyphenyl)phenylsulfonium trifluoromethanesulfonate,
  tris(p-tert-butoxyphenyl)sulfonium trifluoromethanesulfonate,
  triphenylsulfonium p-toluenesulfonate,
  (p-tert-butoxyphenyl)diphenylsulfonium p-toluenesulfonate,
  bis(p-tert-butoxyphenyl)phenylsulfonium p-toluenesulfonate,
  tris(p-tert-butoxyphenyl)sulfonium p-toluenesulfonate,
  triphenylsulfonium nonafluorobutanesulfonate,
  triphenylsulfonium butanesulfonate,
  trimethylsulfonium trifluoromethanesulfonate,
  trimethylsulfonium p-toluenesulfonate,
  cyclohexylmethyl(2-oxocyclohexyl)sulfonium trifluoromethanesulfonate,
  cyclohexylmethyl(2-oxocyclohexyl)sulfonium p-toluenesulfonate,
  dimethylphenylsulfonium trifluoromethanesulfonate, dimethylphenylsulfonium p-toluenesulfonate,
dicyclohexylphenylsulfonium trifluoromethanesulfonate,
dicyclohexylphenylsulfonium p-toluenesulfonate,
trinaphthylsulfonium trifluoromethanesulfonate,
cyclohexylmethyl(2-oxocyclohexyl)sulfonium trifluoromethanesulfonate,
(2-norbornyl)methyl(2-oxocyclohexyl)sulfonium trifluoromethanesulfonate,
ethylenebis[methyl(2-oxocyclopentyl)sulfonium trifluoromethanesulfonate], and
1,2'-naphthylcarbonylmethyltetrahydrothiophenium triflate;
  diazomethane derivatives such as
bis(benzenesulfonyl)diazomethane,
bis(p-toluenesulfonyl)diazomethane,
bis(xylenesulfonyl)diazomethane,
bis(cyclohexylsulfonyl)diazomethane,
bis(cyclopentylsulfonyl)diazomethane,
bis(n-butylsulfonyl)diazomethane,
bis(isobutylsulfonyl)diazomethane,
bis(sec-butylsulfonyl)diazomethane,
bis(n-propylsulfonyl)diazomethane,
bis(isopropylsulfonyl)diazomethane,
bis(tert-butylsulfonyl)diazomethane,
bis(n-amylsulfonyl)diazomethane,
bis(isoamylsulfonyl)diazomethane,
bis(sec-amylsulfonyl)diazomethane,
bis(tert-amylsulfonyl)diazomethane,
1-cyclohexylsulfonyl-1-(tert-butylsulfonyl)diazomethane,
1-cyclohexylsulfonyl-1-(tert-amylsulfonyl)diazomethane, and
1-tert-amylsulfonyl-1-(tert-butylsulfonyl)diazomethane;
  glyoxime derivatives such as
bis-O-(p-toluenesulfonyl)-α-dimethylglyoxime,
bis-O-(p-toluenesulfonyl)-α-diphenylglyoxime,
bis-O-(p-toluenesulfonyl)-α-dicyclohexylglyoxime,
bis-O-(p-toluenesulfonyl)-2,3-pentanedioneglyoxime,
bis-O-(p-toluenesulfonyl)-2-methyl-3,4-pentanedioneglyoxime,
bis-O-(n-butanesulfonyl)-α-dimethylglyoxime,
bis-O-(n-butanesulfonyl)-α-diphenylglyoxime,
bis-O-(n-butanesulfonyl)-α-dicyclohexylglyoxime,
bis-O-(n-butanesulfonyl)-2,3-pentanedioneglyoxime,
bis-O-(n-butanesulfonyl)-2-methyl-3,4-pentanedioneglyoxime,
bis-O-(methanesulfonyl)-α-dimethylglyoxime,
bis-O-(trifluoromethanesulfonyl)-α-dimethylglyoxime,
bis-O-(1,1,1-trifluoroethanesulfonyl)-α-dimethylglyoxime,
bis-O-(tert-butanesulfonyl)-α-dimethylglyoxime,
bis-O-(perfluorooctanesulfonyl)-α-dimethylglyoxime,
bis-O-(cyclohexanesulfonyl)-α-dimethylglyoxime,
bis-O-(benzenesulfonyl)-α-dimethylglyoxime,
bis-O-(p-fluorobenzenesulfonyl)-α-dimethylglyoxime,
bis-O-(p-tert-butylbenzenesulfonyl)-α-dimethylglyoxime,
bis-O-(xylenesulfonyl)-α-dimethylglyoxime, and
bis-O-(camphorsulfonyl)-α-dimethylglyoxime;
  bissulfone derivatives such as
bisnaphthylsulfonylmethane, bistrifluoromethylsulfonylmethane,
bismethylsulfonylmethane, bisethylsulfonylmethane,
bispropylsulfonylmethane, bisisopropylsulfonylmethane,
bis-p-toluenesulfonylmethane, and bisbenzenesulfonylmethane;
  β-ketosulfone derivatives such as
2-cyclohexylcarbonyl-2-(p-toluenesulfonyl)propane and
2-isopropylcarbonyl-2-(p-toluenesulfonyl)propane;
  nitrobenzyl sulfonate derivatives such as
2,6-dinitrobenzyl p-toluenesulfonate and
2,4-dinitrobenzyl p-toluenesulfonate;
  sulfonic acid ester derivatives such as
1,2,3-tris(methanesulfonyloxy)benzene,
1,2,3-tris(trifluoromethanesulfonyloxy)benzene, and
1,2,3-tris(p-toluenesulfonyloxy)benzene; and
  sulfonic acid esters of N-hydroxyimides such as
N-hydroxysuccinimide methanesulfonate,
N-hydroxysuccinimide trifluoromethanesulfonate,
N-hydroxysuccinimide ethanesulfonate,
N-hydroxysuccinimide 1-propanesulfonate,
N-hydroxysuccinimide 2-propanesulfonate,
N-hydroxysuccinimide 1-pentanesulfonate,
N-hydroxysuccinimide 1-octanesulfonate,
N-hydroxysuccinimide p-toluenesulfonate,
N-hydroxysuccinimide p-methoxybenzenesulfonate,
N-hydroxysuccinimide 2-chloroethanesulfonate,
N-hydroxysuccinimide benzenesulfonate,
N-hydroxysuccinimide 2,4,6-trimethylbenzenesulfonate,
N-hydroxysuccinimide 1-naphthalenesulfonate,
N-hydroxysuccinimide 2-naphthalenesulfonate,
N-hydroxy-2-phenylsuccinimide methanesulfonate,
N-hydroxymaleimide methanesulfonate,
N-hydroxymaleimide ethanesulfonate,
N-hydroxy-2-phenylmaleimide methanesulfonate,
N-hydroxyglutarimide methanesulfonate,
N-hydroxyglutarimide benzenesulfonate,
N-hydroxyphthalimide methanesulfonate,
N-hydroxyphthalimide benzenesulfonate,
N-hydroxyphthalimide trifluoromethanesulfonate,
N-hydroxyphthalimide p-toluenesulfonate,
N-hydroxynaphthalimide methanesulfonate,
N-hydroxynaphthalimide benzenesulfonate,
N-hydroxy-5-norbornene-2,3-dicarboxyimide methanesulfonate,
N-hydroxy-5-norbornene-2,3-dicarboxyimide trifluoromethanesulfonate, and
N-hydroxy-5-norbornene-2,3-dicarboxyimide p-toluenesulfonate.

Preferred among these acid generators are onium salts such as triphenylsulfonium trifluoromethanesulfonate,
(p-tert-butoxyphenyl)diphenylsulfonium trifluoromethanesulfonate,
tris(p-tert-butoxyphenyl)sulfonium trifluoromethanesulfonate,
triphenylsulfonium p-toluenesulfonate,
(p-tert-butoxyphenyl)diphenylsulfonium p-toluenesulfonate,
tris(p-tert-butoxyphenyl)sulfonium p-toluenesulfonate,
trinaphthylsulfonium trifluoromethanesulfonate,
cyclohexylmethyl(2-oxocyclohexyl)sulfonium trifluoromethanesulfonate,
(2-norbornyl)methyl(2-oxocylohexyl)sulfonium trifluoromethanesulfonate, and
1,2'-naphthylcarbonylmethyltetrahydrothiophenium triflate;
  diazomethane derivatives such as
bis(benzenesulfonyl)diazomethane,
bis(p-toluenesulfonyl)diazomethane,
bis(cyclohexylsulfonyl)diazomethane,
bis(n-butylsulfonyl)diazomethane,
bis(isobutylsulfonyl)diazomethane,
bis(sec-butylsulfonyl)diazomethane,
bis(n-propylsulfonyl)diazomethane,
bis(isopropylsulfonyl)diazomethane, and
bis(tert-butylsulfonyl)diazomethane;
  glyoxime derivatives such as
bis-O-(p-toluenesulfonyl)-α-dimethylglyoxime and
bis-O-(n-butanesulfonyl)-α-dimethylglyoxime;

bissulfone derivatives such as bisnaphthylsulfonylmethane; and sulfonic acid esters of N-hydroxyimide compounds such as
N-hydroxysuccinimide methanesulfonate,
N-hydroxysuccinimide trifluoromethanesulfonate,
N-hydroxysuccinimide 1-propanesulfonate,
N-hydroxysuccinimide 2-propanesulfonate,
N-hydroxysuccinimide 1-pentanesulfonate,
N-hydroxysuccinimide p-toluenesulfonate,
N-hydroxynaphthalimide methanesulfonate, and
N-hydroxynaphthalimide benzenesulfonate.

These acid generators may be used singly or in combinations of two or more thereof. Onium salts are effective for improving rectangularity, while diazomethane derivatives and glyoxime derivatives are effective for reducing standing waves. The combination of an onium salt with a diazomethane or a glyoxime derivative allows for fine adjustment of the profile.

The acid generator is preferably added in an amount of 0.1 to 50 parts by weight, and especially 0.5 to 40 parts by weight, per 100 parts by weight of the base polymer. Less than 0.1 pbw of the acid generator may generate an insufficient amount of acid upon light exposure, resulting in a low sensitivity and resolution. More than 50 pbw of the acid generator may lower the transmittance of the resist and result in a poor resolution.

Component (D)

The nitrogen-containing organic compound (D) is preferably a compound capable of suppressing the rate of diffusion when the acid generated by the photoacid generator diffuses within the resist film. The inclusion of this type of nitrogen-containing compound holds down the rate of acid diffusion within the resist film, resulting in better resolution. In addition, it suppresses changes in sensitivity following exposure, thus reducing substrate and environment dependence, as well as improving the exposure latitude and the pattern profile.

Examples of suitable nitrogen-containing organic compounds include primary, secondary, and tertiary aliphatic amines, mixed amines, aromatic amines, heterocyclic amines, nitrogen-containing compounds having carboxyl group, nitrogen-containing compounds having sulfonyl group, nitrogen-containing compounds having hydroxyl group, nitrogen-containing compounds having hydroxyphenyl group, alcoholic nitrogen compounds, amide derivatives, and imide derivatives.

Examples of suitable primary aliphatic amines include methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine.

Examples of suitable secondary aliphatic amines include dimethylamine, diethylamine, di-n-propylamine, di-isopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine.

Examples of suitable tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N, N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine.

Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, and diaminonaphthalene; and pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable nitrogen-containing compounds having carboxyl group include aminobenzoic acid, indolecarboxylic acid, and amino acid derivatives (e.g., nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine).

Examples of suitable nitrogen-containing compounds having sulfonyl group include 3-pyridinesulfonic acid and pyridinium p-toluenesulfonate.

Examples of suitable nitrogen-containing compounds having hydroxyl group, nitrogen-containing compounds having hydroxyphenyl group, and alcoholic nitrogen compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide.

Examples of suitable amide derivatives include formamide, N-methylformamide, N,N-dimethylformamide, acetamide, N-methylacetamide, N,N-dimethylacetamide, propionamide, and benzamide. Suitable imide derivatives include phthalimide, succinimide, and maleimide.

In addition, nitrogen-containing organic compounds of the following general formula (B)-1 may also be included alone or in admixture.

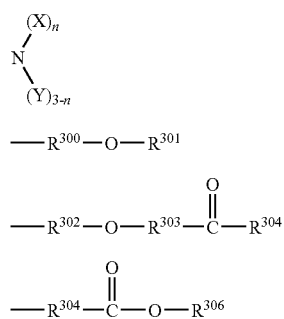

In the formulas, n is 1, 2 or 3. The side chain X may be the same or different and is represented by the formula (X)-1, (X)-2 or (X)-3. The side chain Y may be the same or different and stands for hydrogen or a straight, branched or cyclic alkyl group of 1 to 20 carbon atoms which may contain an ether or hydroxyl group. Two or three X's may bond together to form a ring. $R^{300}$, $R^{302}$ and $R^{305}$ are independently straight or branched alkylene groups of 1 to 4 carbon atoms; $R^{301}$ and $R^{304}$ are independently hydrogen or straight, branched or cyclic alkyl groups of 1 to 20 carbon atoms, which may contain at least one hydroxyl group, ether, ester or lactone ring; $R^{303}$ is a single bond or a straight or branched alkylene group of 1 to 4 carbon atoms; and $R^{306}$ is hydrogen or a straight, branched or cyclic alkyl group of 1 to 20 carbon atoms, which may contain at least one hydroxyl group, ether, ester or lactone ring.

Illustrative, non-limiting examples of the compounds of formula (B)-1 include
tris(2-methoxymethoxyethyl)amine,
tris{2-(2-methoxyethoxy)ethyl}amine,
tris{2-(2-methoxyethoxymethoxy)ethyl}amine,
tris{2-(1-methoxyethoxy)ethyl}amine,
tris{2-(1-ethoxyethoxy)ethyl}amine,
tris{2-(1-ethoxypropoxy)ethyl}amine,
tris[2-{2-(2-hydroxyethoxy)ethoxy}ethyl]amine,
4,7,13,16,21,24-hexaoxa-1,10-diazabicyclo[8.8.8]hexacosane,
4,7,13,18-tetraoxa-1,10-diazabicyclo[8.5.5]eicosane,
1,4,10,13-tetraoxa-7,16-diazabicyclooctadecane,
1-aza-12-crown-4, 1-aza-15-crown-5, 1-aza-18-crown-6,
tris(2-formyloxyethyl)amine, tris(2-acetoxyethyl)amine,
tris(2-propionyloxyethyl)amine, tris(2-butyryloxyethyl)amine,
tris(2-isobutyryloxyethyl)amine, tris(2-valeryloxyethyl)amine,
tris(2-pivaloyloxyethyl)amine, N,N-bis(2-acetoxyethyl)-2-(acetoxyacetoxy)ethylamine,
tris(2-methoxycarbonyloxyethyl)amine,
tris(2-tert-butoxycarbonyloxyethyl)amine,
tris[2-(2-oxopropoxy)ethyl]amine,
tris[2-(methoxycarbonylmethyl)oxyethyl]amine,
tris[2-(tert-butoxycarbonylmethyloxy)ethyl]amine,
tris[2-(cyclohexyloxycarbonylmethyloxy)ethyl]amine,
tris(2-methoxycarbonylethyl)amine,
tris(2-ethoxycarbonylethyl)amine,
N,N-bis(2-hydroxyethyl)-2-(methoxycarbonyl)ethylamine,
N,N-bis(2-acetoxyethyl)-2-(methoxycarbonyl)ethylamine,
N,N-bis(2-hydroxyethyl)-2-(ethoxycarbonyl)ethylamine,
N,N-bis(2-acetoxyethyl)-2-(ethoxycarbonyl)ethylamine,
N,N-bis(2-hydroxyethyl)-2-(2-methoxyethoxycarbonyl)ethylamine,
N,N-bis(2-acetoxyethyl)-2-(2-methoxyethoxycarbonyl)ethylamine,
N,N-bis(2-hydroxyethyl)-2-(2-hydroxyethoxycarbonyl)ethylamine,
N,N-bis(2-acetoxyethyl)-2-(2-acetoxyethoxycarbonyl)ethylamine,
N,N-bis(2-hydroxyethyl)-2-[(methoxycarbonyl)methoxycarbonyl]-ethylamine,
N,N-bis(2-acetoxyethyl)-2-[(methoxycarbonyl)methoxycarbonyl]-ethylamine,
N,N-bis(2-hydroxyethyl)-2-(2-oxopropoxycarbonyl)ethylamine,
N,N-bis(2-acetoxyethyl)-2-(2-oxopropoxycarbonyl)ethylamine,
N,N-bis(2-hydroxyethyl)-2-(tetrahydrofurfuryloxycarbonyl)-ethylamine,
N,N-bis(2-acetoxyethyl)-2-(tetrahydrofurfuryloxycarbonyl)-ethylamine,
N,N-bis(2-hydroxyethyl)-2-[(2-oxotetrahydrofuran-3-yl)oxy-carbonyl]ethylamine,
N,N-bis(2-acetoxyethyl)-2-[(2-oxotetrahydrofuran-3-yl)oxy-carbonyl]ethylamine,
N,N-bis(2-hydroxyethyl)-2-(4-hydroxybutoxycarbonyl)ethylamine,
N,N-bis(2-formyloxyethyl)-2-(4-formyloxybutoxycarbonyl)-ethylamine,
N,N-bis(2-formyloxyethyl)-2-(2-formyloxyethoxycarbonyl)-ethylamine,
N,N-bis(2-methoxyethyl)-2-(methoxycarbonyl)ethylamine,
N-(2-hydroxyethyl)-bis[2-(methoxycarbonyl)ethyl]amine,
N-(2-acetoxyethyl)-bis[2-(methoxycarbonyl)ethyl]amine,
N-(2-hydroxyethyl)-bis[2-(ethoxycarbonyl)ethyl]amine,
N-(2-acetoxyethyl)-bis[2-(ethoxycarbonyl)ethyl]amine,
N-(3-hydroxy-1-propyl)-bis[2-(methoxycarbonyl)ethyl]amine,
N-(3-acetoxy-1-propyl)-bis[2-(methoxycarbonyl)ethyl]amine,
N-(2-methoxyethyl)-bis[2-(methoxycarbonyl)ethyl]amine,
N-butyl-bis[2-(methoxycarbonyl)ethyl]amine,
N-butyl-bis[2-(2-methoxyethoxycarbonyl)ethyl]amine,
N-methyl-bis(2-acetoxyethyl)amine,
N-ethyl-bis(2-acetoxyethyl)amine,
N-methyl-bis(2-pivaloyloxyethyl)amine,
N-ethyl-bis[2-(methoxycarbonyloxy)ethyl]amine,
N-ethyl-bis[2-(tert-butoxycarbonyloxy)ethyl]amine,
tris(methoxycarbonylmethyl)amine,
tris(ethoxycarbonylmethyl)amine,
N-butyl-bis(methoxycarbonylmethyl)amine,
N-hexyl-bis(methoxycarbonylmethyl)amine, and
β-(diethylamino)-δ-valerolactone.

Also useful are one or more of nitrogen-containing organic cyclic structure compounds having the following general formula (B)-2.

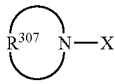 (B)-2

Herein X is a substituent group of (X)-1 to (X)-3, and $R^{307}$ is a straight or branched alkylene group of 2 to 20 carbon atoms which may contain one or more carbonyl, ether, ester or sulfide groups.

Illustrative examples of the compounds having formula (B)-2 include
1-[2-(methoxymethoxy)ethyl]pyrrolidine,
1-[2-(methoxymethoxy)ethyl]piperidine,
4-[2-(methoxymethoxy)ethyl]morpholine,
1-[2-[(2-methoxyethoxy)methoxy]ethyl]pyrrolidine,
1-[2-[(2-methoxyethoxy)methoxy]ethyl]piperidine,
4-[2-[(2-methoxyethoxy)methoxy]ethyl]morpholine,
2-(1-pyrrolidinyl)ethyl acetate, 2-piperidinoethyl acetate,
2-morpholinoethyl acetate, 2-(1-pyrrolidinyl)ethyl formate,
2-piperidinoethyl propionate,
2-morpholinoethyl acetoxyacetate,
2-(1-pyrrolidinyl)ethyl methoxyacetate,
4-[2-(methoxycarbonyloxy)ethyl]morpholine,
1-[2-(t-butoxycarbonyloxy)ethyl]piperidine,
4-[2-(2-methoxyethoxycarbonyloxy)ethyl]morpholine,
methyl 3-(1-pyrrolidinyl)propionate,
methyl 3-piperidinopropionate,
methyl 3-morpholinopropionate,
methyl 3-(thiomorpholino)propionate,
methyl 2-methyl-3-(1-pyrrolidinyl)propionate,
ethyl 3-morpholinopropionate,
methoxycarbonylmethyl 3-piperidinopropionate,
2-hydroxyethyl 3-(1-pyrrolidinyl)propionate,
2-acetoxyethyl 3-morpholinopropionate,
2-oxotetrahydrofuran-3-yl 3-(1-pyrrolidinyl)propionate,
tetrahydrofurfuryl 3-morpholinopropionate,
glycidyl 3-piperidinopropionate,
2-methoxyethyl 3-morpholinopropionate,
2-(2-methoxyethoxy)ethyl 3-(1-pyrrolidinyl)propionate,
butyl 3-morpholinopropionate,
cyclohexyl 3-piperidinopropionate,
α-(1-pyrrolidinyl)methyl-γ-butyrolactone,
β-piperidino-γ-butyrolactone, β-morpholino-δ-valerolactone,
methyl 1-pyrrolidinylacetate, methyl piperidinoacetate,
methyl morpholinoacetate, methyl thiomorpholinoacetate,
ethyl 1-pyrrolidinylacetate, and
2-methoxyethyl morpholinoacetate.

Also, one or more of cyano-containing compounds having the following general formulae (B)-3 to (B)-6 may be blended.

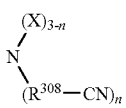 (B)-3

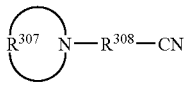 (B)-4

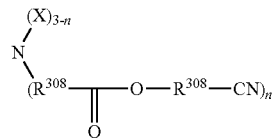 (B)-5

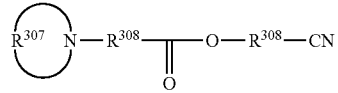 (B)-6

Herein, X is a substituent group of (X)-1 to (X)-3, $R^{307}$ is as defined above, n is 1, 2 or 3, and $R^{308}$ and $R^{309}$ each are independently a straight or branched alkylene group of 1 to 4 carbon atoms.

Illustrative examples of the nitrogen-containing compounds having cyano as represented by formulae (B)-3 to (B)-6 include 3-(diethylamino)propiononitrile,
N,N-bis(2-hydroxyethyl)-3-aminopropiononitrile,
N,N-bis(2-acetoxyethyl)-3-aminopropiononitrile,
N,N-bis(2-formyloxyethyl)-3-aminopropiononitrile,
N,N-bis(2-methoxyethyl)-3-aminopropiononitrile,
N,N-bis[2-(methoxymethoxy)ethyl]-3-aminopropiononitrile,
methyl N-(2-cyanoethyl)-N-(2-methoxyethyl)-3-aminopropionate,
methyl N-(2-cyanoethyl)-N-(2-hydroxyethyl)-3-aminopropionate,
methyl N-(2-acetoxyethyl)-N-(2-cyanoethyl)-3-aminopropionate,
N-(2-cyanoethyl)-N-ethyl-3-aminopropiononitrile,
N-(2-cyanoethyl)-N-(2-hydroxyethyl)-3-aminopropiononitrile,
N-(2-acetoxyethyl)-N-(2-cyanoethyl)-3-aminopropiononitrile,
N-(2-cyanoethyl)-N-(2-formyloxyethyl)-3-aminopropiononitrile,
N-(2-cyanoethyl)-N-(2-methoxyethyl)-3-aminopropiononitrile,
N-(2-cyanoethyl)-N-[2-(methoxymethoxy)ethyl]-3-aminopropiononitrile,
N-(2-cyanoethyl)-N-(3-hydroxy-1-propyl)-3-aminopropiononitrile,
N-(3-acetoxy-1-propyl)-N-(2-cyanoethyl)-3-aminopropiononitrile,
N-(2-cyanoethyl)-N-(3-formyloxy-1-propyl)-3-aminopropiononitrile,
N-(2-cyanoethyl)-N-tetrahydrofurfuryl-3-aminopropiononitrile,
N,N-bis(2-cyanoethyl)-3-aminopropiononitrile,
diethylaminoacetonitrile,
N,N-bis(2-hydroxyethyl)aminoacetonitrile,
N,N-bis(2-acetoxyethyl)aminoacetonitrile,
N,N-bis(2-formyloxyethyl)aminoacetonitrile,
N,N-bis(2-methoxyethyl)aminoacetonitrile,
N,N-bis[2-(methoxymethoxy)ethyl]aminoacetonitrile,
methyl N-cyanomethyl-N-(2-methoxyethyl)-3-aminopropionate,
methyl N-cyanomethyl-N-(2-hydroxyethyl)-3-aminopropionate,
methyl N-(2-acetoxyethyl)-N-cyanomethyl-3-aminopropionate,
N-cyanomethyl-N-(2-hydroxyethyl)aminoacetonitrile, N-(2-acetoxyethyl)-N-(cyanomethyl)aminoacetonitrile,
N-cyanomethyl-N-(2-formyloxyethyl)aminoacetonitrile,
N-cyanomethyl-N-(2-methoxyethyl)aminoacetonitrile,
N-cyanomethyl-N-[2-(methoxymethoxy)ethyl]aminoacetonitrile,
N-cyanomethyl-N-(3-hydroxy-1-propyl)aminoacetonitrile,
N-(3-acetoxy-1-propyl)-N-(cyanomethyl)aminoacetonitrile,
N-cyanomethyl-N-(3-formyloxy-1-propyl)aminoacetonitrile,
N,N-bis(cyanomethyl)aminoacetonitrile,
1-pyrrolidinepropiononitrile, 1-piperidinepropiononitrile,
4-morpholinepropiononitrile, 1-pyrrolidineacetonitrile,
1-piperidineacetonitrile, 4-morpholineacetonitrile,
cyanomethyl 3-diethylaminopropionate,
cyanomethyl N,N-bis(2-hydroxyethyl)-3-aminopropionate,
cyanomethyl N,N-bis(2-acetoxyethyl)-3-aminopropionate,
cyanomethyl N,N-bis(2-formyloxyethyl)-3-aminopropionate,
cyanomethyl N,N-bis(2-methoxyethyl)-3-aminopropionate,
cyanomethyl N,N-bis[2-(methoxymethoxy)ethyl]-3-aminopropionate,
2-cyanoethyl 3-diethylaminopropionate,
2-cyanoethyl N,N-bis(2-hydroxyethyl)-3-aminopropionate,
2-cyanoethyl N,N-bis(2-acetoxyethyl)-3-aminopropionate,
2-cyanoethyl N,N-bis(2-formyloxyethyl)-3-aminopropionate,
2-cyanoethyl N,N-bis(2-methoxyethyl)-3-aminopropionate,
2-cyanoethyl N,N-bis[2-(methoxymethoxy)ethyl]-3-aminopropionate,
cyanomethyl 1-pyrrolidinepropionate,
cyanomethyl 1-piperidinepropionate,
cyanomethyl 4-morpholinepropionate,
2-cyanoethyl 1-pyrrolidinepropionate,
2-cyanoethyl 1-piperidinepropionate, and
2-cyanoethyl 4-morpholinepropionate.

Also included are organic nitrogen-containing compounds having an imidazole skeleton and a polar functional group, represented by the general formula (B)-7.

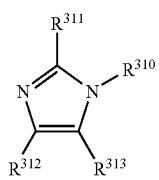

(B)-7

Herein, $R^{310}$ is a straight, branched or cyclic alkyl group of 2 to 20 carbon atoms bearing at least one polar functional group selected from among hydroxyl, carbonyl, ester, ether, sulfide, carbonate, cyano and acetal groups; $R^{311}$, $R^{312}$ and $R^{313}$ are each independently a hydrogen atom, a straight, branched or cyclic alkyl group, aryl group or aralkyl group having 1 to 10 carbon atoms.

Also included are organic nitrogen-containing compounds having a benzimidazole skeleton and a polar functional group, represented by the general formula (B)-8.

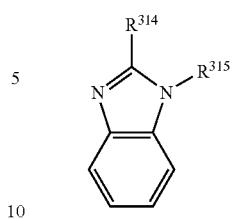

(B)-8

Herein, $R^{314}$ is a hydrogen atom, a straight, branched or cyclic alkyl group, aryl group or aralkyl group having 1 to 10 carbon atoms. $R^{315}$ is a polar functional group-bearing, straight, branched or cyclic alkyl group of 1 to 20 carbon atoms, and the alkyl group contains as the polar functional group at least one group selected from among ester, acetal and cyano groups, and may additionally contain at least one group selected from among hydroxyl, carbonyl, ether, sulfide and carbonate groups.

Further included are heterocyclic nitrogen-containing compounds having a polar functional group, represented by the general formulae (B)-9 and (B)-10.

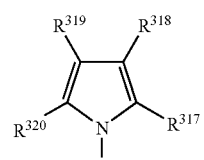

(B)-9

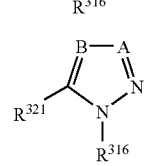

(B)-10

Herein, A is a nitrogen atom or $=C-R^{322}$, B is a nitrogen atom or $=C-R^{323}$, $R^{316}$ is a straight, branched or cyclic alkyl group of 2 to 20 carbon atoms bearing at least one polar functional group selected from among hydroxyl, carbonyl, ester, ether, sulfide, carbonate, cyano and acetal groups; $R^{317}$, $R^{318}$, $R^{319}$ and $R^{320}$ are each independently a hydrogen atom, a straight, branched or cyclic alkyl group or aryl group having 1 to 10 carbon atoms, or a pair of $R^{317}$ and $R^{318}$ and a pair of $R^{319}$ and $R^{320}$, taken together, may form a benzene, naphthalene or pyridine ring with the carbon atom to which they are attached; $R^{321}$ is a hydrogen atom, a straight, branched or cyclic alkyl group or aryl group having 1 to 10 carbon atoms; $R^{322}$ and $R^{323}$ each are a hydrogen atom, a straight, branched or cyclic alkyl group or aryl group having 1 to 10 carbon atoms, or a pair of $R^{321}$ and $R^{323}$, taken together, may form a benzene or naphthalene ring with the carbon atom to which they are attached.

The organic nitrogen-containing compounds may be used alone or in admixture of two or more. The organic nitrogen-containing compound is preferably formulated in an amount of 0.001 to 2 parts, and especially 0.01 to 1 part by weight, per 100 parts by weight of the entire base resin. Less than 0.001 part of the nitrogen-containing compound achieves no or little addition effect whereas more than 2 parts would result in too low a sensitivity.

Component (E)

The dissolution inhibitor (E) is a compound with a weight average molecular weight of up to 3,000 which changes its solubility in an alkaline developer under the action of an acid, and typically selected from phenol and carboxylic acid derivatives in which some or all of hydroxyl groups are substituted with acid labile groups (as described above) and which have a weight average molecular weight of up to 2,500.

Examples of the phenol or carboxylic acid derivative having a weight average molecular weight of up to 2,500 include
4,4'-(1-methylethylidene)bisphenol,
(1,1'-biphenyl-4,4'-diol)-2,2'-methylenebis(4-methylphenol),
4,4-bis(4'-hydroxyphenyl)valeric acid,
tris(4-hydroxyphenyl)methane,
1,1,1-tris(4'-hydroxyphenyl)ethane,
1,1,2-tris(4'-hydroxyphenyl)ethane, phenolphthalein,
thimolphthalein, 3,3'-difluoro[(1,1'-biphenyl)-4,4'-diol],
3,3', 5,5'-tetrafluoro[(1,1'-biphenyl)-4,4'-diol],
4,4'-[2,2,2-trifluoro-1-(trifluoromethyl)ethylidene]bisphenol,
4,4'-methylenebis(2-fluorophenol),
2,2'-methylenebis(4-fluorophenol),
4,4'-isopropylidenebis(2-fluorophenol),
cyclohexylidenebis(2-fluorophenol),
4,4'-[(4-fluorophenyl)methylene]bis(2-fluorophenol),
4,4'-methylenebis(2,6-difluorophenol),
4,4'-(4-fluorophenyl)methylenebis(2,6-difluorophenol),
2,6-bis[(2-hydroxy-5-fluorophenyl)methyl]-4-fluorophenol,
2,6-bis[(4-hydroxy-3-fluorophenyl)methyl]-4-fluorophenol, and
2,4-bis[(3-hydroxy-4-hydroxyphenyl)methyl]-6-methylphenol.

The acid labile groups are the same as formulae (AL-1) to (AL-3) described above.

Illustrative, non-limiting, examples of the dissolution inhibitors which are useful herein include
3,3',5,5'-tetrafluoro[(1,1'-biphenyl)-4,4'-di-t-butoxycarbonyl],
4,4'-[2,2,2-trifluoro-1-(trifluoromethyl)ethylidene]-bisphenol-4,4'-di-t-butoxycarbonyl,
bis(4-(2'-tetrahydropyranyloxy)phenyl)methane,
bis(4-(2'-tetrahydrofuranyloxy)phenyl)methane,
bis(4-tert-butoxyphenyl)methane,
bis(4-tert-butoxycarbonyloxyphenyl)methane,
bis(4-tert-butoxycarbonylmethyloxyphenyl)methane,
bis(4-(1'-ethoxyethoxy)phenyl)methane,
bis(4-(1'-ethoxypropyloxy)phenyl)methane,
2,2-bis(4'-(2"-tetrahydropyranyloxy))propane,
2,2-bis(4'-(2"-tetrahydrofuranyloxy)phenyl)propane,
2,2-bis(4'-tert-butoxyphenyl)propane,
2,2-bis(4'-tert-butoxycarbonyloxyphenyl)propane,
2,2-bis(4-tert-butoxycarbonylmethyloxyphenyl)propane,
2,2-bis(4'-(1"-ethoxyethoxy)phenyl)propane,
2,2-bis(4'-(1"-ethoxypropyloxy)phenyl)propane,
tert-butyl 4,4-bis(4'-(2"-tetrahydropyranyloxy)phenyl)valerate,
tert-butyl 4,4-bis(4'-(2"-tetrahydrofuranyloxy)phenyl)valerate,
tert-butyl 4,4-bis(4'-tert-butoxyphenyl)valerate,
tert-butyl 4,4-bis(4-tert-butoxycarbonyloxyphenyl)valerate,
tert-butyl 4,4-bis(4'-tert-butoxycarbonylmethyloxyphenyl) valerate,
tert-butyl 4,4-bis(4'-(1"-ethoxyethoxy)phenyl)valerate,
tert-butyl 4,4-bis(4'-(1"-ethoxypropyloxy)phenyl)valerate,
tris(4-(2'-tetrahydropyranyloxy)phenyl)methane,
tris(4-(2'-tetrahydrofuranyloxy)phenyl)methane,
tris(4-tert-butoxyphenyl)methane,
tris(4-tert-butoxycarbonyloxyphenyl)methane,
tris(4-tert-butoxycarbonyloxymethylphenyl)methane,
tris(4-(1'-ethoxyethoxy)phenyl)methane,
tris(4-(1'-ethoxypropyloxy)phenyl)methane,
1,1,2-tris(4'-(2"-tetrahydropyranyloxy)phenyl)ethane,
1,1,2-tris(4'-(2"-tetrahydrofuranyloxy)phenyl)ethane,
1,1,2-tris(4'-tert-butoxyphenyl)ethane,
1,1,2-tris(4'-tert-butoxycarbonyloxyphenyl)ethane,
1,1,2-tris(4'-tert-butoxycarbonylmethyloxyphenyl)ethane,
1,1,2-tris(4'-(1'-ethoxyethoxy)phenyl)ethane,
1,1,2-tris(4'-(1'-ethoxypropyloxy)phenyl)ethane,
t-butyl 2-trifluoromethylbenzenecarboxylate,
t-butyl 2-trifluoromethylcyclohexanecarboxylate,
t-butyl decahydronaphthalene-2,6-dicarboxylate,
t-butyl cholate, t-butyl deoxycholate,
t-butyl adamantanecarboxylate, t-butyl adamantaneacetate, and
tetra-t-butyl 1,1'-bicyclohexyl-3,3',4,4'-tetracarboxylate.

In the resist composition of the invention, an appropriate amount of the dissolution inhibitor (E) is up to about 20 parts, and especially up to about 15 parts by weight per 100 parts by weight of the base resin in the composition. More than 20 parts of the dissolution inhibitor leads to resist compositions having poor heat resistance due to increased monomer contents.

In addition to the foregoing components, the resist composition of the invention may include optional ingredients, typically a surfactant which is commonly used for improving the coating characteristics. Optional ingredients may be added in conventional amounts so long as this does not compromise the objects of the invention.

A nonionic surfactant is preferred, examples of which include perfluoroalkyl polyoxyethylene ethanols, fluorinated alkyl esters, perfluoroalkylamine oxides, perfluoroalkyl EO-addition products, and fluorinated organosiloxane compounds. Illustrative examples include Fluorad FC-430 and FC-431 from Sumitomo 3M Ltd., Surflon S-141 and S-145 from Asahi Glass Co., Ltd., Unidyne DS-401, DS-403, and DS-451 from Daikin Industries Ltd., Megaface F-8151 from Dainippon Ink & Chemicals, Inc., and X-70-092 and X-70-093 from Shin-Etsu Chemical Co., Ltd. Preferred surfactants include Fluorad FC-430 from Sumitomo 3M Ltd. and X-70-093 from Shin-Etsu Chemical Co., Ltd.

Pattern formation using the resist composition of the invention may be carried out by a known lithographic technique. For example, the resist composition may be applied onto a substrate such as a silicon wafer by spin coating or the like to form a resist film having a thickness of 0.1 to 1.0 μm, which is then pre-baked on a hot plate at 60 to 200° C. for 10 seconds to 10 minutes, and preferably at 80 to 150° C. for ½ to 5 minutes. A patterning mask having the desired pattern may then be placed over the resist film, and the film exposed through the mask to an electron beam or to high-energy radiation such as deep-UV rays, excimer laser beams, or x-rays in a dose of about 1 to 200 mJ/cm$^2$, and preferably about 10 to 100 mJ/cm$^2$, then post-exposure baked (PEB) on a hot plate at 60 to 150° C. for 10 seconds to 5 minutes, and preferably at 80 to 130° C. for ½ to 3 minutes. Finally, development may be carried out using as the developer an aqueous alkali solution, such as 0.1 to 5 wt %, and preferably 2 to 3 wt %, tetramethylammonium hydroxide (TMAH), this being done by a conventional technique such as dip, puddle, or spray technique for a period of 10 seconds to 3 minutes, and preferably 30 seconds to 2 minutes. These steps result in the formation of the desired pattern on the substrate.

In forming a pattern using the resist composition of the invention, another approach known as immersion lithography may be employed involving applying the resist composition by the same procedure as described above, feeding a liquid between the wafer and a projection lens, and exposing the resist coating to high-energy radiation through a mask. The liquid fill between the wafer and the projection lens should have a higher refractive index and high transparency. In the ArF immersion lithography, water having a refractive index of 1.44 at wavelength 193 nm is often used. It is expected that the higher the refractive index of liquid, the better becomes the resolution. It is thus recommended to use liquids having a refractive index of 1.6 or higher such as phosphoric acid, ethylene glycol and trialkoxyaluminum.

Of the various types of high-energy radiation that may be used, the resist composition of the invention is best suited to micro-pattern formation with, in particular, deep-UV rays having a wavelength of 254 to 120 nm, an excimer laser, especially ArF excimer laser (193 nm), KrAr excimer laser (134 nm), $F_2$ laser (157 nm), $Kr_2$ laser (146 nm) or $Ar_2$ laser (126 nm), x-rays, or an electron beam. The desired pattern may not be obtainable outside the upper and lower limits of the above range.

EXAMPLE

Examples of the invention are given below by way of illustration and not by way of limitation. The abbreviations used herein are NMR for nuclear magnetic resonance, Mw for weight average molecular weight, and Mn for number average molecular weight. Mw and Mn are determined by gel permeation chromatography (GPC) using polystyrene standards.

Monomer Synthesis Example 1

Synthesis of Monomer 1

A 3-L four-necked flask was charged with 113.8 g of 1,1,1,3,3,3-hexafluoro-2-propanol and 500 ml of tetrahydrofuran (THF). The flask was placed in a dry ice bath and cooled to an internal temperature below −60° C. while stirring the mixture in a nitrogen atmosphere. While the flask temperature was kept below −55° C., 500 ml of a n-hexane solution of 2.71M n-butyllithium was added dropwise followed by 2 hours of stirring at −30° C.

The flask was then placed in an ice bath, and 25.0 g of ethyl formate was added dropwise thereto. After the completion of dropwise addition, the ice bath was removed. The flask was placed in an oil bath, instead, where stirring was continued for 24 hours while keeping the internal temperature at 50° C.

The oil bath was removed. The flask was placed in an ice bath, instead. While keeping the temperature below 10° C., 270 ml of a THF solution of 3.0M methylmagnesium chloride was added dropwise. After the completion of dropwise addition, the ice bath was removed. Stirring was continued at room temperature for 7 hours. A saturated aqueous solution of ammonium chloride was added to the reaction mixture, followed by extraction with ethyl acetate. Ordinary post-treatments including washing, drying and concentration were carried out. Upon purification by silica gel chromatography, 191.1 g of Alcohol 1, identified below, was obtained in a yield of 83%.

The thus obtained Alcohol 1, 150 g, was dissolved in 1 L of THF, which was transferred to a 5 L four-necked flask. 68.4 g of methacryloyl chloride was fed to the flask, which was cooled in an ice bath. While keeping below 5° C., 79.8 g of triethylamine was added dropwise. The reaction mixture was stirred at 0° C. for 30 minutes and then at room temperature for 24 hours. 1 L of water was added to the reaction mixture, which was stirred at room temperature for 2 hours, followed by extraction with diethyl ether. Through ordinary post-treatments including washing, drying and concentration, a crude product was obtained. Upon purification by silica gel chromatography, 120.6 g of Monomer 1, identified below, was obtained in a yield of 67%.

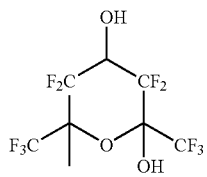

Alcohol 1

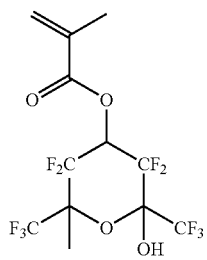

Monomer 1

Each of Alcohol 1 and Monomer 1 is obtained as a mixture of two isomers attributable to a 6-membered ring structure. The spectral data for Alcohol 1 are shown as Alcohol 1-1 and Alcohol 1-2, and the spectral date for Monomer 1 are shown as Monomer 1-1 and Monomer 1-2. In the description of subsequent polymer synthesis examples, the term "Monomer 1" denotes a mixture of Monomers 1-1 and 1-2.

Spectral Data of Alcohol 1-1

IR (KBr): ν=3583, 3382, 1346, 1234, 1178, 1097, 1029, 916 cm$^{-1}$ $^1$H-NMR (300.5 MHz in DMSO-d6): δ=1.54 (3H, br.s), 4.61 (1H, tt, J=4.7, 22.2 Hz), 7.26 (1H, OH, br.s), 10.06 (1H, OH, s) ppm $^{19}$F-NMR (282.8 MHz in DMSO-d6): δ=−132.89 (1F, dm, J=250 Hz), −123.13 (1F, dt-like, J=267, 23 Hz), −119.96 (1F, dm, J=244 Hz), −118.00 (1F, dm, J=269 Hz), −79.39 (3F, dd-like, J=7, 15 Hz), −70.87 (3F, d, J=12 Hz) ppm Spectral Data of Alcohol 1-2

IR (KBr): ν=3556, 3332, 1342, 1216, 1172, 1089, 1031, 939 cm$^{-1}$ $^1$H-NMR (300.5 MHz in DMSO-d6): δ=1.77 (3H, br.s), 4.83 (1H, tt, J=4.7, 21.5 Hz), 7.16 (1H, OH, br.s), 9.82 (1H, OH, s) ppm $^{19}$F-NMR (282.8 MHz in DMSO-d6): δ=−132.94 (1F, dm, J=250 Hz), −129.42 (1F, dhex-like, J=251, ca. 19 Hz), −119.52 (1F, dm, J=248 Hz), −113.72 (1F, dm, J=251 Hz), −80.00 (3F, dd, J=6.9, 14 Hz), −77.92 (3F, dd, J=6.9, 17 Hz) ppm Spectral Data of Monomer 1-1

IR (KBr): ν=3409, 1731, 1349, 1288, 1228, 1172, 1151, 1093, 1086 cm$^{-1}$ $^1$H-NMR (300.5 MHz in DMSO-d6): δ=1.61 (3H, s), 1.97 (3H, s), 5.98-6.02 (1H, m), 6.14-6.27 (1H, m), 6.26-6.30 (1H, m), 10.82 (1H, OH, d, J=3.2 Hz) ppm $^{19}$F-NMR (282.8 MHz in DMSO-d6): δ=−129.73 (1F, dm, J=246 Hz), −119.95 (1F, dm, J=267 Hz), −119.42 (1F, dm, J=246 Hz), −117.60–−117.00 (1F, m), −79.20 (3F, dd, J=6.9, 13.9 Hz), −70.86 (3F, d, J=10.4 Hz) ppm Spectral Data of Monomer 1-2

IR (KBr): ν=3405, 1731, 1348, 1272, 1218, 1178, 1153, 1128, 1087 cm$^{-1}$ $^{1}$H-NMR (300.5 MHz in DMSO-d6): δ=1.84-1.88 (3H, m), 1.98 (3H, s), 6.00 (1H, t, J=1.4 Hz), 6.19 (1H, tt, J=4.1, 25 Hz), 6.28 (1H, t, J=0.8 Hz), 10.62 (1H, OH, d, J=3.4 Hz) ppm $^{19}$F-NMR (282.8 MHz in DMSO-d6): δ=−129.97 (1F, dm, J=248 Hz), −125.90 (1F, dm, J=251 Hz), −119.31 (1F, dm, J=247 Hz), −112.68 (1F, dm, J=251 Hz), −79.89 (3F, dd, J=8.7, 16 Hz), −77.93 (3F, dd, J=5.2, 17 Hz) ppm Polymer Synthesis Example 1

Synthesis of Homopolymer from Monomer 1

In a 100-ml flask, 10.0 g of Monomer 1 and 20 g of PGMEA were mixed. Oxygen was expelled from the system, after which 0.16 g of AIBN was added to and fully dissolved in the mixture in a nitrogen atmosphere. To a 100-ml flask which was charged with 10 g of PGMEA and kept at a temperature of 80° C., the monomer solution was added dropwise over 4 hours. After the completion of dropwise addition, stirring was continued at 80° C. for a further 2 hours. The reaction mixture was cooled down to room temperature and admitted into 250 g of n-hexane whereupon a polymer precipitated. The polymer was washed with n-hexane, isolated and dried in vacuum at 40° C. for 20 hours. There was obtained 8.0 g of a white polymer, designated Polymer 1, which had a Mw of 7,800 and a dispersity (Mw/Mn) of 1.3 as determined by GPC.

Polymer 1 was dissolved in a 2.38 wt % aqueous solution of tetramethylammonium hydroxide, finding a dissolution rate of 5,000 Å/sec.

Polymer Synthesis Example 2

Copolymerization of 3-ethyl-3-exo-tetracyclo[4.4.0.1$^{2,5}$.1$^{7,10}$]-dodecanyl methacrylate, 3-hydroxy-1-adamantyl methacrylate, 4,8-dioxatricyclo[4.2.1.0$^{3,7}$]nonan-5-on-2-yl methacrylate, and Monomer 1 (25/25/40/10)

A 300-mL flask was charged with 5.31 g of 3-ethyl-3-exo-tetracyclo[4.4.0.1$^{2,5}$.1$^{7,10}$]dodecanyl methacrylate, 4.58 g of 3-hydroxy-1-adamantyl methacrylate, 6.95 g of 4,8-dioxatricyclo[4.2.1.0$^{3,7}$]nonan-5-on-2-yl methacrylate, 3.16 g of Monomer 1 and 40 g of PGMEA. Oxygen was expelled from the system, after which 0.25 g of AIBN was added to and fully dissolved in the mixture in a nitrogen atmosphere. To a 300-ml flask which was charged with 20 g of PGMEA and kept at a temperature of 80° C., the monomer solution was added dropwise over 4 hours. After the completion of dropwise addition, stirring was continued at 80° C. for a further 2 hours. The reaction mixture was cooled down to room temperature and admitted into 500 g of n-hexane whereupon a polymer precipitated. The polymer was washed with n-hexane, isolated and dried in vacuum at 40° C. for 20 hours. There was obtained 15.5 g of a white polymer, designated Polymer 2, which had a Mw of 8,200 and a dispersity (Mw/Mn) of 1.5 as determined by GPC.

From an integration ratio of its $^{1}$H-NMR spectrum, Polymer 2 was found to have a copolymer composition ratio (molar ratio) of 25.0:25.3:40.3:9.4.

Polymer Synthesis Example 3

Copolymerization of 3-ethyl-3-exo-tetracyclo[4.4.0.1$^{2,5}$.1$^{7,10}$]-dodecanyl methacrylate, 3-hydroxy-1-adamantyl methacrylate, 4,8-dioxatricyclo[4.2.1.0$^{3,7}$]nonan-5-on-2-yl methacrylate, and Monomer 1 (25/25/30/20)

A 300-mL flask was charged with 4.96 g of 3-ethyl-3-exo-tetracyclo[4.4.0.1$^{2,5}$.1$^{7,10}$]dodecanyl methacrylate, 4.27 g of 3-hydroxy-1-adamantyl methacrylate, 4.86 g of 4,8-dioxatricyclo[4.2.1.0$^{3,7}$]nonan-5-on-2-yl methacrylate, 5.90 g of Monomer 1 and 40 g of PGMEA. Oxygen was expelled from the system, after which 0.25 g of AIBN was added to and fully dissolved in the mixture in a nitrogen atmosphere. To a 300-ml flask which was charged with 20 g of PGMEA and kept at a temperature of 80° C., the monomer solution was added dropwise over 4 hours. After the completion of dropwise addition, stirring was continued at 80° C. for a further 2 hours. The reaction mixture was cooled down to room temperature and admitted into 500 g of n-hexane whereupon a polymer precipitated. The polymer was washed with n-hexane, isolated and dried in vacuum at 40° C. for 20 hours. There was obtained 15.2 g of a white polymer, designated Polymer 3, which had a Mw of 7,900 and a dispersity (Mw/Mn) of 1.5 as determined by GPC.

From an integration ratio of its $^{1}$H-NMR spectrum, Polymer 3 was found to have a copolymer composition ratio (molar ratio) of 25.1:25.2:30.2:19.5.

Polymer Synthesis Example 4

Copolymerization of 2-ethyl-2-adamantyl methacrylate, 3-hydroxy-1-adamantyl methacrylate, 4,8-dioxatricyclo[4.2.1.0$^{3,7}$]nonan-5-on-2-yl methacrylate, and Monomer 1 (25/25/30/20)

A 300-mL flask was charged with 4.93 g of 2-ethyl-2-adamantyl methacrylate, 4.70 g of 3-hydroxy-1-adamantyl methacrylate, 7.13 g of 4,8-dioxatricyclo[4.2.1.0$^{3,7}$]nonan-5-on-2-yl methacrylate, 3.24 g of Monomer 1 and 40 g of PGMEA. Oxygen was expelled from the system, after which 0.26 g of AIBN was added to and fully dissolved in the mixture in a nitrogen atmosphere. To a 300-ml flask which was charged with 20 g of PGMEA and kept at a temperature of 80° C., the monomer solution was added dropwise over 4 hours. After the completion of dropwise addition, stirring was continued at 80° C. for a further 2 hours. The reaction mixture was cooled down to room temperature and admitted into 500 g of n-hexane whereupon a polymer precipitated. The polymer was washed with n-hexane, isolated and dried in vacuum at 40° C. for 20 hours. There was obtained 15.0 g of a white polymer, designated Polymer 4, which had a Mw of 7,700 and a dispersity (Mw/Mn) of 1.5 as determined by GPC.

From an integration ratio of its $^{1}$H-NMR spectrum, Polymer 4 was found to have a copolymer composition ratio (molar ratio) of 25.1:24.9:30.1:19.9.

Polymer Synthesis Example 5

Copolymerization of 1-ethylcyclopentyl methacrylate, 3-hydroxy-1-adamantyl methacrylate, 4,8-dioxatricyclo[4.2.1.0$^{3,7}$]nonan-5-on-2-yl methacrylate, and Monomer 1 (25/25/30/20)

A 300-mL flask was charged with 3.88 g of 1-ethylcyclopentyl methacrylate, 5.02 g of 3-hydroxy-1-adamantyl methacrylate, 7.63 g of 4,8-dioxatricyclo[4.2.1.0$^{3,7}$]nonan-5-on-2-yl methacrylate, 3.47 g of Monomer 1 and 40 g of PGMEA.

Oxygen was expelled from the system, after which 0.28 g of AIBN was added to and fully dissolved in the mixture in a nitrogen atmosphere. To a 300-ml flask which was charged with 20 g of PGMEA and kept at a temperature of 80° C., the monomer solution was added dropwise over 4 hours. After the completion of dropwise addition, stirring was continued at 80° C. for a further 2 hours. The reaction mixture was cooled down to room temperature and admitted into 500 g of n-hexane whereupon a polymer precipitated. The polymer was washed with n-hexane, isolated and dried in vacuum at 40° C. for 20 hours. There was obtained 15.6 g of a white polymer, designated Polymer 5, which had a Mw of 7,800 and a dispersity (Mw/Mn) of 1.5 as determined by GPC.

From an integration ratio of its $^1$H-NMR spectrum, Polymer 5 was found to have a copolymer composition ratio (molar ratio) of 24.7:25.3:30.0:20.0.

Polymer Synthesis Example 6

Copolymerization of 1-(1-adamantyl)-1-methylethyl methacrylate, 3-hydroxy-1-adamantyl methacrylate, 4,8-dioxatricyclo[4.2.1.0$^{3,7}$]nonan-5-on-2-yl methacrylate, and Monomer 1 (25/25/30/20)

A 300-mL flask was charged with 5.14 g of 1-(1-adamantyl)-1-methylethyl methacrylate, 4.63 g of 3-hydroxy-1-adamantyl methacrylate, 7.03 g of 4,8-dioxatricyclo[4.2.1.0$^{3,7}$]nonan-5-on-2-yl methacrylate, 3.20 g of Monomer 1 and 40 g of PGMEA. Oxygen was expelled from the system, after which 0.26 g of AIBN was added to and fully dissolved in the mixture in a nitrogen atmosphere. To a 300-ml flask which was charged with 20 g of PGMEA and kept at a temperature of 80° C., the monomer solution was added dropwise over 4 hours. After the completion of dropwise addition, stirring was continued at 80° C. for a further 2 hours. The reaction mixture was cooled down to room temperature and admitted into 500 g of n-hexane whereupon a polymer precipitated. The polymer was washed with n-hexane, isolated and dried in vacuum at 40° C. for 20 hours. There was obtained 15.0 g of a white polymer, designated Polymer 6, which had a Mw of 7,700 and a dispersity (Mw/Mn) of 1.5 as determined by GPC.

From an integration ratio of its $^1$H-NMR spectrum, Polymer 6 was found to have a copolymer composition ratio (molar ratio) of 24.5:25.2:30.5:19.8.

Polymer Synthesis Example 7

Copolymerization of Monomer 2 and Monomer 3 (70/30)

A 300-mL flask was charged with 15.95 g of Monomer 2, 4.05 g of Monomer 3 and 5 g of toluene. Oxygen was expelled from the system, after which 0.32 g of AIBN was added to the mixture in a nitrogen atmosphere. Stirring was continued for 24 hours while keeping the temperature at 60° C. The reaction mixture was cooled to room temperature, combined with 55 g of toluene, and admitted into 500 g of n-hexane whereupon a polymer precipitated. The polymer was washed with n-hexane, isolated and dried in vacuum at 40° C. for 20 hours. There was obtained 13.0 g of a white polymer, designated Polymer 7, which had a Mw of 7,300 and a dispersity (Mw/Mn) of 1.6 as determined by GPC.

From an integration ratio of its $^1$H-NMR spectrum, Polymer 7 was found to have a copolymer composition ratio (molar ratio) of 69.5:30.5.

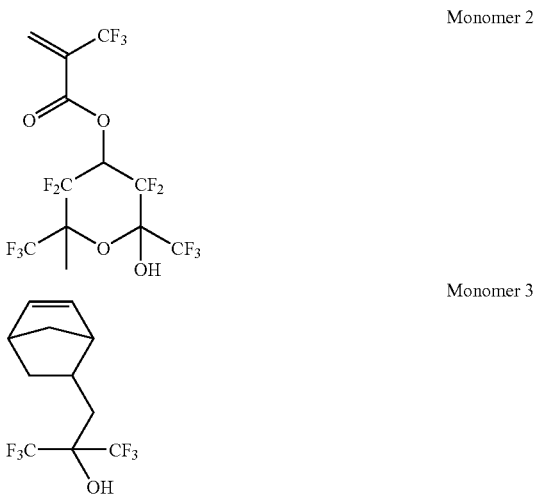

Comparative Polymer Synthesis Example 1

Copolymerization of 3-ethyl-3-exo-tetracyclo[4.4.0.1$^{2,5}$.1$^{7,10}$]dodecanyl methacrylate, 3-hydroxy-1-adamantyl methacrylate, and 4,8-dioxatricyclo[4.2.1.0$^{3,7}$]nonan-5-on-2-yl methacrylate (30/25/45)

A 300-mL flask was charged with 6.80 g of 3-ethyl-3-exo-tetracyclo[4.4.0.1$^{2,5}$.1$^{7,10}$]dodecanyl methacrylate, 4.88 g of 3-hydroxy-1-adamantyl methacrylate, 8.33 g of 4,8-dioxatricyclo[4.2.1.0$^{3,7}$]nonan-5-on-2-yl methacrylate, and 40 g of PGMEA. Oxygen was expelled from the system, after which 0.27 g of AIBN was added to and fully dissolved in the mixture in a nitrogen atmosphere. To a 300-ml flask which was charged with 20 g of PGMEA and kept at a temperature of 80° C., the monomer solution was added dropwise over 4 hours. After the completion of dropwise addition, stirring was continued at 80° C. for a further 2 hours. The reaction mixture was cooled down to room temperature and admitted into 500 g of n-hexane whereupon a polymer precipitated. The polymer was washed with n-hexane, isolated and dried in vacuum at 40° C. for 20 hours. There was obtained 15.7 g of a white polymer, designated Comparative Polymer 1, which had a Mw of 8,300 and a dispersity (Mw/Mn) of 1.5 as determined by GPC.

From an integration ratio of its $^1$H-NMR spectrum, Comparative Polymer 1 was found to have a copolymer composition ratio (molar ratio) of 30.0:24.5:45.5.

Resist Preparation and Exposure

Resist solutions were prepared by mixing the polymer (Inventive Polymers 2 to 7, Comparative Polymer 1), photoacid generator (PAG1 to PAG3), dissolution inhibitor (DRII), basic compound (TMMEA, AAA, and AACN) in a solvent (PGMEA) in the amounts shown in Table 1 and processing in an ordinary manner.

On silicon wafers having a film of ARC-29A (Nissan Chemicals Industries, Ltd.) coated to a thickness of 78 nm, the resist solutions were spin coated, then baked on a hot plate at 120° C. for 90 seconds to give resist films having a thickness of 200 nm.

The resist films were exposed by means of an ArF excimer laser scanner model NSR-S305B (Nikon Corp., NA 0.68, σ 0.85, ⅔ annular illumination, normal mask) while varying the exposure dose. Immediately after exposure, the resist films were baked (PEB) at 110° C. for 90 seconds and then developed for 60 seconds with a 2.38% aqueous solution of tetramethylammonium hydroxide, obtaining positive patterns.

The resist patterns were evaluated. The exposure dose (mJ/cm$^2$) at which a 0.12-µm line-and-space (1:1) pattern was resolved is the optimum dose. The minimum line width (nm) of a L/S (1:1) pattern which was ascertained separate at this dose is the resolution. Using a measuring SEM model S-9220 (Hitachi Ltd.), the 0.12-µm L/S (1:1) pattern was measured for line edge roughness. The results are also shown in Table 1.

TABLE 1

| Polymer (pbw) | Photoacid generator (pbw) | Basic compound (pbw) | Dissolution inhibitor (pbw) | Solvent (pbw) | Sensitivity (mJ/cm$^2$) | Resolution (nm) | Line edge roughness (nm) |
|---|---|---|---|---|---|---|---|
| Polymer 2 (100) | PAG1 (3) | TMMEA (0.4) | — | PGMEA (800) | 25 | 100 | 7.2 |
| Polymer 3 (100) | PAG1 (3) | TMMEA (0.4) | — | PGMEA (800) | 26 | 100 | 7.0 |
| Polymer 2 (100) | PAG2 (4) PAG3 (3) | TMMEA (0.2) | — | PGMEA (800) | 32 | 100 | 8.2 |
| Polymer 2 (100) | PAG1 (3) | AAA (0.4) | — | PGMEA (800) | 26 | 100 | 7.6 |
| Polymer 2 (100) | PAG1 (3) | AACN (0.4) | — | PGMEA (800) | 28 | 100 | 7.8 |
| Polymer 2 (100) | PAG1 (3) | TMMEA (0.4) | DRI1 (10) | PGMEA (800) | 22 | 100 | 7.1 |
| Polymer 2 (50) + Polymer 8 (50) | PAG1 (3) | TMMEA (0.4) | — | PGMEA (800) | 19 | 110 | 6.8 |
| Polymer 2 (50) + Polymer 9 (50) | PAG1 (3) | TMMEA (0.4) | — | PGMEA (800) | 22 | 110 | 7.2 |
| Polymer 2 (80) + Polymer 10 (20) | PAG1 (3) | TMMEA (0.4) | — | PGMEA (800) | 26 | 110 | 7.6 |
| Comparative Polymer 1 (100) | PAG1 (3) | TMMEA (0.4) | — | PGMEA (800) | 33 | 110 | 9.3 |

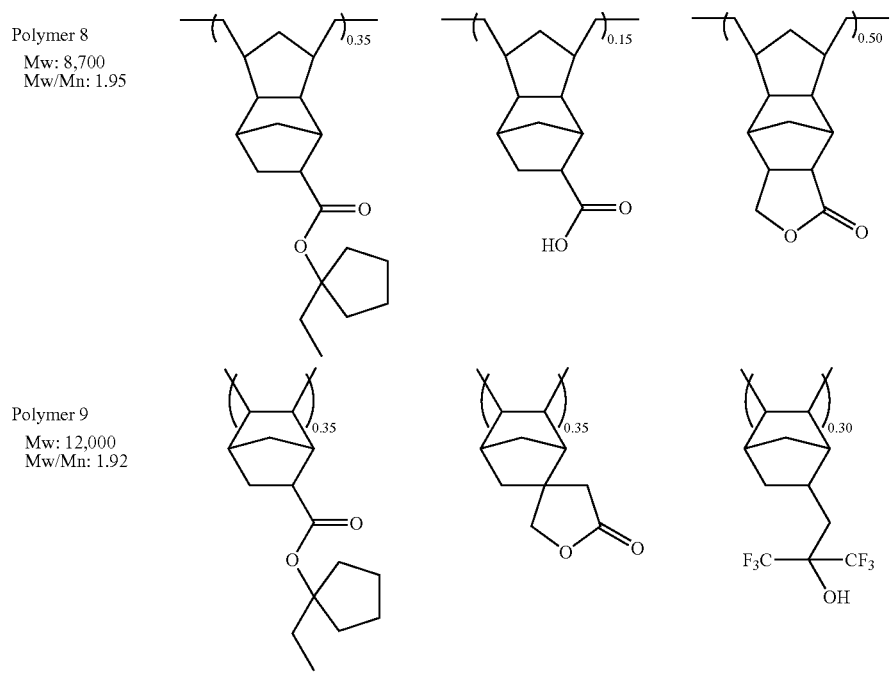

Polymer 8
Mw: 8,700
Mw/Mn: 1.95

Polymer 9
Mw: 12,000
Mw/Mn: 1.92

TABLE 1-continued

| Polymer (pbw) | Photoacid generator (pbw) | Basic compound (pbw) | Dissolution inhibitor (pbw) | Solvent (pbw) | Sensitivity (mJ/cm$^2$) | Resolution (mm) | Line edge roughness (nm) |
| --- | --- | --- | --- | --- | --- | --- | --- |

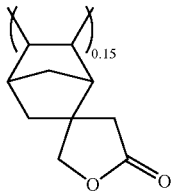

Polymer 10
Mw: 11,000
Mw/Mn: 1.98

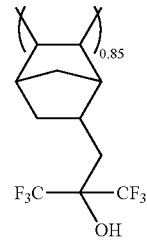

PAG1        PAG2        PAG3        DRI1

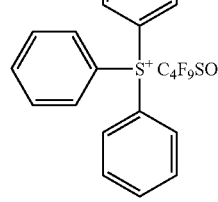

TMMEA        AAA        AACN

PGMEA: propylene glycol monomethyl ether acetate

Dry Etching Test

Each polymer, 2 g, was thoroughly dissolved in 10 g of PGMEA, and passed through a filter having a pore size of 0.2 μm, obtaining a polymer solution. The polymer solution was spin coated onto a silicon substrate and baked, forming a polymer film of 300 nm thick. Dry etching tests were carried out on the polymer films by etching them under two sets of conditions. In an etching test with CHF$_3$/CF$_4$ gas, a dry etching instrument TE-8500P (Tokyo Electron K.K.) was used. In an etching test with Cl$_2$/BCl$_3$ gas, a dry etching instrument L-507D-L (Nichiden Anerba K.K.) was used. In each test, the difference in polymer film thickness before and after etching was determined. The etching conditions are summarized in Table 2.

TABLE 2

|  | CHF$_3$/CF$_4$ gas | Cl$_2$/BCl$_3$ gas |
| --- | --- | --- |
| Chamber pressure (Pa) | 40.0 | 40.0 |
| RF power (W) | 1300 | 300 |
| Gap (mm) | 9 | 9 |
| Gas flow rate (ml/min) | CHF$_3$: 30 | Cl$_2$: 30 |
|  | CF$_4$: 30 | BCl$_3$: 30 |
|  | Ar: 100 | CHF$_3$: 100 |
|  |  | O$_2$: 2 |
| Time (sec) | 60 | 60 |

The results of etching tests are shown in Table 3. In this evaluation, a less difference in polymer film thickness, i.e., a less film loss indicates more etching resistance. It is seen that inventive resist compositions have etching resistance comparable to the prior art resist compositions.

TABLE 3

| Polymer (pbw) | CHF$_3$/CF$_4$ gas etching rate (nm/min) | Cl$_2$/BCl$_3$ gas etching rate (nm/min) |
|---|---|---|
| Polymer 1 (100) | 139 | 148 |
| Polymer 2 (100) | 138 | 143 |
| Polymer 3 (100) | 133 | 140 |
| Polymer 2 (50) + Polymer 8 (50) | 116 | 125 |
| Polymer 2 (50) + Polymer 9 (50) | 111 | 126 |
| Polymer 2 (80) + Polymer 10 (20) | 128 | 133 |
| Comparative Polymer 1 (100) | 133 | 144 |

Dissolution Behavior of Resist in Developer as Analyzed by QCM

The above-prepared resist solution (the base resin is Polymer 1 or Comparative Polymer 1) was passed through a filter having a pore size of 0.2 μm, spin coated on a quartz substrate with a size of 1 inch (~2.5 cm) having a gold undercoat and a chromium electrode vapor deposited thereon, and baked on a hot plate at 130° C. for 60 seconds, forming a resist film of 250 nm thick. The resist film was exposed by means of an ArF exposure system ArFES3000 (Litho Tech Japan Co., Ltd.) and baked (PEB) at 110° C. for 60 seconds. The substrate was set on a quartz oscillator microbalance instrument RDA-Qz3 for resist development analysis (Litho Tech Japan Co., Ltd.). Development in a 2.38 wt % aqueous solution of tetramethylammonium hydroxide was carried out for 60 seconds, during which swell and dissolution were measured (oscillation mode AT cut). Exposure was made in a varying exposure dose, and QCM measurement performed on every dose.

Figure 2:
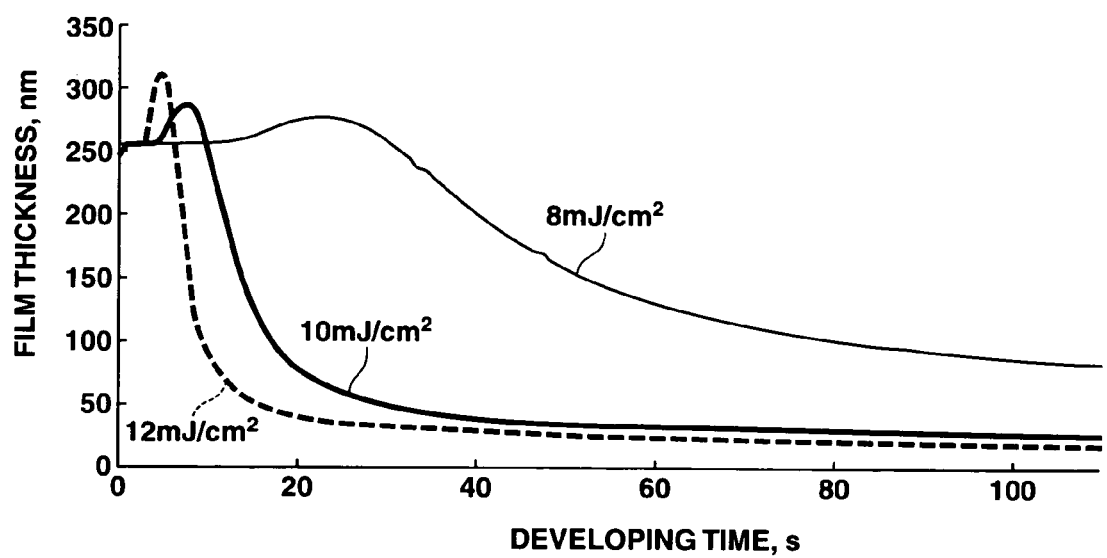
FIG. 2 is a graph showing the thickness versus developing time of a resist film formed from the resist composition of Comparative Polymer 1, as analyzed by the QCM technique.

The results from the resist compositions of Polymer 1 and Comparative Polymer 1 are plotted in FIGS. 1 and 2, respectively. In the charts plotting resist film thickness versus developing time, an increase of film thickness with developing time indicates swell, and a decrease of film thickness with developing time indicates dissolution. It is seen from FIGS. 1 and 2 that the resist composition of Polymer 1 experiences substantially restrained swell during development.

Japanese Patent Application No. 2004-313903 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A polymerizable fluorinated compound having the general formula (2a) or (2b):

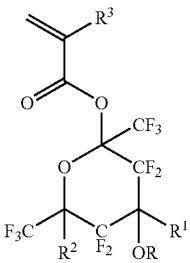

(2a)

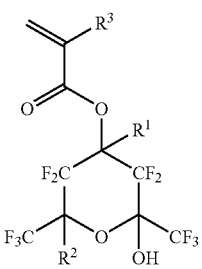

(2b)

wherein $R^1$ and $R^2$ each are hydrogen or a straight, branched or cyclic $C_1$-$C_{20}$ alkyl or fluoroalkyl group, $R^3$ is hydrogen, fluorine, or a $C_1$-$C_4$ alkyl or fluoroalkyl group, and R is hydrogen or a protective group.

2. The polymerizable fluorinated compound of claim 1, wherein the general formula (2a) or (2b) includes the following formula (2a-1) or (2b-1):

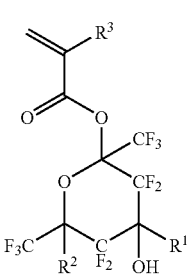

(2a-1)

(2b-1)

wherein $R^1$, $R^2$ and $R^3$ are defined as in claim 1.

3. The polymerizable fluorinated compound of claim 2, wherein the general formula (2a-1) is selected from the group of consisting of the following formulae:

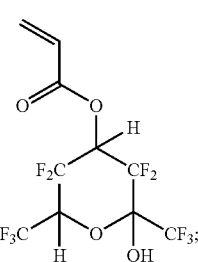 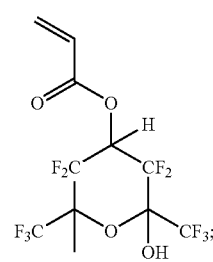

-continued

-continued

-continued
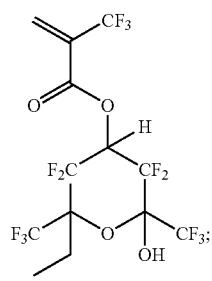
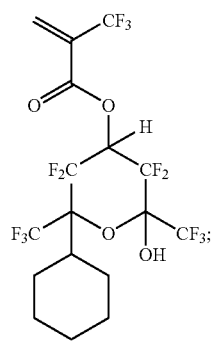
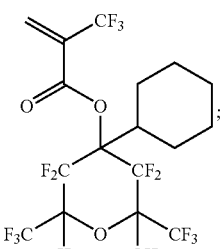
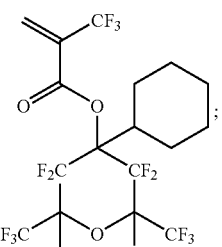
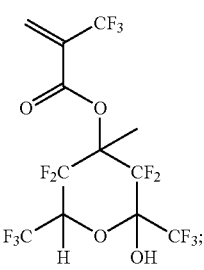
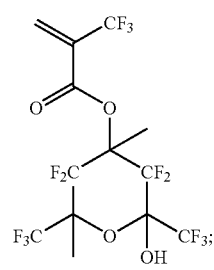
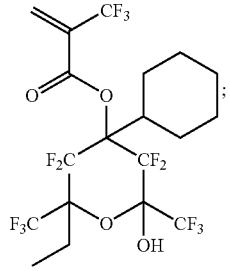
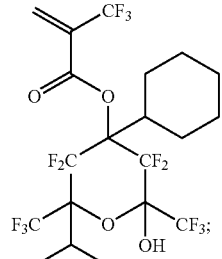
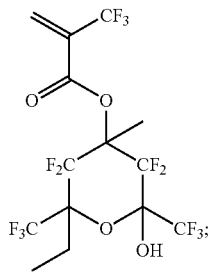
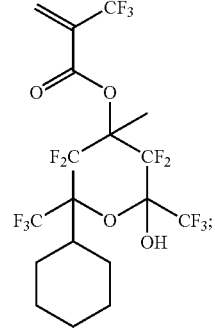
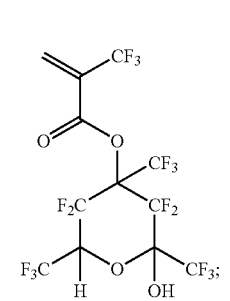
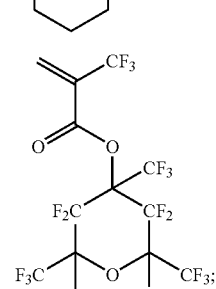
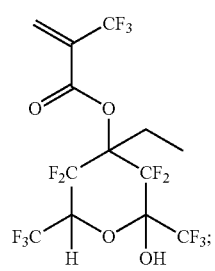
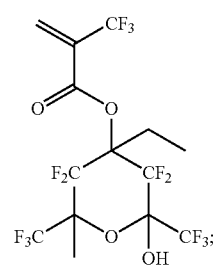
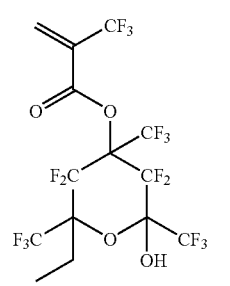 and 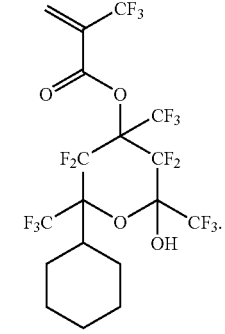
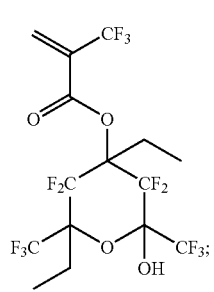
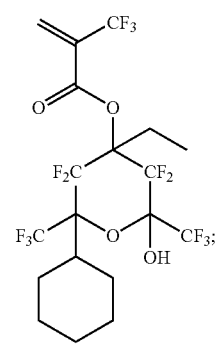
4. The polymerizable fluorinated compound of claim 2, wherein the general formula (2b-1) is selected from the group of consisting of the following formulae:
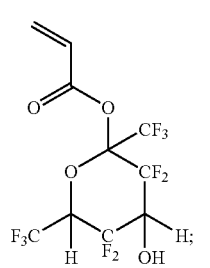
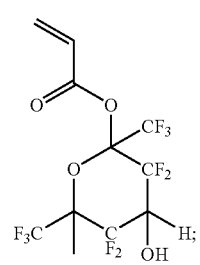

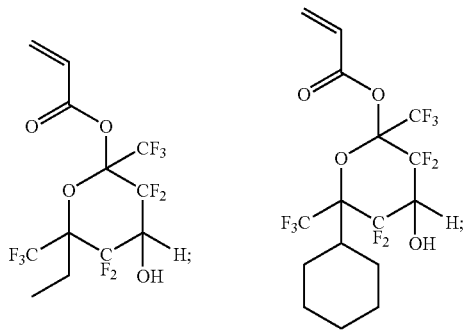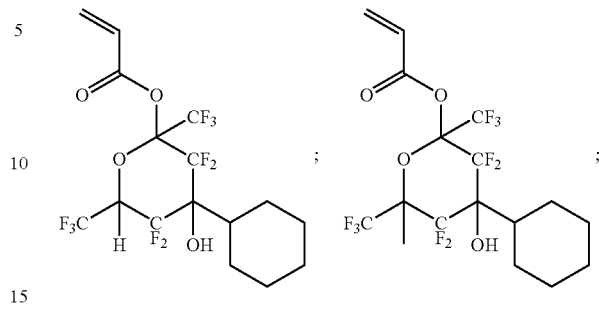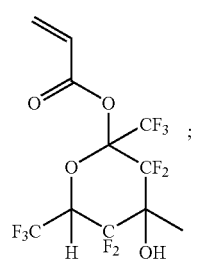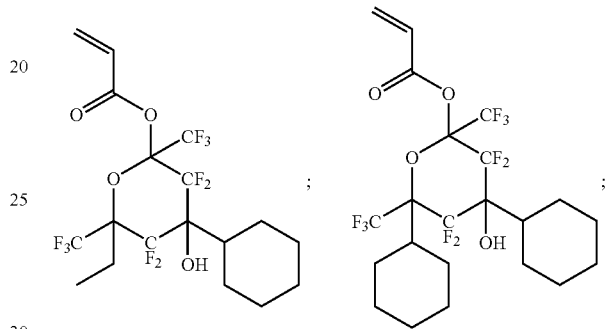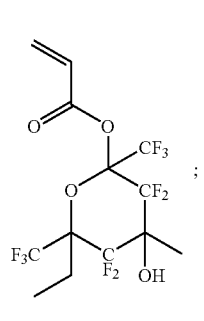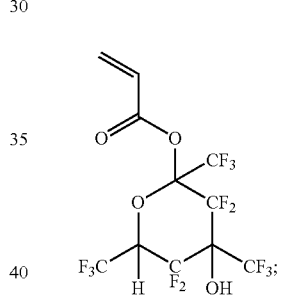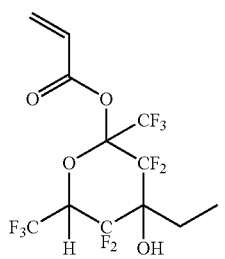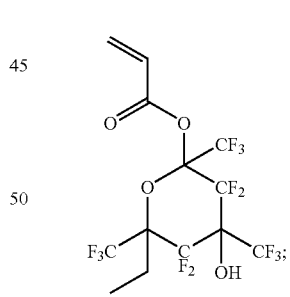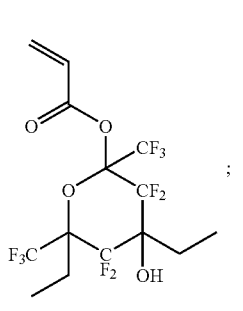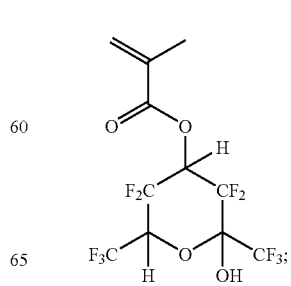

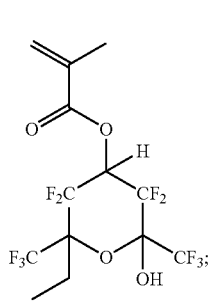
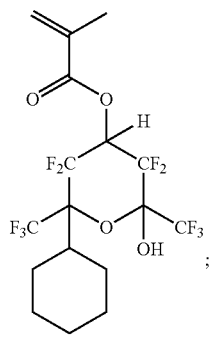
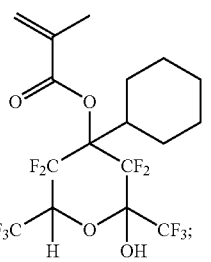
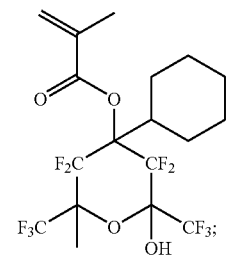
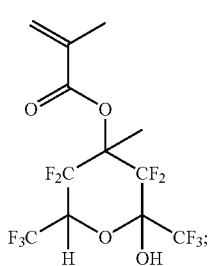
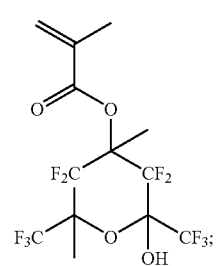
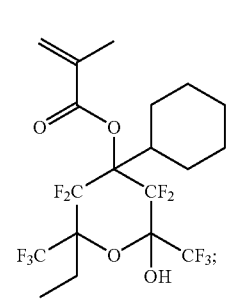
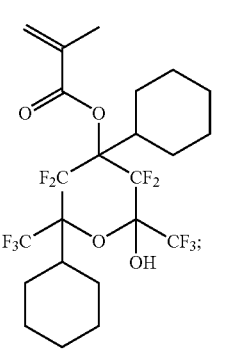
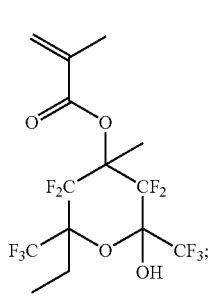
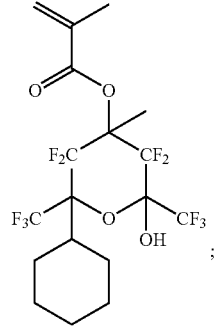
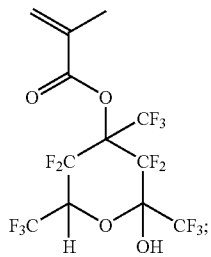
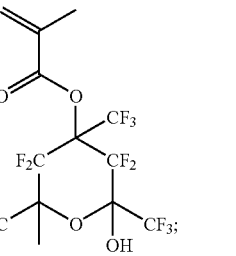
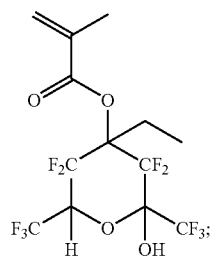
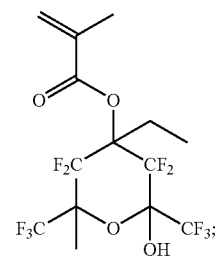
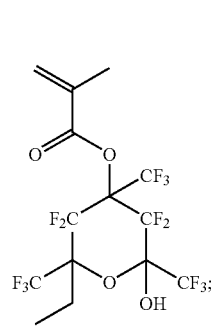
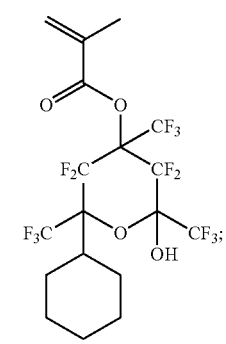
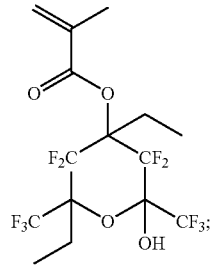
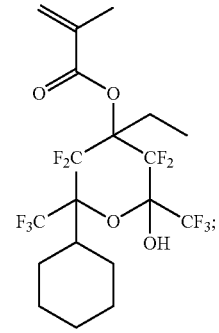
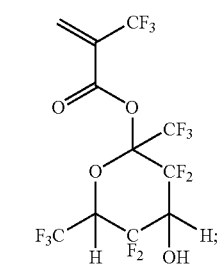
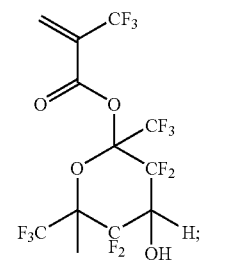

-continued
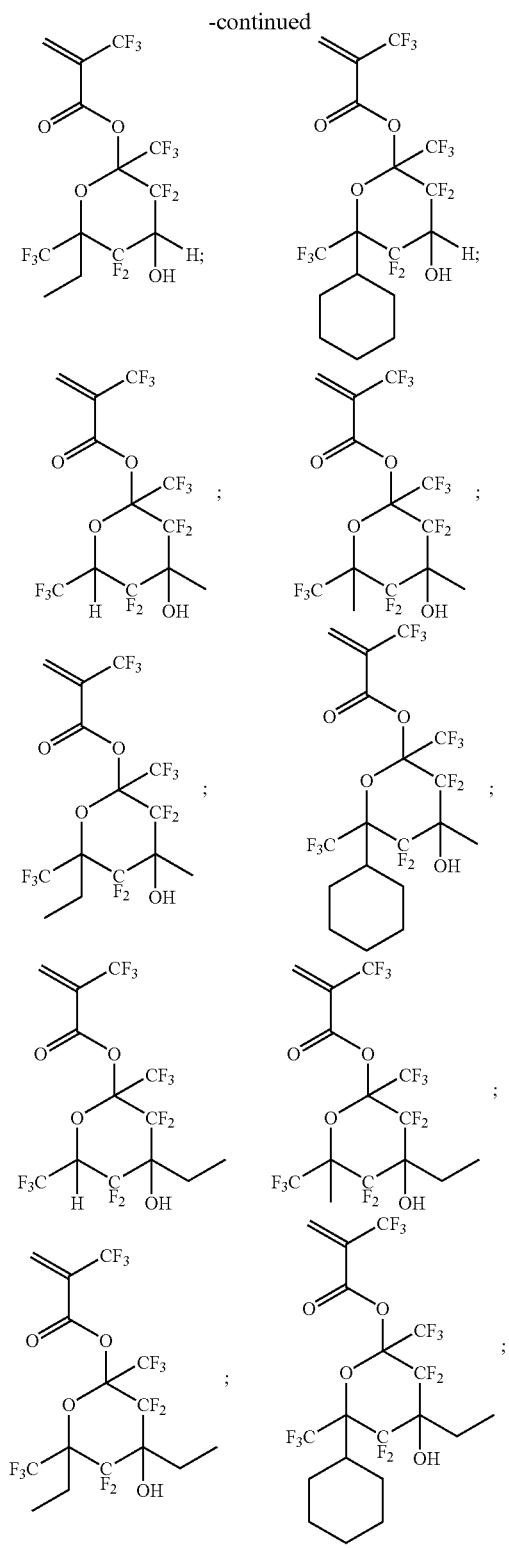
-continued
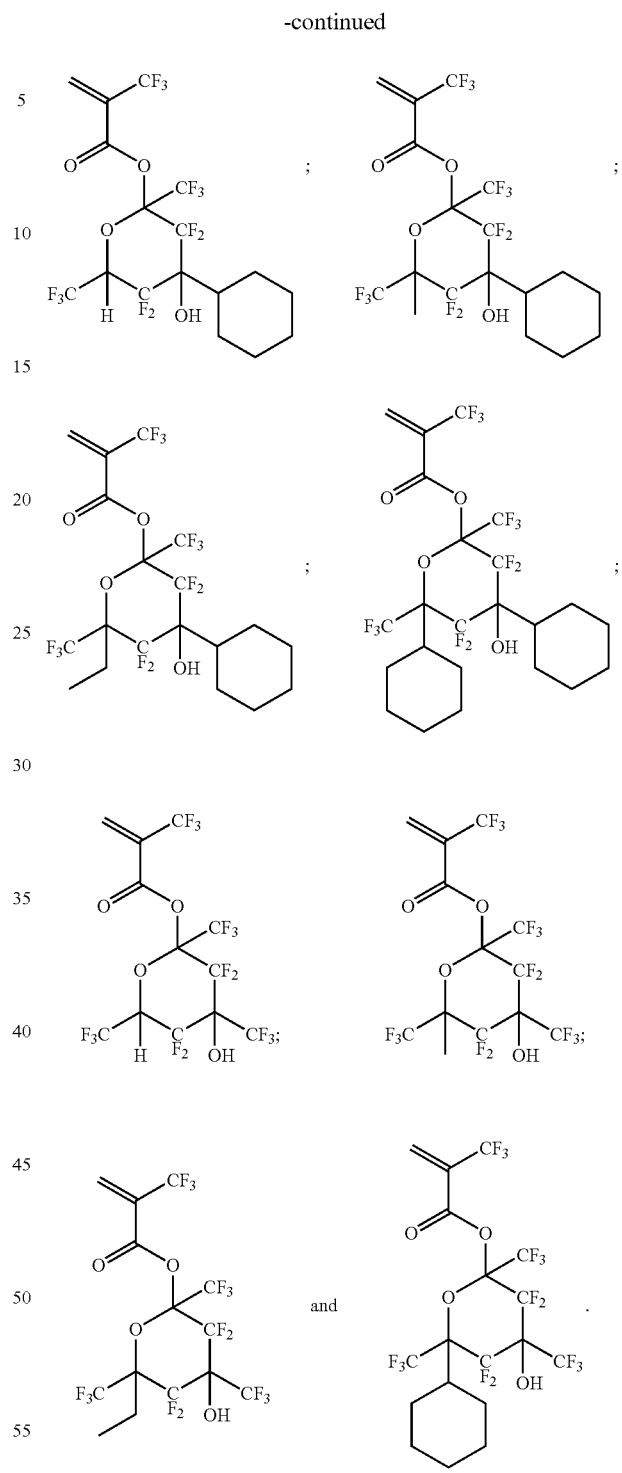
* * * * *

UNITED STATES PATENT AND TRADEMARK OFFICE
CERTIFICATE OF CORRECTION

PATENT NO. : 7,592,407 B2
APPLICATION NO. : 11/259179
DATED : September 22, 2009
INVENTOR(S) : Harada et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 819 days.

Signed and Sealed this

Twenty-first Day of September, 2010

David J. Kappos
*Director of the United States Patent and Trademark Office*